US010080792B2

(12) United States Patent
Alfenito et al.

(10) Patent No.: US 10,080,792 B2
(45) **Date of Patent: *Sep. 25, 2018**

(54) INFLUENZA VACCINE AND THERAPY

(71) Applicant: EnGen Bio, Inc., Redwood City, CA (US)

(72) Inventors: Mark Alfenito, Redwood City, CA (US); Mark Baer, San Francisco, CA (US); Doris Bucher, New York, NY (US); Geoffrey Yarranton, Burlingame, CA (US)

(73) Assignee: EnGen Bio, Inc., Redwood City, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/272,790

(22) Filed: Sep. 22, 2016

(65) Prior Publication Data

US 2017/0035876 A1 Feb. 9, 2017

Related U.S. Application Data

(63) Continuation-in-part of application No. 14/492,068, filed on Sep. 21, 2014, now Pat. No. 9,999,662.

(Continued)

(51) Int. Cl.

| | |
|---|---|
| ***A61K 39/12*** | (2006.01) |
| ***C07K 16/10*** | (2006.01) |
| *A61K 39/00* | (2006.01) |

(52) U.S. Cl.

CPC .......... *A61K 39/12* (2013.01); *C07K 16/1018* (2013.01); *A61K 2039/505* (2013.01);

(Continued)

(58) Field of Classification Search

None

See application file for complete search history.

(56) References Cited

U.S. PATENT DOCUMENTS

| | | | |
|---|---|---|---|
| 4,981,782 | A | 1/1991 | Judd et al. |
| 5,136,019 | A | 8/1992 | Judd et al. |

(Continued)

FOREIGN PATENT DOCUMENTS

| | | | |
|---|---|---|---|
| EP | 1 105 497 | B1 | 4/2007 |
| EP | 1 294 892 | B1 | 10/2007 |

(Continued)

OTHER PUBLICATIONS

UniProKB/Swiss-Prot: P26147.1, H1N1 (Year: 1993).*

(Continued)

*Primary Examiner* — Michelle S Horning

(74) *Attorney, Agent, or Firm* — HelixIP LLP

(57) ABSTRACT

The present invention is directed generally to M1 polypeptides that can be utilized as vaccines and/or antigens for generation of anti-M1 polypeptide antibodies for prophylactic treatment of individuals who are susceptible to infection by influenza virus. The anti-M1 polypeptide antibodies of the invention are useful for treatment of individuals infected with influenza virus, or useful for prophylactic treatment of individuals who are susceptible to infection by influenza virus, or for immune-suppressed individuals who cannot generate an effective antibody response.

3 Claims, 2 Drawing Sheets

Specification includes a Sequence Listing.

Related U.S. Application Data

(60) Provisional application No. 62/222,681, filed on Sep. 23, 2015, provisional application No. 61/881,325, filed on Sep. 23, 2013.

(52) U.S. Cl.
CPC .................... *A61K 2039/55* (2013.01); *A61K 2039/55566* (2013.01); *A61K 2039/6081* (2013.01); *C07K 2317/34* (2013.01); *C07K 2317/76* (2013.01); *C12N 2760/16134* (2013.01)

(56) References Cited

U.S. PATENT DOCUMENTS

| | | | |
|---|---|---|---|
| 5,243,030 A | 9/1993 | Judd et al. | |
| 5,616,327 A | 4/1997 | Judd et al. | |
| 7,344,722 B1 | 3/2008 | Maassab et al. | |
| 7,438,919 B2 | 10/2008 | Dowling et al. | |
| 7,556,940 B2 | 7/2009 | Galarza et al. | |
| 7,785,603 B2 | 8/2010 | Luke et al. | |
| 8,282,937 B2 | 10/2012 | Maassab et al. | |
| 8,357,789 B2 | 1/2013 | Amon et al. | |
| 8,592,196 B2 | 11/2013 | Kittel et al. | |
| 9,730,999 B2 * | 8/2017 | Hanon | A61K 39/145 |
| 2007/0172929 A1 | 7/2007 | Maassab et al. | |
| 2009/0074804 A1 | 3/2009 | Lee et al. | |
| 2011/0027314 A1 | 2/2011 | Broeker et al. | |
| 2013/0039938 A1 | 2/2013 | Smith et al. | |
| 2015/0086560 A1 | 3/2015 | Alfenito et al. | |

FOREIGN PATENT DOCUMENTS

| | | |
|---|---|---|
| EP | 1 140 164 B1 | 2/2009 |
| EP | 1 933 866 B1 | 12/2010 |
| EP | 1 951 296 B1 | 1/2011 |
| EP | 1 968 632 B1 | 4/2012 |
| EP | 1 945 659 B9 | 8/2012 |
| EP | 2 222 334 B1 | 5/2014 |
| EP | 2 407 480 B1 | 7/2014 |
| EP | 1 597 350 B1 | 4/2015 |
| EP | 3 045 915 | 7/2016 |
| WO | WO 199222575 | 12/1992 |
| WO | WO 2005120564 | 12/2005 |
| WO | WO 2012072088 | 6/2012 |

OTHER PUBLICATIONS

Acierno et al., Cross-reactivity between HLA-A2-restricted Flu-M1:58-66 and HIV p17 GAG:77-85 epitopes . . . J. Transl. Med. vol. 1, p. 3 (2003).
Biddison et al., Antibody to influenza virus matrix protein detects a common antigen on the surface of the cells . . . J. Exp. Med. vol. 146, pp. 690-697 (1977).
Braciale et al., Immunogenic recognition of influenza virus-infected cells, II Expression of Influenza A matrix protein . . . J. Exp. med. vol. 146, pp. 673-689 (1977).
Bucher et al., M Protein (M1) of influenza virus: antigenic analysis and intracellular localization with . . . J. Virol. vol. 63, pp. 3622-3633 (1989).
Bucher et al., Rapid detection of type A influenza viruses with monoclonal antibodies to the M protein (M1) by . . . J. CLin. Microbiol. vol. 29, pp. 2484-2488 (1991).
Cretescu et al., Formation of antibody to matrix protein in experimental human influenza A virus infections, Infect. Immun. vol. 22, pp. 322-327 (1978).
Epstein et al, DNA vaccine expressing conserved influenza virus protreins protective against H5N1 challenge . . . Emerg. Infect. Dis. vol. 8, pp. 796-801 (2002).
Gilbert et al., Potent CD8+ T-cell immunogenicity in humans of a novel heterosubtypic influenza A vaccine . . . Clin. Infect. Dis. vol. 52, pp. 1-7 (2011).
Goodman et al., A human multi-epitope recombinant vaccinia virus as a universal T cell vaccine candidate . . . PLoS ONE vol. 6, p. e25938 (2011).
Kaminski et al., Antibodies against conserved antigens provide opportunities for reform in influenza vaccine design, Front. Immunol. vol. 2, pp. 1-14 (2011).
Khan et al., Detection of antibodies to influenza virus M protein by an enzyme linked immunosorbent assay, J. Clin. Microbiol. vol. 16, pp. 813-820 (1982).
Khurana et al., Antigenic fingerprinting of H5N1 avian Influenza using convalescent sera and monoclonal antibodies . . . PLoS ONE vol. 6, p. e1000049 (2009).
Mostow et al., Application of the single radial diffusion test for assay of antibody to influenza type A viruses, J. Clin. Micorbiol. vol. 2, pp. 531-540 (1975).
Noton et al., Identification of the domains of the influenza A virus M1 matrix protein required for NP binding . . . J. Gen. Virol. vol. 88, pp. 2200-2290 (2007).
Plotnicky et al., The immunodominant influenza matrix T cell epitope recognized in human induces protection . . . Virol. vol. 309, pp. 320-329 (2003).
Powell et al., Examination of influenza specific T cell responses after influenza virus challenge in individuals . . . PLoS ONE vol. 8, p. e62778 (2013).
Roy et al., Influenza virus assembly: effect of influenza virus glycoprotein on the membrane association of M1 protein, J. Virol. vol. 74, pp. 8709-8719 (2000).
Schild, The influenza virus: antigenic composition and immune response, Postgrad. Med. J. vol. 55, pp. 87-97 (1979).
Shtykova et al., Structural analysis of influenza A virus matrix protein M1 and its self-assemblies at low pH, PLoS ONE vol. 8, p. e82431 (2013).
Sui et al., Cross-protection against influenza virus infection by intranasal administration of M1-based vaccine . . . Vaccine vol. 28, pp. 7690-7698.
Terajima et al., Influenza A virus protein 1-specific human CD8+ T-cell response induced in trivalent . . . J. Virol. vol. 82, pp. 9283-9287 (2008).
Virelizier et al., The role of humoral immunity in host defense against influenza A infection in mice, Postgrad. Med. Res. J. vol. 52, pp. 332-337 (1976).
Webster et al., Matrix protein from influenza A virus and its role in cross-protection in mice, Infect. Immun. vol. 17, pp. 561-566 (1977).
Wu et al., Systematic identification of H274Y compensatory mutations in influenza A virus neuraminidase . . . J. Virol. vol. 87, pp. 1193-1199 (2013).
Wu et al., High-throughput profiling of influenza A virus hemmagglutinin gene at single-nucleotide resolution, Nature Scientific Rep. vol. 4, pp. 4942 (2014).

* cited by examiner (-) Ctrl. 1.5 ug/ml 15 ug/ml

Virus Ctrl. 1.5 ug/ml 15 ug/ml

INFLUENZA VACCINE AND THERAPY

FIELD OF THE INVENTION

This invention relates to M1 polypeptides, vaccines containing the M1 polypeptides, antibodies that bind to the M1 polypeptides, and influenza therapies using the antibodies. The antibodies and polypeptides of the invention can also be used in diagnostics.

BACKGROUND OF THE INVENTION

Influenza is an acute, contagious respiratory disease caused by influenza viruses that are spread through respiratory droplet transmission. Uncomplicated influenza is characterized by the abrupt onset of constitutional and respiratory symptoms that usually resolve within a week. In certain persons, influenza can aggravate existing medical conditions and lead to life-threatening complications. Influenza viruses are one of the most ubiquitous viruses in the world, infecting humans, canines, birds, bats and livestock. Influenza has a significant impact on the elderly and on the very young. Influenza results in an economic burden, morbidity and even mortality, which are significant.

Influenza viruses are enveloped, negative-sense, RNA viruses with a segmented genome belonging to the Orthomyxoviridae family. They are classified on the basis of their core proteins into three distinct types: A, B, and C (Cox N J, Fukuda K. Influenza. Infect. Dis. Clin. North Am. 1998; 12:27-38, which is hereby incorporated by reference in its entirety). Influenza A viruses can infect a range of mammalian and avian species, whereas types B (host range humans and seals) and C are essentially restricted to humans. Influenza A and B viruses are mainly responsible for human disease with type A being the most pathogenic. The main antigenic determinants of influenza A and B viruses are two surface glycoproteins: neuraminidase (NA) and hemagglutinin (HA), both capable of eliciting immune response in human beings. HA is involved in receptor binding and membrane fusion. NA facilitates cleavage of virus progeny from infected cells, prevents viral aggregation, and aids movement through the mucosal respiratory-tract epithelium.

Three types of influenza virus (A, B and C) are currently known, the type A viruses being responsible for animal and human conditions while the type B and type C viruses are especially pathogenic for humans. The type A viruses are subdivided into subtypes according to the antigenic structure of hemagglutinin (HA) and of neuraminidase (NA), which are the principal glycoproteins of the viral envelope. Eighteen subtypes of HA (H1 to H18) and 9 subtypes of NA (N1 to N11) stand out. The subtype of a type A virus is therefore defined by the HA subtype and the NA subtype which are present in the viral envelope. Wild birds and bats constitute the reservoir of all influenza A subtypes. Certain subtypes of influenza virus type A endemically or epidemically (annual epidemics) infect domestic birds (various subtypes including H5N1 and H9N2), horses (principally H3N8), pigs (principally H1N1, H3N2 and H1N2) and also humans (principally H1N1 and H3N2). Dogs, cats and other wild species can also occasionally be infected with certain subtypes (H3N8 and H5N1 in dogs; H5N1 in cats).

Interpandemic influenza vaccines are prepared from virus that is grown in fertile hens' eggs and are either inactivated or live attenuated influenza vaccines. Inactivated influenza vaccines are composed of three possible forms of antigen preparation: inactivated whole virus, sub-virions where purified virus particles are disrupted with detergents or other reagents to solubilize the lipid envelope (so-called "split" vaccine) or purified HA and NA (subunit vaccine). These inactivated vaccines are currently given intramuscularly (i.m.), subcutaneously (s.c), or intranasally (i.n.). In accordance with World Health Organization (WHO) recommendations, seasonal influenza vaccines usually contain 45 μg of HA antigen from three co-circulating human strains (as measured by single radial immunodiffusion (SRD) (J. M. Wood et al.: An improved single radial immunodiffusion technique for the assay of influenza hemagglutinin antigen: adaptation for potency determination of inactivated whole virus and subunit vaccines. J. Biol. Stand. 5 (1977) 237-247; J. M. Wood et al., International collaborative study of single radial diffusion and immunoelectrophoresis techniques for the assay of hemagglutinin antigen of influenza virus. J. Biol. Stand. 9 (1981) 317-330), both of which are incorporated by reference in their entirety). They generally contain antigens derived from two influenza A virus strains and one influenza B strain (e.g. H1N1, H3N2 and B). A standard 0.5 ml injectable dose in most cases contains (at least) 15 μg of hemagglutinin antigen component from each strain. Vaccination plays a critical role in controlling annual influenza epidemics. Furthermore, during a pandemic, antiviral drugs may not be sufficient or effective to cover needs and the number of individuals at risk of influenza will be greater than in interpandemic periods. The development of a long lasting, broadly protective vaccine with the potential to be produced in large amounts and with efficient distribution and administration potential is an object of the invention.

Influenza virus infects millions each year, leading to over 200,000 hospitalizations and 20,000 deaths in the US. In addition, lethal strains of influenza arise on occasion (e.g., Spanish flu of 1918), with few effective means of treatment. Seasonal influenza vaccines afford some protection, provided that causative strains have not changed from the time of the vaccine formulation. High variability in the surface-expressed viral proteins of hemagglutinin and neuraminidase mandates yearly reformulation. The population should be re-immunized every year for effective protection. This necessity means that the cost of production is high and availability depends on the titer for each viral component of the vaccine.

Recombinant cell culture methods of antigen production rather than chicken eggs have now been employed and two vaccine products have recently been FDA approved. Flucelvax is a recombinant virus preparation (3 inactivated viruses) made by mammalian cell culture. Flubloc® is a recombinant HA vaccine (3 different HA proteins) made by insect cell culture. These products seek to solve problems of vaccine supply but do not address the issues of antigenic drift that is associated with HA based vaccines.

It is an object of this invention to overcome the need and cost for yearly influenza vaccine development by providing a new influenza vaccine that will maintain potency from year to year. It is also an object of the invention to provide an influenza vaccine that will provide protection against new influenza strains. It is a further object of the invention to provide an influenza therapy for treating individuals already infected with influenza, or for prophylactic treatment of individuals.

It is also an object of the invention to reduce the severity of an influenza infection in an infected patient, and/or reduce the duration of flu symptoms in a patient infected with influenza using a composition comprising an antibody or antibody fragment that binds to an M1 polypeptide.

SUMMARY OF THE INVENTION

The invention relates to polypeptides corresponding to a portion of an M1 protein of influenza. These polypeptides include M1 sequences from the C-terminal region of the M1 protein. These polypeptides also include sequences of the M1 protein that are exposed on the surface of influenza virus. At least portions of these surface exposed polypeptide sequences are capable of interacting with neutralizing antibodies and/or interacting with immune cells. In an embodiment, the C-terminal portion of the M1 polypeptide sequence that is surface exposed on influenza virus is the target for immune protection. In an embodiment, the polypeptides are within the span of amino acid residues 215 to 252 of the C-terminal portion of the M1 protein. In an embodiment the polypeptides are within the span of amino acid residues 215 to 241 of the M1 protein. In another embodiment, the M1 polypeptides are within the span of amino acid residues 220-238 of the M1 protein. In an embodiment, the M1 polypeptides span residues 220-242, 220-252, 223-242, or 223-252 of the M1 protein. In an embodiment, the M1 polypeptide comprises 7-37 contiguous amino acids of the M1 polypeptide found in the span of residues 215-252 of the M1 protein. In an embodiment, the M1 polypeptides comprise at least 15-50 amino acids. In an embodiment, the M1 polypeptides comprise 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, and/or 50 amino acids. In an embodiment, the M1 polypeptides of the invention include polypeptides that have 70%, 80%, 90%, 95%, and 99% sequence homology with any of the above M1 polypeptides.

In an embodiment, the M1 polypeptides comprise 7-120 contiguous amino acids of the M1 polypeptide found in the span of residues 131-252 of the M1 protein. In an embodiment, the M1 polypeptides comprise 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, and/or 122 amino acids. In an embodiment, the M1 polypeptides comprise 7-122 amino acids of the M1 polypeptide found in the span of residues 131-252 of the M1 protein. In this embodiment, not all of the amino acids in the polypeptide need to be contiguous in the M1 polypeptide span of residues 131-252 of the M1 protein. In an embodiment, the M1 polypeptides of the invention include polypeptides that have 70%, 80%, 90%, 95%, and 99% sequence identity with any of the M1 polypeptides for the span of residues from 131-252.

In an embodiment, the invention relates to nucleic acids encoding the M1 polypeptides described above. In an embodiment, the nucleic acids of the invention include nucleic acids that hybridize under stringent hybridization conditions to a nucleic acid encoding one of the M1 polypeptides of the invention. In an embodiment, the M1 polypeptides of the invention include the polypeptides encoded by nucleic acids that hybridize under stringent hybridization conditions to nucleic acids encoding the M1 polypeptides describe above. In an embodiment, the nucleic acids of the invention encode a polypeptide of one of SEQ ID NOS: 1-7, or are a nucleic acid that hybridizes under stringent hybridization conditions to a nucleic acid encoding one of SEQ ID NOS: 1-7. In an embodiment, the nucleic acids of the invention encode a polypeptide that has 70%, 80%, 90%, 95%, and 99% sequence identity with one of SEQ ID NOS: 1-7. In an embodiment, the nucleic acids of the invention encode a polypeptide of one of SEQ ID NOS: 8-80, or are a nucleic acid that hybridizes under stringent hybridization conditions to a nucleic acid encoding one of SEQ ID NOS: 8-80. In an embodiment, the nucleic acids of the invention encode a polypeptide that has 70%, 80%, 90%, 95%, and 99% sequence identity with SEQ ID NOS: 8-80.

In an embodiment, M1 polypeptides are used to produce a protective/therapeutic immune response in an organism susceptible to influenza. In an embodiment, the organism is a human, a canine, or a commercially valuable livestock. In an embodiment, the organism is a human. In an embodiment, the M1 polypeptide composition is capable of inducing at least one of: a humoral immune response, a T-cell immune response such as a CD4 T-cell immune response and a B cell memory response against said M1 polypeptide.

The invention also relates to antibodies specific to the M1 polypeptides of the invention. In an embodiment, the anti-M1 polypeptide antibodies are used for the treatment and or prevention of influenza in organisms that are or may be infected by influenza virus. In an embodiment, the organism is a human, a canine, or a commercially valuable livestock. In an embodiment, the organism is a human. In an embodiment, treatment of the organism with an anti-M1 polypeptide antibody or antibodies reduces the severity of influenza symptoms and/or the time period of influenza symptoms.

In an embodiment, the anti-M1 polypeptide antibodies are used in treatment of organisms to prevent infection with influenza, or to ameliorate a future infection with influenza. In an embodiment, the organism is a human, a canine, or a commercially valuable livestock. In an embodiment, the organism is a human. In an embodiment, the anti-M1 polypeptide antibodies are used prophylactically to generate passive immunity in an organism. In an embodiment, the anti-M1 antibody is 2B-B10-G9, or an antibody that binds to the epitope of 2B-B10-G9, or a humaneered, humanized, chimerized, or otherwise genetically engineered variant of 2B-B10-G9 or antibody that binds to the epitope of 2B-B10-G9.

In an embodiment, the anti-M1 polypeptide antibodies have a half-life of 1-4 weeks or more in an organism. In an embodiment, the anti-M1 polypeptide antibodies have a half-life of 2 weeks in an organism. In an embodiment, the passive immunity generated in an organism from the anti-M1 polypeptide antibody lasts for at least 2-3 half-lives. In an embodiment, the passive immunity generated in an organism from the anti-M1 polypeptide antibody lasts for 1-7 weeks, or 2, 3, 4, 5 or 6 months.

In an embodiment, the anti-M1 polypeptide antibodies are engineered to have a half-life of 4-12 weeks. In an embodiment, the anti-M1 polypeptide antibodies are chimeric, humanized, or Humaneered®, or are human antibodies. In an embodiment, the anti-M1 polypeptide antibodies are conjugated with molecules that increase half-life in an organism. In an embodiment, the anti-M1 polypeptide antibodies are conjugated with polyethylene glycol or another suitable polymer or molecule to increase the half-life of the antibody.

DETAILED DESCRIPTION OF THE INVENTION

Figure 1:
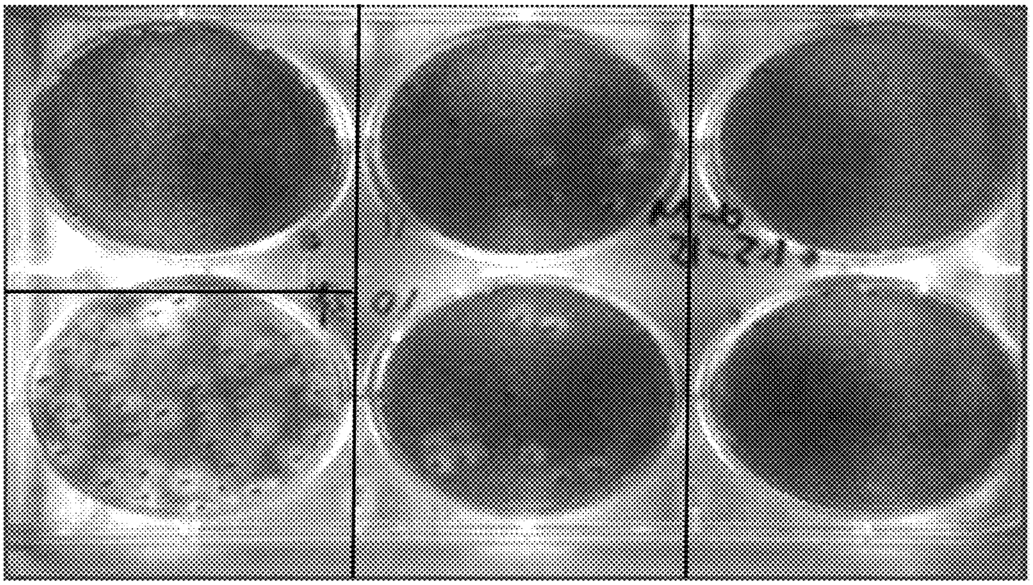
FIG. 1 shows a plaque inhibition assay of influenza virus strain PR/8 by monoclonal antibody 2B-B10-G9.

The invention is illustrated by way of example and not by way of limitation.

Definitions

As used herein, an "antibody" refers to a protein functionally defined as a binding protein and structurally defined as comprising an amino acid sequence that is recognized as being derived from the framework region of an immunoglobulin encoding gene. An antibody can consist of one or more polypeptides substantially encoded by immunoglobulin genes or fragments of immunoglobulin genes. The recognized immunoglobulin genes include the kappa, lambda, alpha, gamma, delta, epsilon and mu constant region genes, as well as myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

A typical gamma immunoglobulin (antibody) structural unit is known to comprise a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

Antibodies exist as intact immunoglobulins or as a number of well-characterized fragments. Thus, for example, pepsin digests an antibody below the disulfide linkages in the hinge region to produce $F(ab)'_2$, a dimer of Fab' which itself is naturally a light chain joined to VH-CH1-Hinge by a disulfide bond. The $F(ab)'_2$ may be reduced under mild conditions to break the disulfide linkage/s in the hinge region thereby converting the $(Fab')_2$ dimer into an Fab' monomer. The Fab' monomer is essentially a Fab with part of the hinge region (see, Fundamental Immunology, W. E. Paul, ed., Raven Press, N.Y. (1993), for a more detailed description of other antibody fragments). While various antibody fragments are defined in terms of the digestion of an intact antibody, one of skill in the art will appreciate that fragments can be synthesized de novo either chemically or by utilizing recombinant DNA methods. Thus, the term antibody, as used herein also includes antibody fragments either produced by the modification of whole antibodies or synthesized using recombinant DNA methodologies. Preferred antibodies include $V_H$-$V_L$ dimers, including single chain antibodies (antibodies that exist as a single polypeptide chain), such as single chain Fv antibodies (sFv or scFv) in which a variable heavy and a variable light region are joined together (directly or through a peptide linker) to form a continuous polypeptide. The single chain Fv antibody is a covalently linked $V_H$-$V_L$ heterodimer which may be expressed from a nucleic acid including $V_H$- and $V_L$-encoding sequences either joined directly or joined by a peptide-encoding linker (e.g., Huston, et al. Proc. Nat. Acad. Sci. USA, 85:5879-5883, 1988, which is hereby incorporated by reference in its entirety). While the $V_H$ and $V_L$ are connected to each as a single polypeptide chain, the $V_H$ and $V_L$ domains associate non-covalently. Alternatively, the antibody can be another fragment. Other fragments can also be generated, including using recombinant techniques. For example Fab molecules can be displayed on phage if one of the chains (heavy or light) is fused to g3 capsid protein and the complementary chain exported to the periplasm as a soluble molecule. The two chains can be encoded on the same or on different replicons; the two antibody chains in each Fab molecule assemble post-translationally and the dimer is incorporated into the phage particle via linkage to one of the chains of g3p (see, e.g., U.S. Pat. No. 5,733,743, which is hereby incorporated by reference in its entirety). The scFv antibodies and a number of other structures converting the naturally aggregated, but chemically separated light and heavy polypeptide chains from an antibody V region into a molecule that folds into a three dimensional structure substantially similar to the structure of an antigen-binding site are known to those of skill in the art (see e.g., U.S. Pat. Nos. 5,091,513, 5,132,405, and 4,956,778, all of which are hereby incorporated by reference in their entirety). Particularly preferred antibodies include all those that have been displayed on phage or generated by recombinant technology using vectors where the chains are secreted as soluble proteins, e.g., scFv, Fv, Fab, $(Fab')_2$. Antibodies can also include diabodies and minibodies.

Antibodies of the invention also include heavy chain dimers, such as antibodies from camelids. Since the $V_H$ region of a heavy chain dimer IgG in a camelid does not have to make hydrophobic interactions with a light chain, the region in the heavy chain that normally contacts a light chain is changed to hydrophilic amino acid residues in a camelid. $V_H$ domains of heavy-chain dimer IgGs are called $V_{HH}$ domains.

In camelids, the diversity of antibody repertoire is determined by the complementary determining regions (CDR) 1, 2, and 3 in the $V_H$ or $V_{HH}$ regions. The CDR3 in the camel $V_{HH}$ region is characterized by its relatively long length averaging 16 amino acids (Muyldermans et al., 1994, Protein Engineering 7(9): 1129, which is hereby incorporated by reference in its entirety). This is in contrast to CDR3 regions of antibodies of many other species. For example, the CDR3 of mouse $V_H$ has an average of 9 amino acids.

Libraries of camelid-derived antibody variable regions, which maintain the in vivo diversity of the variable regions of a camelid, can be made by, for example, the methods disclosed in U.S. Patent Application publication No. US20050037421, published Feb. 17, 2005, which is hereby incorporated by reference in its entirety.

Antibody-dependent cell-mediated cytotoxicity (ADCC) is an important mechanism of action of antibodies. ADCC may be enhanced by several methods, many of which involve an end product antibody with improved Fc-receptor binding. Amino acid substitutions in the antibody Fc region have been shown to increase Fc binding affinity for FcγRIIIa receptor on NK cells (Natsume et al., Drug Design, Development and Therapy, 2009, vol. 3, pp. 7-16, which is hereby incorporated by reference in its entirety) and to improve ADCC activity. Another method for improving ADCC is to change the sugar composition of the antibody glycosylation. This is done by making antibodies that lack fucose residues, which is to say, an 'a-fucosylated' or 'de-fucosylated' antibody. One method involves changing/modifying the glycosylation site of the antibody so that fucose cannot be added to the antibody (U.S. Pat. No. 6,194,551, Feb. 27, 2001). Another method is to remove a pre-existing fucose on an antibody by, for example, enzymatic degradation or removal of the fucose by any other means. Another method involves the genetic engineering of the host expression system so that fucose cannot be transferred to or added to the antibody, for example by suppression or deletion of fucosyl transferase activity (U.S. Patent Application publication Nos.:

20070134759. Jun. 14, 2007; and 20080166756, Jul. 10, 2008, both of which are hereby incorporated by reference in their entirety).

As used herein, the term “antigen” refers to substances that are capable, under appropriate conditions, of inducing a specific immune response and of reacting with the products of that response, such as, with specific antibodies or specifically sensitized T-lymphocytes, or both. Antigens may be soluble substances, such as toxins and foreign proteins, or particulates, such as bacteria and tissue cells; however, only the portion of the protein or polysaccharide molecule known as the antigenic determinant (epitopes) combines with the antibody or a specific receptor on a lymphocyte. More broadly, the term “antigen” may be used to refer to any substance to which an antibody binds, or for which antibodies are desired, regardless of whether the substance is immunogenic. For such antigens, antibodies may be identified by recombinant methods, independently of any immune response.

As used herein, the term “binding specificity” of an antibody refers to the identity of the antigen to which the antibody binds, preferably to the identity of the epitope to which the antibody binds.

As used herein, the term “chimeric polynucleotide” means that the polynucleotide comprises regions which are wild-type and regions which are mutated. It may also mean that the polynucleotide comprises wild-type regions from one polynucleotide and wild-type regions from another related polynucleotide.

As used herein, the term “complementarity-determining region” or “CDR” refer to the art-recognized term as exemplified by Kabat and Chothia. CDRs are also generally known as hypervariable regions or hypervariable loops (Chothia and Lesk (1987) J Mol. Biol. 196: 901; Chothia et al. (1989) Nature 342: 877; E. A. Kabat et al., Sequences of Proteins of Immunological Interest (National Institutes of Health, Bethesda, Md.) (1987); and Tramontano et al. (1990) J Mol. Biol. 215: 175, all of which are hereby incorporated by reference in their entirety). “Framework region” or “FR” refers to the region of the V domain that flank the CDRs. The positions of the CDRs and framework regions can be determined using various well known definitions in the art, e.g., Kabat, Chothia, international ImMunoGeneTics database (IMGT), and AbM (see, e.g., Johnson et al., supra; Chothia & Lesk, 1987, Canonical structures for the hypervariable regions of immunoglobulins. J. Mol. Biol. 196, 901-917; Chothia C. et al., 1989, Conformations of immunoglobulin hypervariable regions. Nature 342, 877-883; Chothia C. et al., 1992, structural repertoire of the human VH segments J. Mol. Biol. 227, 799-817; Al-Lazikani et al., J. Mol. Biol 1997, 273(4)). Definitions of antigen combining sites are also described in the following: Ruiz et al., IMGT, the international ImMunoGeneTics database. Nucleic Acids Res., 28, 219-221 (2000); and Lefranc, M.-P. IMGT, the international ImMunoGeneTics database. Nucleic Acids Res. January 1; 29(1):207-9 (2001); MacCallum et al, Antibody-antigen interactions: Contact analysis and binding site topography, J. Mol. Biol., 262 (5), 732-745 (1996); and Martin et al, Proc. Natl Acad. Sci. USA, 86, 9268-9272 (1989); Martin, et al, Methods Enzymol., 203, 121-153, (1991); Pedersen et al, Immunomethods, 1, 126, (1992); and Rees et al, In Sternberg M. J. E. (ed.), Protein Structure Prediction. Oxford University Press, Oxford, 141-172 1996, all of which are hereby incorporated by reference in their entirety).

As used herein, an “effective amount” refers to an amount of a compound, formulation, material, or composition, as described herein effective to achieve a particular biological result.

As used herein, the term “epitope” refers to the site on an antigen or hapten to which specific B cells and/or T cells respond. The term is also used interchangeably with “antigenic determinant” or “antigenic determinant site”. Epitopes include that portion of an antigen or other macromolecule capable of forming a binding interaction that interacts with the variable region binding pocket of an antibody.

As used herein, the term “hapten” is a small molecule that, when attached to a larger carrier such as a protein, can elicit an immune response in an organism, e.g., such as the production of antibodies that bind specifically to it (in either the free or combined state). A “hapten” is able to bind to a preformed antibody, but may fail to stimulate antibody generation on its own. In the context of this invention, the term “hapten” includes modified amino acids, either naturally occurring or non-naturally occurring. Thus, for example, the term “hapten” includes naturally occurring modified amino acids such as phosphotyrosine, phosphothreonine, phosphoserine, or sulphated residues such as sulphated tyrosine (sulphotyrosine), sulphated serine (sulphoserine), or sulphated threonine (sulphothreonine); and also includes non-naturally occurring modified amino acids such as p-nitro-phenylalanine.

As used herein, the term “heterologous” when used with reference to portions of a polynucleotide indicates that the nucleic acid comprises two or more subsequences that are not normally found in the same relationship to each other in nature. For instance, the nucleic acid is typically recombinantly produced, having two or more sequences, e.g., from unrelated genes arranged to make a new functional nucleic acid. Similarly, a “heterologous” polypeptide or protein refers to two or more subsequences that are not found in the same relationship to each other in nature.

As used herein, the term “host cell” refers to a prokaryotic or eukaryotic cell into which the vectors of the invention may be introduced, expressed and/or propagated. A microbial host cell is a cell of a prokaryotic or eukaryotic micro-organism, including bacteria, yeasts, microscopic fungi and microscopic phases in the life-cycle of fungi and slime molds. Typical prokaryotic host cells include various strains of *E. coli*. Typical eukaryotic host cells are yeast or filamentous fungi, or mammalian cells, such as Chinese hamster ovary cells, murine NIH 3T3 fibroblasts, human embryonic kidney 193 cells, or rodent myeloma or hybridoma cells.

As used herein, the term “immunological response” to a composition or vaccine is the development in the host of a cellular and/or antibody-mediated immune response to a composition or vaccine of interest. Usually, an “immunological response” includes but is not limited to one or more of the following effects: the production of antibodies, B cells, helper T cells, and/or cytotoxic T cells, directed specifically to an antigen or antigens included in the composition or vaccine of interest. Preferably, the host will display either a therapeutic or protective immunological response such that resistance to new infection will be enhanced and/or the clinical severity of the disease reduced. Such protection will be demonstrated by either a reduction or lack of symptoms normally displayed by an infected host, a quicker recovery time and/or a lowered viral titer in the infected host.

As used herein, the term “isolated” refers to a nucleic acid or polypeptide separated not only from other nucleic acids or polypeptides that are present in the natural source of the nucleic acid or polypeptide, but also from polypeptides, and preferably refers to a nucleic acid or polypeptide found in the presence of (if anything) only a solvent, buffer, ion, or other component normally present in a solution of the same. The terms "isolated" and "purified" do not encompass nucleic acids or polypeptides present in their natural source.

As used herein, the term "mammal" refers to warm-blooded vertebrate animals all of which possess hair and suckle their young.

As used herein, the term "multivalent", means that the vaccine contains M1 polypeptides from at least two influenza isolates having different amino acid sequences, or that the vaccine contains an M1 polypeptide from one influenza isolate and an antigenic preparation from another influenza isolate different from the M1 polypeptide isolate.

As used herein, the term "naturally occurring" means that the components are encoded by a single gene that was not altered by recombinant means and that pre-exists in an organism, e.g., in an antibody library that was created from naive cells or cells that were exposed to an antigen.

As used herein, "percentage of sequence identity" and "percentage homology" are used interchangeably herein to refer to comparisons among polynucleotides or polypeptides, and are determined by comparing two optimally aligned sequences over a comparison window, where the portion of the polynucleotide or polypeptide sequence in the comparison window may comprise additions or deletions (i.e., gaps) as compared to the reference sequence for optimal alignment of the two sequences. The percentage may be calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity. Alternatively, the percentage may be calculated by determining the number of positions at which either the identical nucleic acid base or amino acid residue occurs in both sequences or a nucleic acid base or amino acid residue is aligned with a gap to yield the number of matched positions, dividing the number of matched positions by the total number of positions in the window of comparison and multiplying the result by 100 to yield the percentage of sequence identity. Those of skill in the art appreciate that there are many established algorithms available to align two sequences. Optimal alignment of sequences for comparison can be conducted, e.g., by the local homology algorithm of Smith and Waterman, *Adv Appl Math.* 2:482, 1981; by the homology alignment algorithm of Needleman and Wunsch, *J Mot Biol.* 48:443, 1970; by the search for similarity method of Pearson and Lipman, *Proc Natl Acad Sci. USA* 85:2444, 1988; by computerized implementations of these algorithms (GAP, BESTFIT, FASTA, and TFASTA in the GCG Wisconsin Software Package), or by visual inspection (see generally, *Current Protocols in Molecular Biology*, F. M. Ausubel et al., eds., Greene Publishing Associates, Inc. and John Wiley & Sons, Inc., (1995 Supplement). Examples of algorithms that are suitable for determining percent sequence identity and sequence similarity are the BLAST and BLAST 2.0 algorithms, which are described in Altschul et al., *J Mol. Biol.* 215:403-410, 1990; and Altschul et al., *Nucleic Acids Res.* 25(17):3389-3402, 1977; respectively. Software for performing BLAST analyses is publicly available through the National Center for Biotechnology Information website. BLAST for nucleotide sequences can use the BLASTN program with default parameters, e.g., a wordlength (W) of 11, an expectation (E) of 10, M=5, N=−4, and a comparison of both strands. BLAST for amino acid sequences can use the BLASTP program with default parameters, e.g., a wordlength (W) of 3, an expectation (E) of 10, and the BLOSUM62 scoring matrix (see Henikoff and Henikoff, *Proc Natl Acad Sci. USA* 89:10915, 1989). Exemplary determination of sequence alignment and % sequence identity can also employ the BESTFIT or GAP programs in the GCG Wisconsin Software package (Accelrys, Madison Wis.), using default parameters provided.

As used herein, the terms "protein", "peptide", "polypeptide" and "polypeptide fragment" are used interchangeably herein to refer to polymers of amino acid residues of any length. The polymer can be linear or branched, it may comprise modified amino acids or amino acid analogs, and it may be interrupted by chemical moieties other than amino acids. The terms also encompass an amino acid polymer that has been modified naturally or by intervention; for example disulfide bond formation, glycosylation, lipidation, acetylation, phosphorylation, or any other manipulation or modification, such as conjugation with a labeling or bioactive component.

As used herein, the term "purified" means that the indicated nucleic acid or polypeptide is present in the substantial absence of other biological macromolecules, e.g., polynucleotides, proteins, and the like. In one embodiment, the polynucleotide or polypeptide is purified such that it constitutes at least 95% by weight, more preferably at least 99.8% by weight, of the indicated biological macromolecules present (but water, buffers, and other small molecules, especially molecules having a molecular weight of less than 1000 daltons, can be present).

As used herein, the term "recombinant nucleic acid" refers to a nucleic acid in a form not normally found in nature. That is, a recombinant nucleic acid is flanked by a nucleotide sequence not naturally flanking the nucleic acid or has a sequence not normally found in nature. Recombinant nucleic acids can be originally formed in vitro by the manipulation of nucleic acid by restriction endonucleases, or alternatively using such techniques as polymerase chain reaction. It is understood that once a recombinant nucleic acid is made and reintroduced into a host cell or organism, it will replicate non-recombinantly, i.e., using the in vivo cellular machinery of the host cell rather than in vitro manipulations; however, such nucleic acids, once produced recombinantly, although subsequently replicated non-recombinantly, are still considered recombinant for the purposes of the invention.

As used herein, the term "recombinant polypeptide" refers to a polypeptide expressed from a recombinant nucleic acid, or a polypeptide that is chemically synthesized in vitro.

As used herein, the term "recombinant variant" refers to any polypeptide differing from naturally occurring polypeptides by amino acid insertions, deletions, and substitutions, created using recombinant DNA techniques. Guidance in determining which amino acid residues may be replaced, added, or deleted without abolishing activities of interest, such as enzymatic or binding activities, may be found by comparing the sequence of the particular polypeptide with that of homologous peptides and minimizing the number of amino acid sequence changes made in regions of high homology.

As used herein, the terms "repertoire" or "library" refers to a library of genes encoding antibodies or antibody fragments such as Fab, scFv, Fd, LC, $V_H$, or $V_L$, or a subfragment of a variable region, e.g., an exchange cassette, that is obtained from a natural ensemble, or "repertoire", of antibody genes present, e.g., in human donors, and obtained primarily from the cells of peripheral blood and spleen. In some embodiments, the human donors are "non-immune", i.e., not presenting with symptoms of infection. In the current invention, a library or repertoire often comprises members that are exchange cassettes of a given portion of a V region. The term Fd means that portion of the heavy chain that is included in the Fab fragment.

As used herein, "stringent hybridization conditions" refers to hybridizing in 50% formamide at 5×SSC at a temperature of 42° C. and washing the filters in 0.2×SSC at 60° C. (1×SSC is 0.15M NaCl, 0.015M sodium citrate.) Stringent hybridization conditions also encompasses low ionic strength and high temperature for washing, for example 0.015 M sodium chloride/0.0015 M sodium citrate/0.1% sodium dodecyl sulfate at 50° C.; hybridization with a denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; or 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 μg/ml), 0.1% SDS, and 10% dextran sulfate at 42° C., with washes at 42° C. in 0.2×SSC (sodium chloride/sodium citrate) and 50% formamide at 55° C., followed by a high-stringency wash consisting of 0.1×SSC containing EDTA at 55° C.

As used herein, "substantial identity" refers to a polynucleotide or polypeptide sequence that has at least 80 percent sequence identity, at least 85 percent identity and 89 to 95 percent sequence identity. Substantial identity also encompasses at least 99 percent sequence identity as compared to a reference sequence over a comparison window of at least 20 residue positions or a window of at least 30-50 residues, wherein the percentage of sequence identity is calculated by comparing the reference sequence to a sequence that includes deletions or additions or substitutions over the window of comparison. In specific embodiments applied to polypeptides, the term "substantial identity" means that two polypeptide sequences, when optimally aligned, such as by the programs GAP or BESTFIT using standard parameters, i.e., default parameters, share at least 80 percent sequence identity, preferably at least 89 percent sequence identity, at least 95 percent sequence identity or more (e.g., 99 percent sequence identity).

Preferably, amino acid "substitutions" are the result of replacing one amino acid with another amino acid having similar structural and/or chemical properties, i.e., conservative amino acid replacements. Amino acid substitutions may be made on the basis of similarity in polarity, charge, solubility, hydrophobicity, hydrophilicity, and/or the amphipathic nature of the residues involved. For example, nonpolar (hydrophobic) amino acids include alanine, leucine, isoleucine, valine, proline, phenylalanine, tryptophan, and methionine; polar neutral amino acids include glycine, serine, threonine, cysteine, tyrosine, asparagine, and glutamine; positively charged (basic) amino acids include arginine, lysine, and histidine; and negatively charged (acidic) amino acids include aspartic acid and glutamic acid.

As used herein, the term "synthetic antibody library" refers to a library of genes encoding one or more antibodies or antibody fragments such as Fab, scFv, Fd, LC, $V_H$, or $V_L$, or a subfragment of a variable region, e.g., an exchange cassette, in which one or more of the complementarity-determining regions (CDR) has been partially or fully altered, e.g., by oligonucleotide-directed mutagenesis. "Randomized" means that part or all of the sequence encoding the CDR has been replaced by sequence randomly encoding all twenty amino acids or some subset of the amino acids.

As used herein the term "variant" refers to any polypeptide differing from naturally occurring polypeptides or polynucleotides by amino acid or nucleotide insertions, deletions, and substitutions which are made through laboratory techniques.

The singular terms "a", "an", and "the" include plural referents unless context clearly indicates otherwise. Similarly, the word "or" is intended to include "and" unless the context clearly indicates otherwise. Numerical limitations given with respect to concentrations or levels of a substance, such as an antigen, are intended to be approximate. Thus, where a concentration is indicated to be at least (for example) 200 μg, it is intended that the concentration be understood to be at least approximately "about" or "about" 200 μg.

M1 Polypeptides

The invention relates to a method of inducing an immune response, in particular a primary immune response, against influenza virus in a human individual or population, said method comprising the administration of an M1 polypeptide composition comprising an M1 polypeptide of the invention or antigenic preparation thereof. In an embodiment, the immune response is obtained in a naïve, immuno-compromised, or previously infected human individual or population.

M-protein, or matrix protein, M1 is a major structural component of the influenza virus (Zhang et al., 2012, Dissection of influenza A Virus M1 Protein: pH-Dependent Oligomerization of N-Terminal Domain and Dimerization of C-Terminal Domain, PLoS ONE 7(5): e37786. doi: 10.1371/journal.pone.0037786, which is hereby incorporated by reference in its entirety). The M gene encodes two proteins, M1 and M2. M1 protein is highly conserved across all type A subtypes of influenza viruses, which is the more clinically relevant influenza subtype. A C-terminal portion of the M1 protein is extracellularly exposed on the virus and, considering its high sequence conservation, represents an excellent target for a universal subunit vaccine immunogen.

In an embodiment, the target M1 polypeptides span amino acid residues in the C-terminus of the M1 protein, specifically amino acid residues 215-252, or 215-240, or 220-238, or 220-242, or 220-252, or 223-242, or 223-252 of the M1 protein. In an embodiment, the M1 polypeptide is GTHPSSSAGLKNDLLENLQ (SEQ ID NO: 1), GTHPSSSAGLKNDLLENLQAYQK (SEQ ID NO: 2), GTHPSSSAGLKNDLLENLQAYQKRMGVQMQRFK (SEQ ID NO: 3), PSSSAGLKNDLLENLQAYQK (SEQ ID NO: 4), PSSSAGLKNDLLENLQAYQKRMGVQMQRFK (SEQ ID NO: 5), AMRTIGTHPSSSAGLKNDLLENLQAYQKRMGVQMQRFK (SEQ ID NO: 6), or a polypeptide consisting of contiguous amino acids from this sequence of 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37 and/or 38 amino acids, or IYNRMGAVTTEVAFGLVCATCEQIADSQHRSHRQMVTTTNPLIRHENRMVLASTTAKAMEQ MAGSSEQAAEAMEVASQARQMVQAMRTIGTHPSSSAGLKNDLLENLQAYQKRMGVQMQR FK (SEQ ID NO: 7), or a polypeptide consisting of amino acids from this sequence of 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, and/or 122 amino acids. In this embodiment, not all of the amino acids in the polypeptide need to be contiguous in the M1 polypeptide span of residues 131-252 of the M1 protein.

In an embodiment, the M1 polypeptides of the invention include naturally occurring strain variants, such as for example, A/Bangkok/163/2000 (GTHPSSSTGLKNDLLENLQ) (SEQ ID NO: 8) or (IYNRMGAVTTESAFGLICATCEQIADSQHKSHRQMVTTTNPLIRHENRMVLA STTAKAMEQMAGSSEQAAEAMEVASQARQMVQAMRAIGTHPSSSTGLKNDLLENLQAYQ KRMGVQMQRFK)(SEQ ID NO: 9); A/PR/8/34 (GTHPSSSAGLKNDLLENLQ) (SEQ ID NO: 10) or (IYNRMGAVTTEVAFGLVCATCEQIADSQHRSHRQMVTTTNPLIRHENRMV LASTTAKAMEQMAGS SEQAAEAMEVASQARQMVQAMRTIGTHPSSSAGLKNDLLENLQAY QKRMGVQMQRFK)(SEQ ID NO: 11); A/AA/Huston/1945 (GTHPSSSAGLKDDLLENLQ) (SEQ ID NO: 12) or (IYNRMGAVTTEVAFGLVCATCEQIADSQHRSHRQMVTTTNPLIRHENR MVLASTTAKAMEQMAGSSEQAAEAMEVASQARQMVQAMRTIGTHPSSSAGLKDDLLENL QAYQKRMGVQMQRFK)(SEQ ID NO: 13); A/Berlin/6/2006 (GTHPSSSTGLKNDLLDNLQ) (SEQ ID NO: 14) or (IYNRMGAVTTESAFGLICATCEQIADSQHKSHRQMVTTTNPLIRHENR MVLASTTAKAMEQMAGSSEQAAEAMEVANQARQMVQAMRAIGTHPSSST GLKNDLLDNL QAYQKRMGVQMQRFK)(SEQ ID NO: 15); A/Brandenburg/1/2006 (GTHPNSSTGLKNDLLENLQ) (SEQ ID NO: 16) or (IYNRMGAVTTESAFGLICATCEQIADSQ HKSHRQMVTTTNPLIRHENRMVLASTTAKAMEQMAGS SEQAAEAMEVASQARQMVQAMR AIGTHPNSSTGLKNDLLENLQAYQKRMGVQMQRFK) (SEQ ID NO: 17); A/Brevig Mission/1/1918 (GTHPSSSAGLKDDLIENLQ) (SEQ ID NO: 18) or (IYNRMGTVTTEVAFGLVCATCEQIADSQHRSHRQMVTTTNPLIRHENRMVLASTTAKAME QMAGSSEQAAEAMEVASQARQMVQAMRTIGTHPSSSAGLKDDLIENLQAYQKRMGVQMQ RFK) (SEQ ID NO: 19); A/Chile/8885/2001 (GTHPSSSTGLKDDLLENLQ) (SEQ ID NO: 20) or (IYNRMGAVTTESAFGLICATCEQIADSQHKSHRQMVTTTNPLIRHENRMVLASTTAKAMEQ MAGSSEQAAEAMEVANQARQMVQAMRAIGTHPSSSTGLKDDLLENLQAYQKRMGVQMQ RFK)(SEQ ID NO: 21); A/DaNang/DN311/2008 (GTHPSSSTGLRDDLLENLQ) (SEQ ID NO: 22) or (IYNRMGAVTTEVAFGLVCATCEQIADSQHRSHRQMVATTNPLIKHENRMVLASTTAK AMEQMAGSSEQAAEAMEIASQARQMVQAMRAIGTHPSSSTGLRDDLLENLQXYQKRMGV QMQRFK)(SEQ ID NO: 23); A/FLW/1951 (GTRPSSSAGLKDDLLENLQ) (SEQ ID NO: 24) or (IYNRMGAVTTEVAFGLVCATCEQIADSQHRSHRQMVTTTNPLIRHENRMVLASTTAKAME QMAGSSEQAAEAMEVASQARQMVQAMRAIGTRPSSSAGLKDDLLENLQAYQKRMGVQM QRFK) (SEQ ID NO: 25); A/FW/1/1950 (GTHPRSSAGLKDDLLENLQ) (SEQ ID NO: 26) or (IYNRMGAVTTEVAFGLVCATCEQIADSQHRSHRQMVTTTNPLIRHENRMVLASTTAKAME QMAGSSEQAAEAMEVASQARQMVQAMRAIGTHPRSSAGLKDDLLENLQAYQKRMGVQM QRFK)(SEQ ID NO: 27); A/Fiji/15899/83 (GTHPSSSAGLKNDLFENLQ) (SEQ ID NO: 28) or (IYNRMGAVTTESAFGLVCATCEQIADSQHKSHRQMVTTTNPLIRHENRMVLASTTAKAME QMAGSSEQAAEAMEVASQARQMVQAMRAIGTHPSSSAGLKNDLFENLQAYQKRMGVQM QRFK)(SEQ ID NO: 29); A/Fort Monmouth/1-MA/1947 (GTHPSSSAGLKDNLLENLQ) (SEQ ID NO: 30) or (IYNRMGAVATEVAFGLICATCEQIADAQHRSHRQMVTTTNPLIRHENRMVLAS TTAKAMEQMAGSSEQAAEAMEVASQARQMVQAMRAIGTHPSSSAGLK DNLLENLQAYQK RMGVQMQRFK)(SEQ ID NO: 31); A/Halloi/TX233/2008 (GTHPSSSTGLKSDLLENLQ) (SEQ ID NO: 32) or (IYNRMGAVTTESAFGLICATCEQIADSQHKSHRQMVTTTNPLIRHENRMVLA STTAKAMEQMAGSSEQAAEAMEVASQARQMVQAMRAIGTHPSSSTGLKSDLLENLQAYQK RMGVQMQRFK)(SEQ ID NO: 33); A/Iowa/CEID23/2005 (GTHPNSSTGLKDDLLENLQ) (SEQ ID NO: 34) or (IYNRMGTVTTEVAFGLVCATCEQIADSQHRSHRQMVTTTNPLIRHENRMV IASTTAKAMEQMAGSSEQASEAMEVASQARQMVQAMRTIGTHPNSST GLKDDLLENLQAY QKRMGVQMQRFK)(SEQ ID NO: 35); A/Malaysia/35164/2006 (GTHPSSSTGLKKDLLDNLQ) (SEQ ID NO: 36) or (IYNRMGAVTTESAFGLICATCEQIADSQHKSHRQMVTTTNPLIRHENR MVLASTTAKAMEQMAGSSEQAAEAMEVASQARQMVQAMRAIGTHPSSSTGLKKDLLDNL QAYQKRMGVQMQRFK)(SEQ ID NO: 37); A/Managua/4086.04/2008 (GTHPSSSNGLKNDLLENLQ) (SEQ ID NO: 38) or (IYNRMGAVTTESAFGLICATCEQIADSQ HKSHRQMVTTTNPLIRHENRMVLASTTAKAMEQMAGSSEQAAEAMEVASQARQMVQAMR AIGTHPSSSNGLKNDLLENLQAYQKRMGVQMQRFK) (SEQ ID NO: 39); A/Texas/VR06-0502/2007 (GTHPSSSTGLRNDLLENLQ) (SEQ ID NO: 40) or (IYNRMGAVTTESAFGLI CATCEQIADSQHKSHRQMVTTTNPLIRHENRMVLASTTAKAMEQMAGSSEQAAEAMEVAS QARQMVQAMRAIGTHPSSSTGLRNDLLENLQAYQKRMGVQMQRFK)(SEQ ID NO: 41); A/WSN/1933 (GTHPSSSAGLKSDLLENLQ) (SEQ ID NO: 42) or (IYNRMGAVTTEVAFGLV CATCEQIADSQHRSHRQMVTTTNPLIRHENRMVLASTTAKAMEQMAGSSEQAAEAMDIASQ ARQMVQAMRTIGTHPSSSAGLKSDLLENLQAYQKRMGVQMQRFK)(SEQ ID NO: 43); A/Colorado/18/2011 (GTHPSSSAGLRDDLLENLQ) (SEQ ID NO: 44) or (IYNRMGTVTTEAAFGLVCATCEQIADSQHRSHRQMATTTNPLIRHENRMVLASTTAKAME QMAGSSEQAAEAMEVANQTRQMVHAMRTIGTHPSSSAGLRDDLLENLQAYQKRMGVQMQ RFK)(SEQ ID NO: 45); A/Kentucky/04/2010 (GTHPNSSAGLKDDLLENLQ) (SEQ ID NO: 46) or (IYNRMGTVTTEAAFGLVCATCEQIADSQHRSHRQMATTTNPLIRHENRMVLASTTAKAME QMAGSSEQAAEAMEVANQTRQMVHAMRTVGTHPNSSAGLKDDLLENLQAYQKRMGVQM QRFK)(SEQ ID NO: 47); A/Maryland/28/2009 (GTHPSSSAGLKDDLLGNLQ) (SEQ ID NO: 48) or (IYNRMGTVTTEAAFGLVCATCEQIADSQHRSHRQMATTTNPLIRHENRMVLASTTAK AMEQMAGSSEQAAEAMEVANQTRQMVHAMRTIGTHPSSSAGLKDDLLGNLQAYQKRMG VQMQRFK)(SEQ ID NO: 49); A/New Mexico/05/2012 (GTHPSSSSGLRDDLLENLQ) (SEQ ID NO: 50) or (IYNRMGTVTTEAAFGLVCATCEQIADSQHRSHRQMATTTNPLIRHENRMV LASTTAKAMEQMAGSSEQAAEAMEVANQTRQMVHAMRTIGTHPSSSSGLR DDLLENLQAY QKRMGVQMQRFK)(SEQ ID NO: 51); A/Phillipines/TMC10-135/2010 (GTHPSSSAGLRDDLLDNLQ) (SEQ ID NO: 52) or (IYNRMGTVTTEAAFGLVCATCEQIAD SQHRSHRQMATTTNPLIRHENRMVLAST-TAKAMEQMAGSSEQAAEAMEVANQTRQMVHA MRTIGTHPSSSAGLRDDLLDNLQAY-QKRMGVQMQRFK)(SEQ ID NO: 53); A/Singapore/GP4307/2010 (GTHPSSSAGLKDDLLDNLQ) (SEQ ID NO: 54) or (IYNRMGTVTTEAAFGLVCATCEQIADSQHRSHRQMATTTNPLIRHENRMVLASTTAKAME QMAGSSEQAAEAMEVANQTRQMVHAMR-TIGTHPSSSAGLKDDLLDNLQAYQKRMGVQM QRFK)(SEQ ID NO: 55); A/Singapore/GP489/2010 (GTHPSSSAGLKDALLENLQ) (SEQ ID NO: 56) or (IYNRMGTVTTEAAFGLVCATCEQIADSQHRSHRQ-MATTTNPLIRHENRMVLAST TAKAMEQMAGSSE-QAAEAMEVANQTRQMVHAMRTIGTHPSSSAGLKD ALLENLQAYQKR MGVQMQRFK)(SEQ ID NO: 57); A/Boston/14/2007 (GTHPSSSTGLRDDLLEKLQ) (SEQ ID NO: 58) or (IYNRMGAVTTEVAFGLVCATCEQIAD-SQHRSHRQMVATTNPLIKHENRMVLAS TTAKAMEQMAGSSEQAAEAMEIASQARQMVQAM-RAIGTHPSSSTGLRDDLLEKLQTYQKR MGVQMQRFK)(SEQ ID NO: 59); A/Brisbane/09/2006 (GTHPSSSTGLRDNLLENLQ) (SEQ ID NO: 60) or (IYN-RMGAVTTEVAFGLVCATCEQIADSQHRSHRQM-VATTNPLIKHENRMV LASTTAKAMEQMAGSSE-QAAEAMEIASQARQMVQAMRAIGTHPSSSTGLR DNLLENLQTY QKRMGVQMQRFK)(SEQ ID NO: 61); A/Hong Kong/CUH34175/2002 (GTHPSSSNGLRDDL-LENLQ) (SEQ ID NO: 62) or (IYNRMGAVTTEVAFGLV-CATCEQIADS QHRSHRQMVATTNPLIRHENRMV-LASTTAKAMEQMAGSSEQAAEAMEIASQAR QMVQAM RAIGTHPSSSNGLRDDLLENLQTY-QKRMGVQMQRFK)(SEQ ID NO: 63); A/Kyrgyzstan/WRAIR1256P/2008 (GTHPSSSTGLRDDLLGNLQ) (SEQ ID NO: 64) or (IYNRMGAVTTEVAFGLVCATCEQIAD-SQHRSHRQMVATTNPLIKHENRMVLASTTAKAME QMAGSSEQAAEAMEIASQARQMVQAM-RAIGTHPSSSTGLRDDLLGNLQTYQKRMGVQMQ RFK)(SEQ ID NO: 65); A/Malaysia/12530/1997 (GTHPSSSTGLRDDLLDNLQ) (SEQ ID NO: 66) or (IYN-RMGAVTTEVAFGLVCATCEQIADSQHRSHRQM-VATTNPLIRHENRMVLASTTAK AMEQMAGSSE-QAAEAMEIASQARQMVQAMRAVGTHPSSSTGL RDDLLDNLQTYQKRMGV QMQRFK)(SEQ ID NO: 67); A/Nanjing/1663/2010 (GTHPSSSTGLRGDLLENLQ) (SEQ ID NO: 68) or (IYNRMGAVTTEVAFGLVCATCEQ-IADSQHRSHRQMVATTNPLIKHENRMVLASTTA KAMEQMAGS SEQAAEAMEIASQARQMVQAM-RAIGTHPS SSTGLRGDLLENLQTYQKRMG VQMQR-FR)(SEQ ID NO: 69); A/Wyoming/08/2010 (GTHPSSST-GLRDDLIENLQ) (SEQ ID NO: 70) or (IYNRMGAVTTEVAFGLVCATCEQIADSQHRSHRQM-VSTTNPLIKHENRMVLASTTA RAMEQMAGSSE-QAAEAMEIASQARQMVQAMRAIGTHPSSSTGLRD-DLIENLQTYQKRMGV QMQRFK)(SEQ ID NO: 71); A/Berkeley/1/1968 (GTPPSSSAGLKNDLLENLQ) (SEQ ID NO: 72) or (IYNRMGAVTTEVAFGLVCATCEQIAD-SQHRSHRQMVTTTNPLIRHENRMVLASTTAK AMEQMAGSSEQAAEAMEVATQARQMVQAMRAIGT-PPSSSAGLKNDLLENLQAYQKRMGV QMQRFK)(SEQ ID NO: 73); A/Korea/426/1968 (GTPPSSSAGLKDDL-LENLQ) (SEQ ID NO: 74) or (IYNRMGAVTTEVAFGLV-CATCEQIADSQHRSHRQMVTTTNPLIRHENRMV-LASTTAK AMEQMAGSSEQAAEAMEVASQARQMVQAMRAIGT-PPSSSAGLKDDLLENLQAYQKRMGV QMQRFK)(SEQ ID NO: 75).

In an embodiment, the M1 polypeptides of the invention comprise the sequence from 220-238 of the M1 protein, GTHPSSSAGLKNDLLENLQ (SEQ ID NO: 1), or variants with one or more of the following substitutions: H at 222 changed to R or N, S at 224 changed to R or N, A at 227 changed to T or N, K at 230 changed to R, N at 231 changed to D, S, or K, D at 232 changed to N or G, L at 234 changed to F or I, E at 235 changed to D, H, or K, N at 236 changed to H or K.

```
220
  G T H P S S S A G L K N D L L E
      R     R       T       R D N     F D
      N     N       N           S G   I H
                                  K     K

    238
  N L Q  (SEQ ID NO: 1)
  H      (SEQ ID NO: 76)
  K
```

In an embodiment, the M1 polypeptides of the invention encompass the following sequence variants:

```
220
  G T X P X S S X G L X X X L X

    238
  X X L Q  (SEQ ID NO: 77)
```

Where X=any amino acid.

In an embodiment, the M1 polypeptides of the invention comprise sequence from 131-252 of the M1 protein, or variants with one or more of the following substitutions: A at 137 changed to T, T at 139 changed to A, V at 142 changed to S or A, V at 147 changed to I, R at 160 changed to K, V at 166 changed to A, T at 167 changed to A or S, R at 174 changed to K, L at 180 changed to I, K at 187 changed to R, A at 200 changed to S, V at 205 changed to D or I, A at 206 changed to I, S at 207 changed to N, A at 209 changed to T, Q at 214 changed to H, T at 218 changed to A, H at 222 changed to R, P, or N, S at 224 changed to R or N, A at 227 changed to T, S, or N, K at 230 changed to R or G, N at 231 changed to D, S, or K, D, at 232 changed to N, A, or G, L at 234 changed to F or I, E at 235 changed to D, H, G, K, N at 236 changed to H or K, or A at 239 changed to T. These changes and the reference sequence are shown in Table 1 (SEQ ID NO. 78).

In an embodiment, the M1 polypeptides of the invention encompass the following sequence variants:

```
                                              (SEQ ID NO: 79)
131       140       150       160       170       180
IYNRMGXVXTEXAFGLXCATCEQIADSQHXSHRQMXXTTNPLIXHENRMVX

     190       200       210       220       230
ASTTAXAMEQMAGSSEQAXEAMEXXXQXRQMVXAMRXIGTXPXSSXGLXXX

     240       250
LXXXLQXYQKRMGVQMQRFK
```

Where X=any amino acid.

In an embodiment, the M1 polypeptides of the invention include M1 polypeptides encoded by nucleic acids that hybridize under stringent hybridization conditions to nucleic acids encoding one of the polypeptides of SEQ ID NOS: 1-80. In an embodiment, the M1 polypeptides of the invention include M1 polypeptides encoded by nucleic acids that hybridize under stringent hybridization conditions to nucleic acids encoding one of the polypeptides of SEQ ID NOS: 1-7.

In an embodiment, the M1 polypeptides of the invention include M1 polypeptides encoded by nucleic acids that hybridize under stringent hybridization conditions to nucleic acids encoding one of the polypeptides of SEQ ID NOS: 8-75. In an embodiment, the M1 polypeptides of the invention include M1 polypeptides encoded by nucleic acids that hybridize under stringent hybridization conditions to nucleic acids encoding one of the polypeptides of SEQ ID NOS: 2-5. In an embodiment, the M1 polypeptides of the invention include M1 polypeptides encoded by nucleic acids that hybridize under stringent hybridization conditions to nucleic acids encoding the polypeptide of SEQ ID NO: 3.

In an embodiment, the M1 polypeptides of the invention have at least 70%, 80%, 90%, 95%, or 99% sequence identity to one of SEQ ID NOS: 1-80. In an embodiment, the M1 polypeptides of the invention have at least 70%, 80%, 90%, 95%, or 99% sequence identity to one of SEQ ID NOS: 1-7. In an embodiment, the M1 polypeptides of the invention have at least 70%, 80%, 90%, 95%, or 99% sequence identity to one of SEQ ID NOS: 8-75. In an embodiment, the M1 polypeptides of the invention have at least 70%, 80%, 90%, 95%, or 99% sequence identity to one of SEQ ID NOS: 2-5. In an embodiment, the M1 polypeptides of the invention have at least 70%, 80%, 90%, 95%, or 99% sequence identity to SEQ ID NO: 3.

The M1 polypeptides of the invention are capable of protecting against influenza. That is, they are capable of stimulating an immune response in an animal. The antigen may comprise an M1 polypeptide alone or conjugated to a carrier or presented in a scaffold; a recombinant vector containing an insert with immunogenic properties; an epitope, a hapten, or any combination thereof.

M1 polypeptides of the invention encompass immunogenic fragments and variants of the M1 polypeptides. Thus, the term "immunogenic or antigenic polypeptide" further contemplates deletions, additions and substitutions to the sequence, so long as the polypeptide functions to produce an immunological response as defined herein. The term "conservative variation" denotes the replacement of an amino acid residue by another biologically similar residue, or the replacement of a nucleotide in a nucleic acid sequence such that the encoded amino acid residue does not change or is changed to another structurally, chemically or otherwise functionally similar residue. In this regard, particularly preferred substitutions will generally be conservative in nature, i.e., those substitutions that take place within a family of amino acids. For example, amino acids are generally divided into four families: (1) acidic—aspartate and glutamate; (2) basic—lysine, arginine, histidine; (3) non-polar—alanine, valine, leucine, isoleucine, proline, phenylalanine, methionine, tryptophan; and (4) uncharged polar—glycine, asparagine, glutamine, cysteine, serine, threonine, and tyrosine. Phenylalanine, tryptophan, and tyrosine are sometimes classified as aromatic amino acids. Examples of conservative variations include the substitution of one hydrophobic residue such as isoleucine, valine, leucine or methionine for another hydrophobic residue, or the substitution of one polar residue for another polar residue, such as the substitution of arginine for lysine, glutamic acid for aspartic acid, or glutamine for asparagine, and the like; or a similar conservative replacement of an amino acid with a structurally related amino acid that will not have a major effect on the biological activity. Proteins having substantially the same amino acid sequence as the reference molecule but possessing minor amino acid substitutions that do not substantially affect the immunogenicity of the protein are, therefore, within the definition of the reference polypeptide. All of the polypeptides produced by these modifications are included herein. The term "conservative variation" also includes the use of a substituted amino acid in place of an unsubstituted parent amino acid provided that antibodies raised to the substituted polypeptide also immunoreact with the unsubstituted polypeptide.

"Variant" M1 polypeptide is intended to mean substantially similar sequences. For polynucleotides, a variant comprises a deletion and/or addition of one or more nucleotides at one or more sites within the native polynucleotide and/or a substitution of one or more nucleotides at one or more sites in the native polynucleotide. As used herein, a "native" polynucleotide or polypeptide comprises a naturally occurring nucleotide sequence or amino acid sequence, respectively. Variants of a particular polynucleotide of the invention (i.e., the reference polynucleotide) can also be evaluated by comparison of the percent sequence identity between the polypeptide encoded by a variant polynucleotide and the polypeptide encoded by the reference polynucleotide. "Variant" protein is intended to mean a protein derived from the native protein by deletion or addition of one or more amino acids at one or more sites in the native protein and/or substitution of one or more amino acids at one or more sites in the native protein. Variant proteins encompassed by the present invention are biologically active, that is they possess the ability to elicit an immune response.

Homologs of M1 polypeptides from other influenza strains and subtypes are intended to be within the scope of the present invention. As used herein, the term "homologs" includes analogs and paralogs. The term "anologs" refers to two polynucleotides or polypeptides that have the same or similar function, but that have evolved separately in unrelated host organisms. The term "paralogs" refers to two polynucleotides or polypeptides that are related by duplication within a genome. Paralogs usually have different functions, but these functions may be related. Analogs and paralogs of a wild-type influenza polypeptide can differ from the wild-type influenza polypeptide by post-translational modifications, by amino acid sequence differences, or by both. In particular, homologs of the invention will generally exhibit at least 80-85%, 85-90%, 90-95%, or 95%, 96%, 97%, 98%, 99% sequence identity, with all or part of the wild-type influenza polypeptide or polynucleotide sequences, and will exhibit a similar function. Variants include allelic variants. The term "allelic variant" refers to a polynucleotide or a polypeptide containing polymorphisms that lead to changes in the amino acid sequences of a protein and that exist within a natural population (e.g., a virus species or variety). Such natural allelic variations can typically result in 1-5% variance in a polynucleotide or a polypeptide. Allelic variants can be identified by sequencing the nucleic acid sequence of interest in a number of different species, which can be readily carried out by using hybridization probes to identify the same genetic locus in those species. Any and all such nucleic acid variations and resulting amino acid polymorphisms or variations that are the result of natural allelic variation and that do not alter the functional activity of the gene of interest, are intended to be within the scope of the invention.

As used herein, the term "derivative" or "variant" refers to a M1 polypeptide, or a nucleic acid encoding a M1 polypeptide, that has one or more conservative amino acid variations or other minor modifications such that (1) the corresponding polypeptide has substantially equivalent function when compared to the wild type polypeptide or (2) an antibody raised against the polypeptide that is immunoreactive with the wild-type polypeptide. These variants or derivatives include polypeptides having minor modifications of the influenza polypeptide primary amino acid sequences that may result in peptides which have substantially equivalent activity as compared to the unmodified counterpart polypeptide. Such modifications may be deliberate, as by site-directed mutagenesis, or may be spontaneous. The term “variant” further contemplates deletions, additions and substitutions to the sequence, so long as the polypeptide functions to produce an immunological response as defined herein. The term “variant” also includes the modification of a polypeptide where the native signal peptide is replaced with a heterologous signal peptide to facilitate the expression or secretion of the polypeptide from a host species. The term “variant” may also include ‘mimitopes’, which are completely different protein sequence but similar structure, that also induce cross-reactive immunity.

M1 polypeptides of the invention also may include amino acid sequences for introducing a glycosylation site or other site for modification or derivatization of the M1 polypeptide. In an embodiment, the M1 polypeptides of the invention described above may include the amino acid sequence N-X-S or N-X-T that can act as a glycosylation site. During glycosylation, an oligosaccharide chain is attached to asparagine (N) occurring in the tripeptide sequence N-X-S or N-X-T, where X can be any amino acid except Pro. This sequence is called a glycosylation sequence. This glycosylation site may be placed at the N-terminus, C-terminus, or within the internal sequence of the M1 sequence used for the M1 polypeptide.

Any of the M1 polypeptides of the invention may also be used in a hapten conjugate. Such conjugates may use a suitable carrier polypeptide and/or a scaffold polypeptide for presenting the M1 polypeptide epitope(s) to the organism’s immune system. For example, the M1-polypeptide may be inserted into the CDR3, or completely replace the CDR3, of a monoclonal antibody. In this case, the greatest adjuvanting effect will be attained by using a monoclonal antibody scaffold of a different species from the subject for immunization. These M1-polypeptides haptens may increase or create an immune response to the M1 polypeptide. Suitable carrier molecules are well known in the art and include, for example, KLH, ovalbumin, BSA, other serum albumins, cholera toxin, diphtheria toxin and tetanus toxin.

The standard techniques of molecular biology for preparing and purifying DNA constructs enable the preparation of the hapten conjugates with the M1 polypeptides of this invention. These molecular biology techniques can be used to make the gene constructs that encode the hapten conjugates, and to make expression constructs for manufacture of the hapten in suitable host cells. Alternatively, the haptens of the invention may be made using standard polypeptide techniques for conjugating M1 polypeptides of the invention to carrier or scaffold polypeptides. While standard techniques of molecular biology are therefore sufficient for the production of the haptens of this invention, the specific haptens disclosed provide novel therapeutics.

In an aspect of the present invention, there is provided a monovalent or multivalent e.g. bivalent, trivalent or quadrivalent composition comprising a M1 polypeptide(s) and may also include an inactivated or attenuated influenza virus or antigenic preparation thereof, for use in the reduction of the severity or the prevention of influenza infections caused by an influenza strain which is an antigenic variant of the strain present in said primary immunogenic composition. In an embodiment of the invention, the inactivated or attenuated influenza virus of the multivalent composition is for a serotype B influenza.

Immune Response and Efficacy

In an embodiment, the M1 polypeptide vaccine of the invention is able to induce a humoral response in terms of neutralizing antibodies against influenza, as measured by Geometric Mean Titers (GMT) of the neutralizing antibody titers and seroconversion rates (SCR) for neutralizing antibody response (defined as the percentage of vaccines without detectable antibody on Day 0 and an increase to a titer of 1:28 or with a 4-fold or greater increase in neutralizing antibody titer at post vaccination).

In another particular embodiment said vaccination also or additionally generates a CD4 T cell immune response and/or a B cell memory response against influenza. In a specific embodiment the human patient is seronegative or immunologically naive (i.e. does not have pre-existing immunity) to the vaccine strain. In an embodiment, the administration of said M1 polypeptide composition alternatively or additionally induces a B-memory cell response, as measured by the frequency of peripheral blood B lymphocytes capable of differentiation into antibody-secreting plasma cells upon antigen encounter.

The influenza medicament of the invention suitably meets certain international criteria for vaccines. Standards are applied internationally to measure the efficacy of influenza vaccines. Serological variables are assessed according to criteria of the European Agency for the Evaluation of Medicinal Products for human use (CHMP/BWP/214/96, Committee for Proprietary Medicinal Products (CPMP). Note for harmonization of requirements for influenza vaccines, 1997. CHMP/BWP/214/96 circular N° 96-0666:1-22) for clinical trials related to annual licensing procedures of influenza vaccines (Table 1A). The requirements are different for adult populations (18-60 years) and elderly populations (>60 years) (Table 1A). For interpandemic influenza vaccines, at least one of the assessments (seroconversion factor, seroconversion rate, seroprotection rate) should meet the European requirements, for all strains of influenza included in the vaccine. The proportion of titers equal or greater than 1:40 is regarded most relevant because these titers are expected to be the best currently available correlate of protection (Beyer W et al. 1998. Clin Drug Invest.; 15:1-12).

A 70% seroprotection rate is defined by the European health regulatory authority (CHMP—Committee for Medicinal Products for Human Use) as one of three criteria normally required to be met for an annual seasonal influenza vaccine and which CHMP is also expecting a pandemic candidate vaccine to meet.

However, mathematical modeling has indicated that a vaccine that is, at the population level, only 30% efficient against one or more heterologous strain(s) antigenically drifted may also be of benefit in helping to reduce the magnitude of a pandemic and that a pandemic vaccination campaign using a (pre-pandemic) vaccine with 30% efficacy against the pandemic strain (cross-protection of 30%) could effectively reduce the clinical attack rate by 75% and consequently morbidity/mortality within the population. Accordingly, the accelerated primary immunization of the present invention is a method for achieving early mitigation of an influenza pandemic or containment of an emerging influenza strain at the source.

The FDA has published a draft guidance (CBER draft criteria) (available from the Office of Communication, Training and Manufacturers Assistance (HFM-40), 1401 Rockville Pike, Suite 200N, Rockville, Md. 20852-1448, or by calling 1-800-835-4709 or 301-827-1800, or from the Internet at www.fda.gov/cber/guidelines.htm) on Clinical Data Needed to Support the Licensure of Pandemic Influenza Vaccines, and the proposed criteria are also based on the CHMP criteria. The FDA uses slightly different age cut-off points. Appropriate endpoints similarly include: 1) the percent of subjects achieving an HI antibody titer 1:40, and 2) rates of seroconversion, defined as a four-fold rise in HI antibody titer post-vaccination. The geometric mean titer (GMT) should be included in the results, but the data should include not only the point estimate, but also the lower bound of the 95% confidence interval of the incidence rate of seroconversion, and the day 42 incidence rate of HI titers of 1:40 must meet or exceed the target value. These data and the 95% confidence intervals (CI) of the point estimates of these evaluations should therefore be provided. FDA draft guidance requires that both targets be met.

Accordingly, in one aspect of the invention, it is provided for a composition, method or use as claimed herein wherein said immune response or protection induced by the administration of the M1 polypeptide composition meets all three EU regulatory criteria for influenza vaccine efficacy. Suitably at least one, suitably two, or three of following criteria are met for the influenza strain of the composition: a seroconversion rate of >30%, of >40%, of >50% in the seronegative population; a seroprotection rate of >60%, of >70%, of >80% in the seronegative population; a seroconversion factor of >2.0, of >2.5, of >3.0, of >4.0 in the seronegative population.

Influenza Virus

Influenza A viruses are continuously evolving and as a consequence, undergo antigenic variation (Johnson N P, Mueller J. Updating the accounts: global mortality of the 1918-1920 "Spanish" influenza pandemic. Bull. Hist. Med. 2006; 76:105-115, which is hereby incorporated by reference in its entirety). During inter-pandemic periods, influenza viruses that circulate are related to those from the preceding epidemic. The viruses spread among people with varying levels of immunity from infections earlier in life. Such circulation, over a period of usually 2-3 years, and a lack of effective proofreading by the viral RNA polymerase, leads to a high rate of transcription errors that can result in amino-acid substitutions in surface glycoproteins and that promotes the selection of new strains that have changed enough to cause an epidemic again among the general population; this process is termed "antigenic drift."

The segmented viral genome allows for a second type of antigenic variation. At unpredictable intervals, if two or more influenza viruses simultaneously infect a host cell, genetic reassortment will result in novel influenza viruses. Here, the resulting antigens can vary from 20% to 50% from the corresponding protein of strains that were previously circulating in humans. This phenomenon, called "antigenic shift" may generate a novel virus with new surface or internal proteins which escapes 'herd immunity' and establishes pandemics.

These antigenic changes, both "drifts" and "shifts" are unpredictable and may have a dramatic impact from an immunological point of view as they eventually lead to the emergence of new influenza strains that enable the virus to escape the immune system causing the well-known, almost annual, epidemics.

In addition to annual epidemics, newly emerging influenza viruses capable of efficient human-to-human transmission have caused pandemics in the past, i.e. sudden, global epidemics in all age groups with higher infectivity and mortality rates. The last century has seen three influenza pandemics, the "Spanish Flu" in 1918-1919, responsible for the deaths of 20 to 50 million people worldwide, the "Asian Flu" in 1957 and the "Hong Kong Flu" in 1968.

The features of a pandemic influenza virus strain are: it contains a new hemagglutinin compared to the hemagglutinin in the currently circulating strains, which may or not be accompanied by a change in neuraminidase subtype; it is capable of being transmitted horizontally in the human population; and it is pathogenic for humans. A new hemagglutinin can be one which has not been evident in the human population for an extended period of time, probably for at least a decade such as H2 which last circulated in 1957, or it may be a hemagglutinin that has never been circulating in the human population before, for example H5, H9, H7 or H6 which are usually found in birds. In these cases, a large proportion (in the case of H2 for example) or the entire (in the case of H5, H7, H6 or H9) population is immunologically naive to the pandemic influenza virus strain. At present, the influenza A virus that has been identified by the WHO as one that potentially could cause an influenza pandemic in humans is the highly pathogenic H5N1 avian influenza virus. Therefore, the pandemic vaccine for use according to the invention will suitably comprise H5N1 virus. Other suitable strains for inclusion into the claimed composition are H9N2, H7N1, H7N7 or H2N2.

The M1 polypeptides of the invention are less susceptible to such antigenic variation because (1) the selected region influenza genome that encodes the M1 polypeptides of the invention also encodes a portion of the M2 protein; and (2) the M1 and M2 proteins of influenza are structural proteins that are largely embedded in the virus particle. For both these reasons, the M1 proteins has less sequence variation among influenza strains, and likely will have less ability to support the rapid antigenic drift seen in the surface exposed antigens such as hemagglutinin.

DNA and RNA Vaccines

M1 polypeptides of the invention may also be introduced to an organism as a DNA or RNA vaccine. The DNA or RNA vaccines of the invention will encode the M1 polypeptides of the invention. These encoded M1 polypeptides may be present in an encoded fusion protein with a carrier polypeptide or fused into a scaffold polypeptide.

The standard techniques of molecular biology for preparing and purifying DNA or RNA constructs enable the preparation of the DNA or RNA therapeutics of this invention. While standard techniques of molecular biology are sufficient for the production of the products of this invention, the specific constructs disclosed herein provide novel therapeutics.

The amount of expressible DNA or RNA to be introduced to a vaccine recipient will depend on the strength of the transcriptional and translational promoters used in the DNA or RNA construct, and on the immunogenicity of the expressed gene product. In general, an immunologically or prophylactically effective dose of about 1 μg to 1 mg, and preferably about 10 μg to 300 μg is administered directly into muscle tissue. Subcutaneous injection, intradermal introduction, impression through the skin, and other modes of administration such as intraperitoneal, intravenous, or inhalation delivery are also contemplated. It is also contemplated that booster vaccinations are to be provided.

The DNA or RNA may be naked, that is, unassociated with any proteins, adjuvants or other agents, which impact on the recipient's immune system. In this case, it is desirable for the DNA or RNA to be in a physiologically acceptable solution, such as, but not limited to, sterile saline or sterile buffered saline. Alternatively, the DNA or RNA may be associated with liposomes, such as lecithin liposomes or other liposomes known in the art, as a DNA-liposome mixture or RNA-liposome mixture, (see for example WO93/24640) or the DNA or RNA may be associated with an adjuvant known in the art to boost immune responses, such as a protein or other carrier. Agents which assist in the cellular uptake of DNA or RNA, such as, but not limited to, calcium ions, viral proteins and other transfection facilitating agents may also be used to advantage. These agents are generally referred to as transfection facilitating agents and as pharmaceutically acceptable carriers. As used herein, the term gene refers to a segment of nucleic acid which encodes a discrete polypeptide. The term pharmaceutical, and vaccine are used interchangeably to indicate compositions useful for inducing immune responses. The terms construct, and plasmid are used interchangeably. The term vector is used to indicate a DNA or RNA into which genes may be cloned for use according to the method of this invention.

DNA vaccine formulations which comprise a demetalated solution containing a physiologically acceptable buffer within a pH range from at least greater than about 8.0 to about at least 9.5, a salt (including but not limited to NaCl, KCl or LiCl) in the range of up to about at 300 mM, and the metal ion chelator EDTA (in the range of up to about 5 mM) in combination with the free radical scavenger ethanol (in the range of up to about 3%) and the highest appropriate DNA concentration in a sterile glass vial, packaged to protect the highly purified, nuclease free DNA from light and in a physiologically acceptable buffer. In a specific aspect of the present invention, the DNA vaccine formulations comprise a combination of EDTA and ethanol, NaCl at a concentration from about 100 mM to about 200 mM, EDTA in the range from about 1 μM to about 1 mM, ethanol present up to about 2%, all in the highest appropriate DNA concentration in a sterile glass vial, packaged to protect the highly purified, nuclease free DNA from light and in a physiologically acceptable buffer.

The DNA or RNA vaccines of the disclosure include sequences that are degenerate as a result of the genetic code, e.g., optimized codon usage for a specific host. As used herein, "optimized" refers to a polynucleotide that is genetically engineered to increase its expression in a given species. To provide optimized polynucleotides coding for influenza polypeptides, the DNA or RNA sequence of the influenza protein gene can be modified to 1) comprise codons preferred by highly expressed genes in a particular species; 2) comprise an A+T or G+C content in nucleotide base composition to that substantially found in said species; 3) form an initiation sequence of said species; or 4) eliminate sequences that cause destabilization, inappropriate polyadenylation, degradation and termination of RNA, or that form secondary structure hairpins or RNA splice sites. Increased expression of influenza protein in said species can be achieved by utilizing the distribution frequency of codon usage in eukaryotes and prokaryotes, or in a particular species. The term "frequency of preferred codon usage" refers to the preference exhibited by a specific host cell in usage of nucleotide codons to specify a given amino acid. There are 20 natural amino acids, most of which are specified by more than one codon. Therefore, all degenerate nucleotide sequences are included in the disclosure as long as the amino acid sequence of the influenza polypeptide encoded by the nucleotide sequence is functionally unchanged.

Hybridization reactions can be performed under conditions of different "stringency." Conditions that increase stringency of a hybridization reaction are well known. See for example, "Molecular Cloning: A Laboratory Manual", second edition (Sambrook et al., 1989). Additional detail on making and administering DNA vaccines of the invention are found in U.S. Pat. No. 7,927,870, which is hereby incorporated by reference. Additional detail on making and using RNA vaccines are found in Ulmer et al., "RNA-based vaccines", 2012, Vaccine 30, 4414-4418, which is hereby incorporated by reference.

Vaccine Preparation

Preparation of M1 polypeptides is well known in the art. M1 polypeptide at the desired degree of purity and at a sufficient concentration to induce an immune response is mixed with a physiologically acceptable carrier. A physiologically acceptable carrier is nontoxic to a recipient at the dosage and concentration employed in the vaccine. Generally, the vaccine is formulated for injection, usually intramuscular or subcutaneous injection. Suitable carriers for injection include sterile water, but preferably are physiologic salt solutions, such as normal saline or buffered salt solutions such as phosphate-buffered saline or ringer's lactate. The vaccine generally contains an adjuvant. Useful adjuvants include QS21 (*Quillaja saponaria*, commercially available from Cambridge Biotech, Worcester, Mass.), which stimulates cytotoxic T-cells, and alum (aluminum hydroxide adjuvant). Formulations with different adjuvants which enhance cellular or local immunity can also be used. In particular, immunopotentiators such as cytokines can be included in the vaccine. Examples of suitable immunopotentiating cytokines include interleukins, such as interleukin-2 (IL-2) and interleukin-12 (IL-12), and tumor necrosis factor-alpha (TNF-α).

Additional excipients that can be present in the vaccine include low molecular weight polypeptides (less than about 10 residues), proteins, amino acids, carbohydrates including glucose or dextran, chelating agents such as EDTA, and other excipients that stabilize the protein or inhibit growth of microorganisms.

Vaccines according to the invention can also contain one or more engineered virus specifically designed to express proteins that induce a cytotoxic T-cell response. Suitable engineered viruses are derived from, for example, Canary Pox virus, vaccinia viruses, Adenovirus, attenuated human herpes viruses (such as, e.g., herpes simplex viruses), and Varicella Zoster. Exemplary engineered viruses are modified to express M1 polypeptide capable of inducing a cytotoxic T-cell response. Immunization with the M1 polypeptide vaccine can be followed by administration of one or more doses of the M1 polypeptide sequence(s) to boost the immune response.

In one embodiment the primary composition for use according to the invention is adjuvanted. In a specific embodiment, the adjuvant is an oil-in-water emulsion-based adjuvant or adjuvant system. In one embodiment the oil-in-water emulsion comprises a metabolizable oil and an emulsifying agent, and optionally a sterol and/or a tocol such as alpha-tocopherol. In a another specific embodiment, said oil-in-water emulsion adjuvant comprises at least one metabolizable oil in an amount of 0.5% to 20% of the total volume, and has oil droplets of which at least 70% by intensity have diameters of less than 1 μm.

The meaning of the term metabolizable oil is well known in the art. Metabolizable can be defined as 'being capable of being transformed by metabolism' (Dorland's Illustrated Medical Dictionary, W.B. Sanders Company, 25th edition (1974)). The oil may be any vegetable oil, fish oil, animal oil or synthetic oil, which is not toxic to the recipient and is capable of being transformed by metabolism. Nuts, seeds, and grains are common sources of vegetable oils. Synthetic oils are also part of this invention and can include commercially available oils such as NEOBEE™ and others. A particularly suitable metabolizable oil is squalene. Squalene (2,6,10,15,19,23-Hexamethyl-2,6,10,14,18,22-tetracosa-hexaene) is an unsaturated oil which is found in large quantities in shark-liver oil, and in lower quantities in olive oil, wheat germ oil, rice bran oil, and yeast, and is a particularly suitable oil for use in this invention. Squalene is a metabolizable oil by virtue of the fact that it is enzymatically transformed during the biosynthesis of cholesterol (Merck index, 10th Edition, entry no. 8619). In one embodiment the metabolizable oil is present in an amount of 0.5% to 20% (final concentration) of the total volume of the immunogenic composition, suitably an amount of 1.0% to 10% of the total volume, suitably in an amount of 2.0% to 6.0% of the total volume. In a specific embodiment the metabolizable oil is present in an amount of about 0.25-1.25% (v/v) of the total volume of the immunogenic composition.

Suitably the oil-in-water emulsion systems of the present invention have a small oil droplet size in the sub-micron range. Suitably the droplet sizes will be in the range 120 to 750 nm, suitably sizes from 120 to 600 nm in diameter. Typically the oil-in water emulsion contains oil droplets of which at least 70% by intensity are less than 500 nm in diameter, in particular at least 80% by intensity are less than 300 nm in diameter, suitably at least 90% by intensity are in the range of 120 to 200 nm in diameter.

The oil in water emulsion according to the invention may also comprise a sterol and/or a tocol such as tocopherol, in particular alpha tocopherol. Sterols are well known in the art, for example cholesterol is well known and is, for example, disclosed in the Merck Index, 11th Edn., page 341, as a naturally occurring sterol found in animal fat. Other suitable sterols include β-sitosterol, stigmasterol, ergosterol and ergocalciferol. Said sterol is suitably present in an amount of about 0.01% to about 20% (w/v) of the total volume of the immunogenic composition, suitably at an amount of about 0.1% to about 5% (w/v). Suitably, when the sterol is cholesterol, it is present in an amount of between about 0.02% and about 0.2% (w/v) of the total volume of the immunogenic composition, typically at an amount of about 0.02% (w/v) in a 0.5 ml vaccine dose volume.

Tocols (e.g. vitamin E) are also often used in oil emulsions adjuvants (EP 0 382 271 B1; U.S. Pat. No. 5,667,784; WO 95/17210). Tocols used in the oil emulsions (optionally oil in water emulsions) of the invention may be formulated as described in EP 0 382 271 B1, in that the tocols may be dispersions of tocol droplets, optionally comprising an emulsifier, of optionally less than 1 micron in diameter. Alternatively, the tocols may be used in combination with another oil, to form the oil phase of an oil emulsion. Examples of oil emulsions which may be used in combination with the tocol are described herein, such as the metabolizable oils described above.

The oil in water emulsion comprises an emulsifying agent. The emulsifying agent may be present at an amount of about 0.01 to about 5.0% by weight of the immunogenic composition (w/w), suitably present at an amount of about 0.1 to about 2.0% by weight (w/w). Suitable concentrations are about 0.5 to about 1.5% by weight (w/w) of the total composition.

The emulsifying agent may suitably be polyoxyethylene sorbitan monooleate (polysorbate 80 or TWEEN® 80). In a specific embodiment, a 0.5 ml vaccine dose volume contains 1% (w/w) TWEEN® 80, and a 0.7 ml vaccine dose volume contains about 0.7% (w/w) TWEEN®. In another specific embodiment the concentration of TWEEN® is about 0.1% or about 0.2% (w/w). In one aspect the amount of polysorbate 80 is about 4.9 mg per vaccine dose, suitably from about 4.6 to about 5.2 mg per vaccine dose. In another aspect, the amount of polysorbate 80 is about 2.4 mg per vaccine dose, suitably from about 2.0 to about 2.8 mg per vaccine dose. In another aspect, the amount of polysorbate 80 is about 1.2 mg per vaccine dose, suitably from about 1.0 to about 1.5 mg per vaccine dose. In another aspect, the amount of polysorbate 80 is about 0.6 mg per vaccine dose, suitably from about 0.4-0.8 mg per vaccine dose.

The oil-in-water emulsion adjuvant may be utilized with other adjuvants or immunostimulants and therefore an important embodiment of the invention is an oil in water formulation comprising squalene or another metabolizable oil, a tocopherol, such as alpha tocopherol, and TWEEN®. The oil in water emulsion may also contain SPAN® 85 (polyoxyethylene sorbitan trioleate) and/or Lecithin. Typically the oil in water will comprise from about 2 to about 10% squalene of the total volume of the immunogenic composition, from 2 to 10% alpha tocopherol and from about 0.3 to about 3% TWEEN®, and may be produced according to the procedure described in WO 95/17210. Suitably the ratio of squalene:alpha tocopherol is equal or less than 1 as this provides a more stable emulsion. SPAN® 85 may also be present, for example at a level of about 1%.

The influenza vaccine preparation may be prepared in the presence of a preservative such as thiomersal. Suitably the preservative, in particular thiomersal, is present at a concentration of around 100 μg/ml. Alternatively, the influenza vaccine preparation is prepared in the presence of low level of preservative in particular thiomersal, such as a concentration not exceeding 20 μg/ml or suitably less than 5 μg/ml. In another suitable alternative embodiment, the influenza vaccine preparation is made in the absence of thiomersal. Suitably the resulting influenza vaccine preparation is stable in the absence of organomercurial preservatives; in particular the preparation contains no residual thiomersal. In particular the influenza vaccine preparation comprises a M1 polypeptide antigen stabilized in the absence of thiomersal, or at low levels of thiomersal (generally 5 μg/ml or less). Specifically the stabilization of B influenza strain is performed by a derivative of alpha tocopherol, such as alpha tocopherol succinate (also known as vitamin E succinate, i.e. VES). Such preparations and methods to prepare them are disclosed in WO 02/097072, which is hereby incorporated by reference in its entirety.

The volume of one dose of the adjuvanted M1 polypeptide vaccine can be between about 0.25-1 ml, and usually corresponds to about 0.5 ml for an adult formulation. Suitably a 0.5 ml adult dose corresponds to about 0.25 ml adjuvant plus about 0.25 ml antigen). Each vaccine dose can contain about 15 μg M1 polypeptide. In an alternative embodiment, each vaccine dose contains a low amount of M1 polypeptide, such as an amount of less than about 15 suitably less than about 10 μg. Suitable amounts are about 2 μg, about 4 μg, about 5 μg, about 7.5 μg, or about 10 μg M1 polypeptide or any suitable amount of M1 polypeptide lower than about 15 μg such that the vaccine composition meets at least one of the efficacy criteria as defined herein. Advantageously an M1 polypeptide dose of about 1 μg or even less such as about 0.5 μg that would allow meeting the regulatory criteria defined above. A vaccine dose of about 1 ml (about 0.5 ml adjuvant plus about 0.5 ml antigen preparation) is also suitable. A vaccine dose of about 0.25 ml (e.g. about 0.125 ml adjuvant plus about 0.125 ml antigen preparation) is also suitable, especially for the pediatric population. The volume of one dose of the M1 polypeptide vaccine can be between about 0.25-1 ml, and usually corresponds to about 0.5 ml for an adult formulation. Suitably a 0.5 ml adult dose corresponds to about 0.25 ml adjuvant plus about 0.25 ml antigen. A vaccine dose of about 1 ml (about 0.5 ml adjuvant plus about 0.5 ml antigen preparation) is also suitable. A vaccine dose of about 0.25 ml (e.g. about 0.125 ml adjuvant plus about 0.125 ml antigen preparation) is also suitable, especially for the pediatric population.

Immunostimulants

In another embodiment, the composition may comprise an additional adjuvant in particular a TLR-4 ligand adjuvant, suitably a non-toxic derivative of lipid A. A suitable TLR-4 ligand is 3 de-O-acylated monophosphoryl lipid A (3D-MPL). Other suitable TLR-4 ligands are lipopolysaccharide (LPS) and derivatives, MDP (muramyl dipeptide) and F protein of RSV.

In one embodiment the composition may additionally include a Toll like receptor (TLR) 4 ligand, such as a non-toxic derivative of lipid A, particularly monophosphoryl lipid A or more particularly 3-Deacylated monophosphoryl lipid A (3D-MPL).

Said lipopolysaccharide, which is preferably 3D-MPL, can be used at amounts between 1 and per human dose of the immunogenic composition. Advantageously 3D-MPL is used at a level of around 25 for example between 20-30 suitably between 21-29 μg or between 22 and 28 μg or between 23 and 27 μg or between 24 and 26 or 25 μg. In another embodiment, the human dose of the immunogenic composition comprises 3D-MPL at a level of around 10 for example between 5 and 15 μg, suitably between 6 and 14 μg, for example between 7 and 13 μg or between 8 and 12 μg or between 9 and 11 μg, or 10 μg. In a further embodiment, the human dose of the immunogenic composition comprises 3D-MPL at a level of around 5 μg, for example between 1 and 9 μg, or between 2 and 8 μg or suitably between 3 and 7 μg or 4 and 6 μg, or 5 μg.

The dose of MPL is suitably able to enhance an immune response to an antigen in a human. In particular, a suitable MPL amount is that which improves the immunological potential of the composition compared to the unadjuvanted composition, or compared to the composition adjuvanted with another MPL amount, whilst being acceptable from a reactogenicity profile.

Synthetic derivatives of lipid A are known, some being described as TLR-4 agonists, and include, but are not limited to: OM174 (2-deoxy-6-o-[2-deoxy-2-[(R)-3-dodecanoyloxytetradecanoylamino]-4-o-phos-phono-.beta.-D-glucopyranosyl]-2-[(R)-3-hydroxytetradecanoylamino]-.alpha.-D-glucopyranosyldihydrogenphosphate), (WO 95/14026) OM 294 DP (3S,9R)-3-[(R)-dodecanoyloxytetradecanoylamino]-4-oxo-5-aza-9(R)-[(R)-3-h-ydroxytetradecanoylamino]decan-1,10-diol,1,10-bis(dihydrogenophosphate) (WO99/64301 and WO 00/0462) OM 197 MP-Ac DP (3S-,9R)-3-[(R)-dodecanoyloxytetradecanoylamino]-4-oxo-5-aza-9-[(R)-3-hydroxytetradecanoylamino]decan-1,10-d ol, 1-dihydrogenophosphate 10-(6-aminohexanoate) (WO 01/46127)

Other TLR4 ligands which may be used are Alkyl Glucosaminide Phosphates (AGPs) such as those disclosed in WO9850399 or U.S. Pat. No. 6,303,347 (processes for preparation of AGPs are also disclosed), or pharmaceutically acceptable salts of AGPs as disclosed in U.S. Pat. No. 6,764,840, all three patent documents are hereby incorporated by reference in their entirety. Some AGPs are TLR4 agonists, and some are TLR4 antagonists. Both are thought to be useful as adjuvants.

Other suitable TLR-4 ligands, capable of causing a signaling response through TLR-4 (Sabroe et al, JI 2003 p 1630-5, which is hereby incorporated by reference in its entirety) are, for example, lipopolysaccharide from gram-negative bacteria and its derivatives, or fragments thereof, in particular a non-toxic derivative of LPS (such as 3D-MPL). Other suitable TLR agonist are: heat shock protein (HSP) 10, 60, 65, 70, 75 or 90; surfactant Protein A, hyaluronan oligosaccharides, heparin sulphate fragments, fibronectin fragments, fibrinogen peptides and b-defensin-2, muramyl dipeptide (MDP) or F protein of respiratory syncytial virus. In one embodiment the TLR agonist is HSP 60, 70 or 90.

Toll-like receptors (TLRs) are type I transmembrane receptors, evolutionarily conserved between insects and humans. Ten TLRs have so far been established (TLRs 1-10) (Sabroe et al, JI 2003 p 1630-5, which is hereby incorporated by reference in its entirety). Members of the TLR family have similar extracellular and intracellular domains; their extracellular domains have been shown to have leucine-rich repeating sequences, and their intracellular domains are similar to the intracellular region of the interleukin-1 receptor (IL-1R). TLR cells are expressed differentially among immune cells and other cells (including vascular epithelial cells, adipocytes, cardiac myocytes and intestinal epithelial cells). The intracellular domain of the TLRs can interact with the adaptor protein Myd88, which also possess the IL-1R domain in its cytoplasmic region, leading to NF-KB activation of cytokines; this Myd88 pathway is one way by which cytokine release is affected by TLR activation. The main expression of TLRs is in cell types such as antigen presenting cells (e.g., dendritic cells, macrophages etc).

In another embodiment, the adjuvant and immunogenic composition further comprises a saponin adjuvant. A particularly suitable saponin for use in the present invention is Quil A and its derivatives. Quil A is a saponin preparation isolated from the South American tree *Quillaja Saponaria* Molina and was first described by Dalsgaard et al. in 1974 ("Saponin adjuvants", Archiv. fur die gesamte Virusforschung, Vol. 44, Springer Verlag, Berlin, p 243-254, which is hereby incorporated by reference in its entirety) to have adjuvant activity. Purified fragments of Quil A have been isolated by HPLC which retain adjuvant activity without the toxicity associated with Quil A (EP 0 362 278), for example QS7 and QS21 (also known as QA7 and QA21). QS-21 is a natural saponin derived from the bark of *Quillaja saponaria* Molina, which induces CD8+ cytotoxic T cells (CTLs), Th1 cells and a predominant IgG2a antibody response and is a preferred saponin in the context of the present invention. In a suitable form of the present invention, the saponin adjuvant within the immunogenic composition is a derivative of saponaria molina quil A, preferably an immunologically active fraction of Quil A, such as QS-17 or QS-21, suitably QS-21. In one embodiment the compositions of the invention contain the immunologically active saponin fraction in substantially pure form. Preferably the compositions of the invention contain QS21 in substantially pure form, that is to say, the QS21 is at least 90% pure, for example at least 95% pure, or at least 98% pure.

Other useful saponins are derived from the plants *Aesculus hippocastanum* or *Gyophilla struthium*. Other saponins which have been described in the literature include Escin, which has been described in the Merck index (12th ed: entry 3737) as a mixture of saponins occurring in the seed of the horse chestnut tree, *Aesculus hippocastanum*. Its isolation is described by chromatography and purification (Fiedler, Arzneimittel-Forsch. 4, 213 (1953), which is hereby incorporated by reference in its entirety), and by ion-exchange resins (Erbring et al., U.S. Pat. No. 3,238,190, which is hereby incorporated by reference in its entirety). Fractions of scion have been purified and shown to be biologically active (Yoshikawa M, et al. (Chem Pharm Bull (Tokyo) 1996 August; 44(8):1454-1464), which is hereby incorporated by reference in its entirety). Sapoalbin from *Gypsophilla struthium* (R. Vochten et al., 1968, J. Pharm. Belg., 42, 213-226, which is hereby incorporated by reference in its entirety) are also an option.

The dose of 3D-MPL and/or QS21 is suitably able to enhance an immune response to an antigen in a human. In particular a suitable 3D-MPL and/or QS21 amount is that which improves the immunological potential of the composition compared to the unadjuvanted composition, or compared to the composition adjuvanted with another 3D-MPL or QS21 amount, whilst being acceptable from a reactogenicity profile. Typically for human administration the saponin (e.g. QS21) and/or LPS derivative (e.g. 3D-MPL) will be present in a human dose of immunogenic composition in the range of 1 μg-200 such as 10-50 or 1 μg-25 μg per dose.

Adjuvants wherein an additional immunostimulant is optionally included are particularly suitable for infant and/or Elderly Vaccine Formulations.

Vaccination

The composition of the invention may be administered by any suitable delivery route, such as intradermal, mucosal e.g. intranasal, oral, intramuscular, subcutaneous, intradural, intravenous, mucosal, or pulmonary. Other delivery routes are well known in the art.

The intramuscular delivery route is particularly suitable for the M1 polypeptide compositions of the invention. The composition according to the invention may be presented in a monodose container, or alternatively, a multidose container, particularly suitable for a pandemic vaccine. In this instance an antimicrobial preservative such a thiomersal is typically present to prevent contamination during use. Thiomersal concentration may be at 25 μg/0.5 ml dose (i.e. 50 μg/mL). A thiomersal concentration of 5 μg/0.5 ml dose (i.e. 10 μg/ml) or 10 μg/0.5 ml dose (i.e. 20 μg/ml) is suitably present. A suitable IM delivery device could be used such as a needle-free liquid jet injection device, for example the Biojector 2000 (Bioject, Portland, Oreg.). Alternatively a pen-injector device could be used. The use of such delivery devices may be particularly amenable to large scale immunization campaigns such as would be required during a pandemic.

Intradermal delivery is another suitable route. Any suitable device may be used for intradermal delivery, for example needle-free or short needle devices such as devices which limit the effective penetration length of a needle into the skin, such as those described in WO99/34850 and EP1092444, incorporated herein by reference in their entirety, and functional equivalents thereof. Also suitable are jet injection devices which deliver liquid vaccines to the dermis via a liquid jet injector or via a needle which pierces the stratum corneum and produces a jet which reaches the dermis. Also suitable are ballistic powder/particle delivery devices which use compressed gas to accelerate vaccine in powder form through the outer layers of the skin to the dermis. Additionally, conventional syringes may be used in the classical mantoux method of intradermal administration.

Another suitable administration route is the subcutaneous route. Any suitable device may be used for subcutaneous delivery, for example a classical needle or a needle-free jet injector service. Suitably said device is pre-filled with the liquid vaccine formulation.

Alternatively the vaccine is administered intranasally. Typically, the vaccine is administered locally to the nasopharyngeal area, suitably without being inhaled into the lungs. It is desirable to use an intranasal delivery device which delivers the vaccine formulation to the nasopharyngeal area, without or substantially without it entering the lungs. Suitable devices for intranasal administration of the vaccines according to the invention are spray devices that are well-known in the art.

Alternatively, the epidermal or transdermal vaccination route is also contemplated in the present invention.

Antibodies

Antibodies of the invention will have binding specificity for one or more of the M1 polypeptides of the invention. The antibodies of the invention encompass all forms as discussed above. In an embodiment, the antibody will be engineered for a particular organism. The organism can be a human, canine, or a commercially valuable livestock, such as, for example, pigs, horses, dogs, cats, chickens, or other birds. Such engineering of the antibody includes, for example, humanization, humaneering, chimerization, or isolating human (or other organism) antibodies using any of the repertoire technologies or monoclonal technologies known in the art.

Established methods for the isolation of antigen-specific human antibodies include the screening of hybridomas from mice that are transgenic for the human immunoglobulin loci (e.g., Jakobavits, 1998, Adv Drug Deliv Rev. 31:33-42, which is hereby incorporated by reference in its entirety), and in vitro methods in which recombinant libraries of human antibody fragments displayed on and encoded in filamentous bacteriophage (e.g., McCafferty et al., 1990, Nature 348:552-554, which is hereby incorporated by reference in its entirety), yeast cells (e.g., Boder and Wittrup, 1997, Nat Biotechnol 15:553-557, which is hereby incorporated by reference in its entirety), and ribosomes (e.g., Hanes and Pluckthun, 1997, Proc Natl Acad Sci USA 94:4937-4942, which is hereby incorporated by reference in its entirety) are panned against immobilized antigen. These methods have yielded many useful human antibodies.

Mice transgenic for human immunoglobulin loci generally do not express the full complement of human diversity, but human antibodies expressed in these transgenic animals can undergo affinity maturation. Antibodies of desired higher affinities and specificities can be obtained from these transgenic mice whereas human antibodies obtained from display technologies will be limited by the antibody repertoire used as these display antibodies do not undergo natural affinity maturation in the display systems.

The most widely used methods for minimizing the immunogenicity of non-human antibodies while retaining specificity and affinity involve grafting the CDRs of the non-human antibody onto human frameworks typically selected for their structural homology to the non-human framework (Jones et al., 1986, Nature 321:522-5; U.S. Pat. No. 5,225,539, both of which are hereby incorporated by reference in their entirety). Originally these methods resulted in drastic losses of affinity. However, it was then shown that some of the affinity could be recovered by restoring the non-human residues at key positions in the framework that are required to maintain the canonical structures of the non-human CDRs 1 and 2 (Bajorath et al., 1995, J Biol Chem 270:22081-4; Martin et al., 1991, Methods Enzymol. 203:121-53; Al-Lazikani, 1997, J Mol Biol 273:927-48, all of which are hereby incorporated by reference in their entirety). Recovering the native conformations of CDR3s is a much more uncertain enterprise because their structures are more variable. Determining which non-human residues to restore to recover functional CDR3 conformation is thus largely a matter of modeling where possible combined with trial and error. Exemplary methods for humanization of antibodies by CDR grafting are disclosed, for example, in U.S. Pat. No. 6,180,370, which is hereby incorporated by reference in its entirety.

Improvements to the traditional CDR-grafting approaches use various hybrid selection approaches, in which portions of the non-human antibody have been combined with libraries of complementary human antibody sequences in successive rounds of selection for antigen binding, in the course of which most of the non-human sequences are gradually replaced with human sequences. For example, in the chain-shuffling technique (Marks, et al., 1992, *Biotechnology* 10:779-83, which is hereby incorporated by reference in its entirety) one chain of the non-human antibody is combined with a naive human repertoire of the other chain on the rationale that the affinity of the non-human chain will be sufficient to constrain the selection of a human partner to the same epitope on the antigen. Selected human partners are then used to guide selection of human counterparts for the remaining non-human chains.

Other methodologies include chain replacement techniques where the non-human CDR3s were retained and only the remainder of the V-regions, including the frameworks and CDRs 1 and 2, were individually replaced in steps performed sequentially (e.g., U.S. Patent Application No. 20030166871; Rader, et al., Proc Natl Acad Sci USA 95:8910-15, 1998; Steinberger, et al., J. Biol. Chem. 275: 36073-36078, 2000; Rader, et al., J. Biol. Chem. 275:13668-13676, 2000, all of which are hereby incorporated by reference in their entirety).

The above described methodologies can be used with the anti-M1 polypeptide antibodies of the invention to change the host range of the anti-M1 polypeptide antibodies by using the desired host as the donor of the appropriate antibody sequences.

In an embodiment, the anti-M1 polypeptide antibodies of the invention are modified with molecules that enhance the half-life of the antibody in the body of an organism. Such modifications include, for example, PEGylation, or derivatization with other hydrophilic polymers such as dextran, or other polycarbohydrates, PVP (polyvinylpyrrolidone), PVA (polyvinyl alcohol), etc. Such polymers for such derivatization are well known in the art.

In an embodiment, the antibodies of the invention include monoclonal antibody 2B-B10-G9 that binds to the C-terminal region of Influenza virus Matrix (M1) protein spanning the amino acids 220-238. The hybridoma was raised against the PR/8 M protein and its binding has been mapped to the sequence GHTPSSSAGLKNDLLENLQ (SEQ ID NO: 82). In an embodiment, the anti-M1 polypeptide antibody is 2B-B10-G9, or an antibody that binds to the epitope of 2B-B10-G9, or a humaneered, humanized, chimerized, or otherwise genetically engineered variant of 2B-B10-G9.

Methods of Treatment with Antibodies

The present invention provides a method of therapy comprising administering to an animal an effective amount of anti-M1 polypeptide antibody, such that a subsequent infection by influenza virus is reduced in severity and/or the infection is reduced in duration of flu symptoms. In an embodiment, an effective amount of anti-M1 polypeptide antibody is administered to an animal after the animal is infected with influenza virus. In an embodiment, an effective amount of anti-M1 polypeptide antibody is administered to an animal before the animal is infected with influenza virus. In an embodiment, the administration of an effective amount of anti-M1 polypeptide antibody in an animal infected with influenza virus reduces the severity of the influenza infection and/or reduces the duration of flu symptoms in the animal. In an embodiment, the animal treated with the anti-M1 polypeptide antibody therapy is a human patient.

In an embodiment, anti-M1 antibody 2B-B10-G9 is administered intravenously to mice at a dose of 50 mg/kg and the mice are then challenged with intranasal influenza virus of the strain A/PR/8/34 or A/CA/04/09. This antibody is a mouse IgG1 isotype. The mice acquired about 50% protection from the 2B-B10-G9 antibody. The anti-M1 antibody 2B-B10-G9 is also engineered to a more active isotype, such as IgG2a, and the challenged experiment is repeated. In an embodiment, the anti-M1 antibody binds to the epitope of 2B-B10-G9, has human framework sequences, and has the human IgG1 isotype. In an embodiment, the anti-M1 antibody is a humanized or humaneered 2B-B10-G9 with a human IgG1 isotype. These alternative antibodies are administered at doses of 1 μg/kg to 100 mg/kg by intravenous or intranasal administration to mice or humans. Alternatively, these antibodies may be engineered for administration to birds, e.g., chickens, livestock, e.g., pigs, cows, horses, etc., or pets, e.g., dogs, cats, etc.

Depending on the type and severity of the disease, about 1 μg/kg to 100 mg/kg (e.g., 0.1-20 mg/kg) of anti-M1 polypeptide antibody is an initial dosage for administration to the patient, whether, for example, by one or more separate administrations, or by continuous infusion. A typical daily dosage might range from about 1 μg/kg to about 100 mg/kg or more, depending on the need of the patient. Particularly desirable dosages include, for example, 5 mg/kg, 7.5 mg/kg, 10 mg/kg, and 15 mg/kg. For repeated administrations over several days or longer, depending on the condition, the treatment is sustained until the influenza infection is treated, as measured by the methods known in the art. In an embodiment, other dosage regimens may be useful. For example, if the anti-M1 polypeptide antibody of the invention is administered once every week, every two weeks, every three weeks, every four weeks, or a longer period of time between doses at a dose range from about 5 mg/kg to about 15 mg/kg, including but not limited to 5 mg/kg, 7.5 mg/kg, 10 mg/kg or 15 mg/kg. The progress of the therapy of the invention is easily monitored by conventional techniques and assays.

Therapeutic formulations of the anti-M1 polypeptide antibodies used in accordance with the present invention are prepared for storage by mixing an antibody having the desired degree of purity with optional pharmaceutically acceptable carriers, excipients or stabilizers (Remington's Pharmaceutical Sciences 16th edition, Osol, A. Ed. (1980)), generally in the form of lyophilized formulations or aqueous solutions. Antibody crystals are also contemplated (see US Pat Appln 2002/0136719, which is hereby incorporated by reference in its entirety). Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN®, PLURONIC® or polyethylene glycol (PEG).

The formulation herein may also contain more than one active compound as necessary for treatment, preferably those with complementary activities that do not adversely affect each other. The active ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980), which is hereby incorporated by reference in its entirety.

Sustained-release preparations may be prepared. Suitable examples of sustained-release preparations include semipermeable matrices of solid hydrophobic polymers containing the antibody, which matrices are in the form of shaped articles, e.g., films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919, which is hereby incorporated by reference in its entirety), copolymers of L-glutamic acid and .gamma. ethyl-L-glutamate, non-degradable ethylene-vinyl acetate, degradable lactic acid-glycolic acid copolymers such as the LUPRON DEPOT® (injectable microspheres composed of lactic acid-glycolic acid copolymer and leuprolide acetate), and poly-D-(−)-3-hydroxybutyric acid.

Manufacturing of Polypeptides

Recombinant techniques for the manufacture of the M1 polypeptides and/or antibodies of the invention are well known in the art. M1 polypeptides or antibodies of the invention can be manufactured in a variety of host cell types, for example, in mammalian cells, fungal cells, yeast cells, bacterial cells, insect cells, etc. The techniques for making recombinant expression constructs or vectors for use in certain host cells, such as yeast or filamentous fungi, or mammalian cells, such as Chinese hamster ovary cells, murine NIH 3T3 fibroblasts, human embryonic kidney 193 cells, or rodent myeloma or hybridoma cells, *E. coli*, certain insect cells, and other commercially available host cell systems are well known in the art. It is also well known in the art to express recombinant polypeptides in these host cells and to obtain the recombinant polypeptides from these host cells. In an embodiment, full length antibodies of the invention will be made in host cell systems capable of glycosylating the antibody. In an embodiment, the glycosylation will be that of the target organism to be treated with the antibody. In an embodiment, the glycosylation will resemble the glycosylation of the organism to be treated with the antibody. In an alternative embodiment, the glycosylation will differ from the organism to be treated so that the glycosylation provides an adjuvant effect, but does not substantially impair effector functions of the antibody.

The M1 polypeptides of the invention can also be made by chemical synthesis using polypeptide synthesis apparati (e.g., in a test tube).

All publications and patents cited in this specification are herein incorporated by reference as if each individual publication or patent were specifically and individually indicated to be incorporated by reference and are incorporated herein by reference to disclose and describe the methods and/or materials in connection with which the publications are cited.

EXAMPLES

Example 1. Inhibition of Influenza Infection by Anti-M1 Polypeptide Antibody The monoclonal antibody 2B-B10-G9 was investigated for binding to a panel of influenza strains and for neutralization activity in plaque inhibition assays. Monoclonal antibody 2B-B10-G9 binds to the C-terminal region of Influenza virus Matrix (M1) protein spanning the amino acids 220-236. 2B-B10-G9 may also bind to M1 protein at amino acids spanning 220-237, 220-238, 220-239, 220-240, or 220-241.

Figure 2:
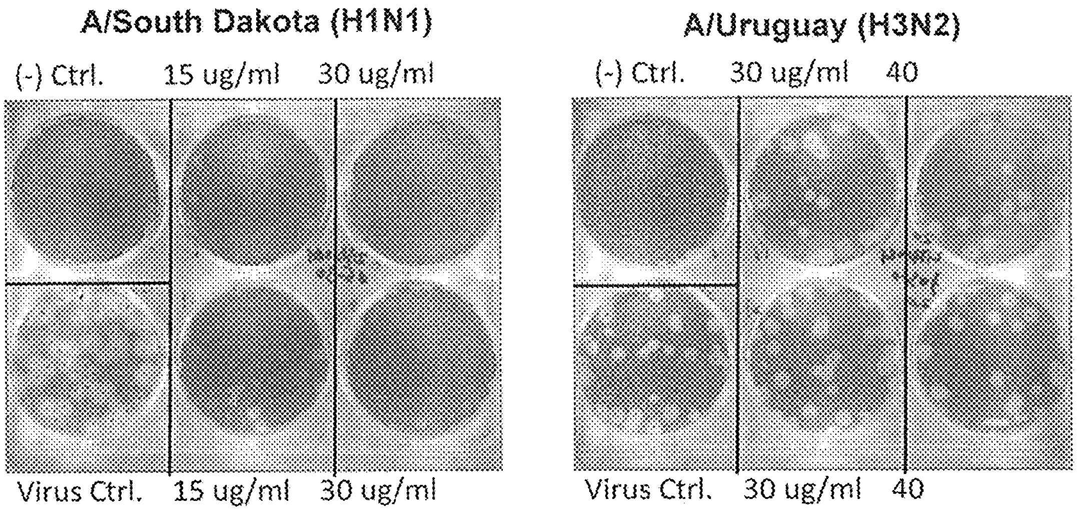
FIG. 2 shows a plaque inhibition assay of additional influenza strains by monoclonal antibody 2B-B10-G9.

2B-B10-G9 was added in agar overlays to a partially infected lawn of MDCK cells and incubated for 3 days at 37° C. with $CO_2$ (FIG. 1). Results indicated that 15 ug of antibody completely inhibited plaque formation. Because 2B-B10-G9 has access only to exposed portions of M protein on virus or infected cells, prevention of plaquing indicates that the C-terminal region of Matrix protein from PR/8 must be surface-accessible. Inhibition of viral plaques on a lawn of MDCK cells were further analyzed by two separate methods. Cells were infected with virus and incubated for 30 minutes prior to addition of an agar overlay containing 2B-B10-G9 antibody. Alternatively, virus and antibody were mixed and incubated for 30 minutes prior to infecting cells. After infection and an additional 30 minute incubation, an agar overlay without antibody was added. Results indicated no difference between the two experiments in total plaques inhibited. These results suggest that inhibition of viral infection is caused by binding of 2B-B10-G9 to the virus and not prevention of viral budding from infected cells. Additional testing revealed that 2B-B10-G9 inhibited plaque formation of A/South Dakota (H1N1) and partially inhibited A/Uruguay (H3N2) in plaque assays (FIG. 2). An amino acid variation at position 231 may be responsible for the reduced efficacy of the antibody. However, even partial inhibition indicates that the extended C-terminus of M protein (at amino acid residues 215-252) is surface-exposed and is a viable target for immunization. Further testing of viruses with either an asparagine or an aspartic acid at position 231 was performed. The M protein from PR/8 and A/South Dakota contain an Asparagine at position 231 while A/Uruguay contains an Aspartic acid at this position. In addition PR/8 and South Dakota have H1N1 surface glycoproteins while Uruguay has H3N2 surface glycoproteins. To determine if 2B-B10-G9 has broadly neutralizing activity, a series of neutralization experiments were performed to test effectiveness against both the Asparagine and Aspartic acid variation at position 231 in the H1N1 setting and against the aspartic acid setting in the H3N2 setting. An M protein containing an asparagine at position 231 could not be tested in an H3N2 virus as this variation does not appear to occur in wild type viruses. Two viruses, A/WSN/33 and A/Port Chalmers/1/73, were tested in the plaque inhibition assay. A/WSN/33 is an H1N1 virus but unlike PR/8, contains an aspartic acid at position 231 in M1 protein. A/Port Chalmers/1/73 is an H3N2 virus that contains an aspartic acid at position 231. Simultaneously, two control viruses were also tested: A/PR/8 and A/USSR/90/77. PR/8 and USSR/90 have the same amino acid sequence from AA 220 to AA 236 but have different H1N1 proteins. Results showed that all viruses were inhibited by 2B-B10-G9 in a dose dependent manner (FIG. 3). Inhibition of plaquing by 2B-B10-G9 was unaffected by the amino acid variation at position 231 and unaffected by either the H3N2 or H1N1 glycoproteins. Combined, the above data and a sequence analysis of wild type M proteins contained in the NCBI Database, it is reasonable to conclude that 2B-B10-G9 binds all known variants of M1. Presentation of the C-terminal peptide 215-252 in a vaccine setting, would generate a polyclonal response taking advantage of the well-documented potency conferred by an avid antibody response, leading to a non-linear increase in protection conferred by the vaccine as opposed to a monoclonal antibody. This polyclonal antibody response would afford the vaccinated organism universal protection against any influenza possessing the A type matrix protein.

Example 2. New Anti-M1 Polypeptide Antibodies

A M1 polypeptide comprising the amino acid sequence from 220-236 of the M1 protein from A/PR/8/38 influenza virus was conjugated to immunogenic carrier proteins (KLH, Ovalbumin, and BSA) and injected into 10-12 week old female BALB/c mice. This M1 polypeptide has the amino acid sequence GHTPSSSAGLKNDLLEN (SEQ ID NO: 81). Two subsequent boosts were given, one boost at 14 and one at 28 days after the initial injection. Serum bleeds were collected just prior to inoculation and 7 days after each of the three injections. Analysis of collected sera indicates a strong response to the M1 polypeptide and to whole M1 protein itself after the second boost.

The peptide, GHTPSSSAGLKNDLLEN (SEQ ID NO: 81), comprises the amino acid sequence from 220-236 of A/PR/8 matrix protein. The peptide was chemically conjugated to KLH, Ovalbumin, and BSA.

10-12 week old female BALB/c mice were randomized into three groups for inoculation: Group A—Control (mice 77-81), Group B—Peptide conjugate (mice 82-86), Group C—Peptide only (mice 87-91). All mice were injected on Day 1, Day 15 and Day29. Day 1 injections included Freund's complete adjuvant and subsequent boosts contained Freund's incomplete adjuvant. Group A mice (control) were injected with 50 ug KLH initially and boosted twice (days 15 and 29) with 50 ug Ovalbumin. Group B mice were inoculated with 50 ug KLH-peptide conjugate (Day 1) and boosted twice (days 15 and 29) with 50 ug ovalbumin-peptide conjugate. Group C mice were injected and boosted with peptide (no conjugate) in amounts representing Molar equivalents to Group B.

Three groups of mice were inoculated with BSA only (Group A, mice 77-81), M1 polypeptide-BSA conjugate (Group B, mice 82-86), or M1 polypeptide only (Group C, mice 87-91). Mice were boosted twice with either BSA only (Group A), M1 polypeptide conjugate (Group B), or M1 polypeptide only (Group C). Serum collected from Group A (BSA only) showed no binding to BSA, M1 polypeptide-BSA conjugate, and M1 protein (FIG. 1). Serum collected from group B (M1 polypeptide-BSA conjugate) shows binding to M1 polypeptide-BSA conjugate as well as binding to M protein. No binding to BSA was observed indicating that binding to the M1 polypeptide was specific. Serum collected from M1 polypeptide only (Group C) displayed no binding to BSA, M1 polypeptide-BSA conjugate, or M protein.

Example 3. M1 Polypeptides with Glycosylation

Comparison of immunological response and protection using glycosylated and a-glycosylated forms of M1 polypeptides is evaluated in mouse models. A major variant at position 231 may affect binding of antibodies to this antigenic site, serological response to M1 polypeptides with the mutation at position 231 will also be tested.

Purified a-glycosylated M1 polypeptide and mutant 231 M1 polypeptide are combined in equal proportions and 50 ug administered with Freunds adjuvant into a group of mice (10 mice/group). Concurrently, glycosylated M1 polypeptides are administered to an additional group of mice with Freunds adjuvant. Each group is boosted with 10 ug of their respected M1 polypeptides after two weeks. Bleeds of approximately 100 μl are taken from each mouse one day prior to the initial injection, one day prior to boost and seven days post boost. Serum from each mouse is analyzed for binding to M1 polypeptide (plus and minus glycosylation), M1 protein, and against a control nonspecific peptide. After two weeks, one additional boost is administered and serum collected 7 days after boost. Serum response to variants of M1 polypeptide allow for quantification of the response to glycosylated and a-glycosylated forms and also determine immunization schedules for the virus challenge experiment.

Six groups of mice (10 mice/group) are immunized and boosted with M1 polypeptide and mutant 231 M1 polypeptide. Three groups will receive the combined glycosylated M1 polypeptide (groups 1-3), and 3 groups will receive the a-glycosylated forms (groups 4-6) with adjuvant. Mice are challenged three days post final boost with a lethal dose of influenza virus. Groups are challenged with virus representing the three identified variants of M protein: A/PR/8 (Groups 1, 4), A/WSN or equivalent (Groups 2, 5), and A/South Dakota or equivalent (Groups 3, 6). Three additional groups are challenged with each virus as non-immunized controls. Body temperature and survival are measured over 7 days.

Example 4. Inhibition of Influenza Virus by Anti-M1 Polypeptide Antibody

Because antibody neutralization in vitro proved effective at blocking viral infection, the ability of 2B-B10-G9 to block viral infection in a living organism was tested. Whole, live chicken eggs were used as a proxy for live animals based on the antibody's ability to block viral replication in living eggs. Traditionally, in ovo infection with influenza virus is used for; (1) selection of high yielding re-assortant viruses as seed strains for vaccine production and (2) manufacturing of influenza strains for vaccine production. Chicken egg-based manufacturing of influenza virus is considered the most robust and best method for manufacturing influenza virus. Therefore, blocking of viral replication in this host is a strong indicator of therapeutic potency. In this experiment, prevention of in ovo replication of the virus is used as an assay for determining therapeutic potency of the 2B-B10-G9 antibody. Two hundred infective viral particles (A/PR/8/34) were mixed into 750 μg/ml of 2B-B10-G9 antibody. A/PR/8/34 is traditionally used for production of reassortant seed viruses due to it's ability to replicate extremely high amounts of virus rapidly. After a 30-minute incubation at room temperature, 100 μl of the antibody virus mix was injected into 10 day fertilized chicken eggs. A control consisting of virus without antibody was also injected into 10 day fertilized chicken eggs. The eggs were sealed with paraffin, incubated at 35° C. for 40 hrs and the allantoic fluids harvested. The allantoic fluid was then tested for virus by a standard hemagglutination assay. Samples were serially diluted 2 fold and 0.5% chicken red blood cells were added. Samples were scored for hemagglutination after 30 minute incubation at room temperature. Two separate, identical experiments were performed.

TABLE 2

| | | Fold dilution | | | | | | | | | | | |
|---|---|---|---|---|---|---|---|---|---|---|---|---|---|
| | | 2 | 4 | 8 | 16 | 32 | 64 | 128 | 256 | 512 | 1024 | 2048 | 4096 |
| Sample | Control 1 | + | + | + | + | + | + | + | + | + | + | + | + |
| | Control 2 | + | + | + | + | + | + | + | + | + | + | + | + |
| | PR/8 + Ab1 | − | − | − | − | − | − | − | − | − | − | − | − |
| | PR/8 + Ab2 | − | − | − | − | − | − | − | − | − | − | − | − |

Control 1,2: PR/8/34 only, PR/8+Ab1,2: PR/8+750 ug/ml 2B-B10-G9. Results showed that the addition of 2B-B10-G9 antibody completely blocked viral replication in ovo (Table 2). The volume of allantoic fluid in 10 day fertilized chicken eggs is 10 mls, therefore the final concentration of antibody in ovo was 7.5 μg/ml.

Example 5: Inhibition of Influenza Virus by Anti-M1 Antibody in Mice

In an embodiment, the anti-M1 antibody 2B-B10-G9 was mixed with live influenza virus of the strains A/PR/8/34 or A/CA/04/09, and then this mixture was administered intranasally to mice. 500 μg of anti-M1 antibody 2B-B10-G9 was mixed with a 1×LD90 dose of influenza virus and then administered to the mice. All mice inoculated were protected from influenza virus infection by the anti-M1 antibody 2B-B10-G9.

In an embodiment, anti-M1 antibody 2B-B10-G9 was administered intravenously to mice at a dose of 50 mg/kg and the mice were then challenged with intranasal influenza virus of the strain A/PR/8/34 or A/CA/04/09. This antibody is an IgG1 isotype. The mice acquired about 15% protection from the intranasal influenza virus challenge with pre-i.v. injection of the 2B-B10-G9 antibody.

The anti-M1 antibody 2B-B10-G9 is also engineered to a human IgG1 isotype, and the challenged experiment is repeated. Human IgG1 isotype 2B-B10-G9 is administered intravenously to mice at a dose of 50 mg/kg (multiple doses are optionally administered prior to challenge) and the mice are then challenged with intranasal influenza virus of the strains A/PR/8/34, ANCA/04/09, or A/Victoria/3/75. Human IgG1 isotype 2B-B10-G9 is also administered intranasally to mice at a dose of 25 mg/kg or 50 mg/kg and the mice are then challenged with intranasal influenza virus of the strains A/PR/8/34, ANCA/04/09, or A/Victoria/3/75.

Example 6: Immunization with M1 Polypeptides Comprising Residues 220-242 (SEQ ID NO: 2), 220-252 (SEQ ID NO: 3) or 233-252 (SEQ ID NO: 80)

In an embodiment, three different M1 polypeptides are conjugated to three different carriers and then used to immunize rabbits. The three M1 polypeptides are:

```
Peptide 1 (220-242)
                                        (SEQ ID NO: 2)
GTHPSSSAGLKNDLLENLQAYQK

Peptide 2 (220-252)
                                        (SEQ ID NO: 3)
GTHPSSSAGLKNDLLENLQAYQKRMGVQMQRFK
```

-continued

```
Peptide 3 (234-252)
                                       (SEQ ID NO: 80)
LLENLQAYQKRMGVQMQRFK
```

Each peptide was made with a single Cysteine residue at the N-terminus to allow conjugation to carrier proteins. Each of these peptides 1-3 (SEQ ID NOs: 2, 3, and 80, respectively) were separately conjugated via the N-terminal Cysteine to the carrier proteins KLH, ovalbumin, and BSA using routine methods. E.g., the carrier proteins were treated with 2-iminothiolane HCl following the manufacturer's instructions, and the activated carrier was conjugated to peptides with bis(maleimido)hexane as described by the manufacturer (Thermo Science BMH Catalog #22330).

Rabbits were immunized by intradermal injection of 200 μg of KLH-peptide conjugate in Complete Freund's Adjuvant combined with Mighty Quick Immune stimulator. After seven days, the rabbits received a second intradermal injection of 100 μg of KLH-peptide conjugate in Incomplete Freund's Adjuvant combined with Mighty Quick Immune stimulator. After 7 more days (day 14 from initial injection), the rabbits received a second intradermal booster injection of 100 μg of OVA-peptide 1 or 2 conjugate in Incomplete Freund's Adjuvant with Mighty Quick Immune stimulator. Sera was collected from each rabbit just prior to the initial injection, seven days after the final boost on day 21, and 14 days after the final booster, day 28, the rabbits were exsanguinated and sera was collected.

Rabbits injected with conjugates of peptide 1 and 2 showed strong antibody responses against corresponding peptide 1 or 2-BSA conjugates, whereas, rabbits injected with conjugates of peptide 3 had little or no antibody response that reacted with the corresponding peptide 3-BSA conjugate. Sera from the injected rabbits was also tested against M1 protein, and the sera from rabbits injected with peptide 1 or 2 conjugates gave strong antibody responses to M1 protein, whereas the sera of rabbits injected with peptide 3 conjugates gave little or no reaction with M1 protein. The sera from the rabbits injected with peptide1-conjugates and peptide 2-conjugates gave a very robust response against the M1 protein.

Sera from the rabbits was then tested for inhibition of plaque formation by different strains of influenza virus. MDCK cells were grown to confluence, 50 plaque forming units of influenza virus (strains A/Puerto Rico/8 (H1N1) or A/Victoria (H3N2)) were added to the plates for 45 minutes, after the 45 minute incubation the buffer with virus was removed and the cells were washed. An agar overlay containing rabbit sera at different dilutions was overlaid on the MDCK cells. After 72 hours, the agar overlay was removed and cells were fixed and stained with 0.1% Crystal Violet. At immune dilutions of 1:100 and 1:250 the sera from rabbits injected with peptide 2 conjugates showed inhibition of plaque formation from A/Puerto Rico/8 (H1N1), above the background inhibition caused by pre-immune rabbit sera. Against the virus A/Victoria (H3N2), the sera from rabbits injected with peptide 2-conjugates showed inhibition over pre-immune sera at dilutions of 1:750 and 1:1000. Also, sera from peptide 1-conjugates showed inhibition of plaque formation over pre-immune sera against A/Victoria (H3N2) at a dilution of 1:45.

Example 7: Immunization with M1 Polypeptides Comprising Residues 223-242 (SEQ ID NO: 4), 223-252 (SEQ ID NO: 5)

In an embodiment, two different M1 polypeptides are conjugated to three different carriers and then used to immunize rabbits. The two M1 polypeptides are:

```
Peptide 4 (223-242)
                                    (SEQ ID NO: 4)
PSSSAGLKNDLLENLQAYQK

Peptide 5 (223-252)
                                    (SEQ ID NO: 5)
PSSSAGLKNDLLENLQAYQKRMGVQMQRFK
```

Each peptide is made with a single Cysteine residue at the N-terminus to allow conjugation to carrier proteins. Each of peptides 4 or 5 (SEQ ID NOs: 4 or 5) are separately conjugated via the N-terminal Cysteine to the carrier proteins KLH, ovalbumin, and BSA using routine methods.

Rabbits are immunized by intradermal injection of 200 μg of KLH-peptide conjugate in Complete Freund's Adjuvant combined with Mighty Quick Immune stimulator. After seven days, the rabbits receive a second intradermal injection of 100 μg of KLH-peptide conjugate in Complete Freund's Adjuvant combined with Mighty Quick Immune stimulator. After 7 more days (day 14 from initial injection), the rabbits receive a second intradermal booster injection of 100 μg of OVA-peptide conjugate in Complete Freund's Adjuvant with Mighty Quick Immune stimulator. Sera is collected from each rabbit just prior to each injection, seven days after the final boost on day 21, and 14 days after the final booster, day 28, the rabbits were exsanguinated and sera was collected.

Sera from the rabbits is tested against peptide 4 and 5-conjugated to BSA for anti-peptide antibodies as described in Example 6, and the sera is tested in a plaque inhibition assay as described in Example 6.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited.

Those skilled in the art will recognize, or be able to ascertain using no more than routine experimentation, many equivalents to the specific embodiments of the invention described herein. Such equivalents are intended to be encompassed by the following claims.

We claim:

1. An influenza vaccine for inducing an antibody response that has an in retro neutralization activity against infection of a host cell by an influenza virus, comprising an oil in water emulsion adjuvant, and an isolated influenza M1 polypeptide consisting of a sequence selected from the group consisting of SEQ ID NOs: 2 and 3.

2. The vaccine of claim 1, wherein the influenza M1 polypeptide sequence consists of SEQ ID NO: 2.

3. The vaccine of claim 1, wherein the influenza M1 polypeptide sequence consists of SEQ ID NO: 3.

* * * * *

```
SEQUENCE LISTING

<160> NUMBER OF SEQ ID NOS: 82

<210> SEQ ID NO 1
<211> LENGTH: 19
<212> TYPE: PRT
<213> ORGANISM: Influenza A virus

<400> SEQUENCE: 1

Gly Thr His Pro Ser Ser Ser Ala Gly Leu Lys Asn Asp Leu Leu Glu
1               5                   10                  15

Asn Leu Gln


<210> SEQ ID NO 2
<211> LENGTH: 23
<212> TYPE: PRT
<213> ORGANISM: Influenza A virus

<400> SEQUENCE: 2

Gly Thr His Pro Ser Ser Ser Ala Gly Leu Lys Asn Asp Leu Leu Glu
1               5                   10                  15

Asn Leu Gln Ala Tyr Gln Lys
            20


<210> SEQ ID NO 3
<211> LENGTH: 33
<212> TYPE: PRT
<213> ORGANISM: Influenza A virus

<400> SEQUENCE: 3
```

```
Gly Thr His Pro Ser Ser Ser Ala Gly Leu Lys Asn Asp Leu Leu Glu
1               5                   10                  15

Asn Leu Gln Ala Tyr Gln Lys Arg Met Gly Val Gln Met Gln Arg Phe
            20                  25                  30

Lys


<210> SEQ ID NO 4
<211> LENGTH: 20
<212> TYPE: PRT
<213> ORGANISM: Influenza A virus

<400> SEQUENCE: 4

Pro Ser Ser Ser Ala Gly Leu Lys Asn Asp Leu Leu Glu Asn Leu Gln
1               5                   10                  15

Ala Tyr Gln Lys
            20


<210> SEQ ID NO 5
<211> LENGTH: 30
<212> TYPE: PRT
<213> ORGANISM: Influenza A virus

<400> SEQUENCE: 5

Pro Ser Ser Ser Ala Gly Leu Lys Asn Asp Leu Leu Glu Asn Leu Gln
1               5                   10                  15

Ala Tyr Gln Lys Arg Met Gly Val Gln Met Gln Arg Phe Lys
            20                  25                  30


<210> SEQ ID NO 6
<211> LENGTH: 38
<212> TYPE: PRT
<213> ORGANISM: Influenza A virus

<400> SEQUENCE: 6

Ala Met Arg Thr Ile Gly Thr His Pro Ser Ser Ser Ala Gly Leu Lys
1               5                   10                  15

Asn Asp Leu Leu Glu Asn Leu Gln Ala Tyr Gln Lys Arg Met Gly Val
            20                  25                  30

Gln Met Gln Arg Phe Lys
        35


<210> SEQ ID NO 7
<211> LENGTH: 122
<212> TYPE: PRT
<213> ORGANISM: Influenza A virus

<400> SEQUENCE: 7

Ile Tyr Asn Arg Met Gly Ala Val Thr Thr Glu Val Ala Phe Gly Leu
1               5                   10                  15

Val Cys Ala Thr Cys Glu Gln Ile Ala Asp Ser Gln His Arg Ser His
            20                  25                  30

Arg Gln Met Val Thr Thr Thr Asn Pro Leu Ile Arg His Glu Asn Arg
        35                  40                  45

Met Val Leu Ala Ser Thr Thr Ala Lys Ala Met Glu Gln Met Ala Gly
    50                  55                  60

Ser Ser Glu Gln Ala Ala Glu Ala Met Glu Val Ala Ser Gln Ala Arg
65                  70                  75                  80

Gln Met Val Gln Ala Met Arg Thr Ile Gly Thr His Pro Ser Ser Ser
                85                  90                  95
```

```
Ala Gly Leu Lys Asn Asp Leu Leu Glu Asn Leu Gln Ala Tyr Gln Lys
            100                 105                 110

Arg Met Gly Val Gln Met Gln Arg Phe Lys
        115                 120


<210> SEQ ID NO 8
<211> LENGTH: 19
<212> TYPE: PRT
<213> ORGANISM: Influenza A virus

<400> SEQUENCE: 8

Gly Thr His Pro Ser Ser Ser Thr Gly Leu Lys Asn Asp Leu Leu Glu
1               5                   10                  15

Asn Leu Gln


<210> SEQ ID NO 9
<211> LENGTH: 122
<212> TYPE: PRT
<213> ORGANISM: Influenza A virus

<400> SEQUENCE: 9

Ile Tyr Asn Arg Met Gly Ala Val Thr Thr Glu Ser Ala Phe Gly Leu
1               5                   10                  15

Ile Cys Ala Thr Cys Glu Gln Ile Ala Asp Ser Gln His Lys Ser His
            20                  25                  30

Arg Gln Met Val Thr Thr Thr Asn Pro Leu Ile Arg His Glu Asn Arg
        35                  40                  45

Met Val Leu Ala Ser Thr Thr Ala Lys Ala Met Glu Gln Met Ala Gly
    50                  55                  60

Ser Ser Glu Gln Ala Ala Glu Ala Met Glu Val Ala Ser Gln Ala Arg
65                  70                  75                  80

Gln Met Val Gln Ala Met Arg Ala Ile Gly Thr His Pro Ser Ser Ser
                85                  90                  95

Thr Gly Leu Lys Asn Asp Leu Leu Glu Asn Leu Gln Ala Tyr Gln Lys
            100                 105                 110

Arg Met Gly Val Gln Met Gln Arg Phe Lys
        115                 120


<210> SEQ ID NO 10
<211> LENGTH: 19
<212> TYPE: PRT
<213> ORGANISM: Influenza A virus

<400> SEQUENCE: 10

Gly Thr His Pro Ser Ser Ser Ala Gly Leu Lys Asn Asp Leu Leu Glu
1               5                   10                  15

Asn Leu Gln


<210> SEQ ID NO 11
<211> LENGTH: 122
<212> TYPE: PRT
<213> ORGANISM: Influenza A virus

<400> SEQUENCE: 11

Ile Tyr Asn Arg Met Gly Ala Val Thr Thr Glu Val Ala Phe Gly Leu
1               5                   10                  15

Val Cys Ala Thr Cys Glu Gln Ile Ala Asp Ser Gln His Arg Ser His
            20                  25                  30

Arg Gln Met Val Thr Thr Thr Asn Pro Leu Ile Arg His Glu Asn Arg
```

```
        35                  40                  45

Met Val Leu Ala Ser Thr Thr Ala Lys Ala Met Glu Gln Met Ala Gly
    50                  55                  60

Ser Ser Glu Gln Ala Ala Glu Ala Met Glu Val Ala Ser Gln Ala Arg
65                  70                  75                  80

Gln Met Val Gln Ala Met Arg Thr Ile Gly Thr His Pro Ser Ser Ser
                85                  90                  95

Ala Gly Leu Lys Asn Asp Leu Leu Glu Asn Leu Gln Ala Tyr Gln Lys
            100                 105                 110

Arg Met Gly Val Gln Met Gln Arg Phe Lys
        115                 120


<210> SEQ ID NO 12
<211> LENGTH: 19
<212> TYPE: PRT
<213> ORGANISM: Influenza A virus

<400> SEQUENCE: 12

Gly Thr His Pro Ser Ser Ser Ala Gly Leu Lys Asp Asp Leu Leu Glu
1               5                   10                  15

Asn Leu Gln


<210> SEQ ID NO 13
<211> LENGTH: 122
<212> TYPE: PRT
<213> ORGANISM: Influenza A virus

<400> SEQUENCE: 13

Ile Tyr Asn Arg Met Gly Ala Val Thr Thr Glu Val Ala Phe Gly Leu
1               5                   10                  15

Val Cys Ala Thr Cys Glu Gln Ile Ala Asp Ser Gln His Arg Ser His
            20                  25                  30

Arg Gln Met Val Thr Thr Thr Asn Pro Leu Ile Arg His Glu Asn Arg
        35                  40                  45

Met Val Leu Ala Ser Thr Thr Ala Lys Ala Met Glu Gln Met Ala Gly
    50                  55                  60

Ser Ser Glu Gln Ala Ala Glu Ala Met Glu Val Ala Ser Gln Ala Arg
65                  70                  75                  80

Gln Met Val Gln Ala Met Arg Thr Ile Gly Thr His Pro Ser Ser Ser
                85                  90                  95

Ala Gly Leu Lys Asp Asp Leu Leu Glu Asn Leu Gln Ala Tyr Gln Lys
            100                 105                 110

Arg Met Gly Val Gln Met Gln Arg Phe Lys
        115                 120


<210> SEQ ID NO 14
<211> LENGTH: 19
<212> TYPE: PRT
<213> ORGANISM: Influenza A virus

<400> SEQUENCE: 14

Gly Thr His Pro Ser Ser Ser Thr Gly Leu Lys Asn Asp Leu Leu Asp
1               5                   10                  15

Asn Leu Gln


<210> SEQ ID NO 15
<211> LENGTH: 122
<212> TYPE: PRT
```

<213> ORGANISM: Influenza A virus

<400> SEQUENCE: 15

Ile Tyr Asn Arg Met Gly Ala Val Thr Thr Glu Ser Ala Phe Gly Leu
1               5                   10                  15

Ile Cys Ala Thr Cys Glu Gln Ile Ala Asp Ser Gln His Lys Ser His
            20                  25                  30

Arg Gln Met Val Thr Thr Thr Asn Pro Leu Ile Arg His Glu Asn Arg
        35                  40                  45

Met Val Leu Ala Ser Thr Thr Ala Lys Ala Met Glu Gln Met Ala Gly
    50                  55                  60

Ser Ser Glu Gln Ala Ala Glu Ala Met Glu Val Ala Asn Gln Ala Arg
65                  70                  75                  80

Gln Met Val Gln Ala Met Arg Ala Ile Gly Thr His Pro Ser Ser Ser
                85                  90                  95

Thr Gly Leu Lys Asn Asp Leu Leu Asp Asn Leu Gln Ala Tyr Gln Lys
            100                 105                 110

Arg Met Gly Val Gln Met Gln Arg Phe Lys
        115                 120

<210> SEQ ID NO 16
<211> LENGTH: 19
<212> TYPE: PRT
<213> ORGANISM: Influenza A virus

<400> SEQUENCE: 16

Gly Thr His Pro Asn Ser Ser Thr Gly Leu Lys Asn Asp Leu Leu Glu
1               5                   10                  15

Asn Leu Gln

<210> SEQ ID NO 17
<211> LENGTH: 122
<212> TYPE: PRT
<213> ORGANISM: Influenza A virus

<400> SEQUENCE: 17

Ile Tyr Asn Arg Met Gly Ala Val Thr Thr Glu Ser Ala Phe Gly Leu
1               5                   10                  15

Ile Cys Ala Thr Cys Glu Gln Ile Ala Asp Ser Gln His Lys Ser His
            20                  25                  30

Arg Gln Met Val Thr Thr Thr Asn Pro Leu Ile Arg His Glu Asn Arg
        35                  40                  45

Met Val Leu Ala Ser Thr Thr Ala Lys Ala Met Glu Gln Met Ala Gly
    50                  55                  60

Ser Ser Glu Gln Ala Ala Glu Ala Met Glu Val Ala Ser Gln Ala Arg
65                  70                  75                  80

Gln Met Val Gln Ala Met Arg Ala Ile Gly Thr His Pro Asn Ser Ser
                85                  90                  95

Thr Gly Leu Lys Asn Asp Leu Leu Glu Asn Leu Gln Ala Tyr Gln Lys
            100                 105                 110

Arg Met Gly Val Gln Met Gln Arg Phe Lys
        115                 120

<210> SEQ ID NO 18
<211> LENGTH: 19
<212> TYPE: PRT
<213> ORGANISM: Influenza A virus -continued

<400> SEQUENCE: 18

```
Gly Thr His Pro Ser Ser Ser Ala Gly Leu Lys Asp Asp Leu Ile Glu
1               5                   10                  15

Asn Leu Gln
```

<210> SEQ ID NO 19
<211> LENGTH: 122
<212> TYPE: PRT
<213> ORGANISM: Influenza A virus

<400> SEQUENCE: 19

```
Ile Tyr Asn Arg Met Gly Thr Val Thr Thr Glu Val Ala Phe Gly Leu
1               5                   10                  15

Val Cys Ala Thr Cys Glu Gln Ile Ala Asp Ser Gln His Arg Ser His
            20                  25                  30

Arg Gln Met Val Thr Thr Thr Asn Pro Leu Ile Arg His Glu Asn Arg
        35                  40                  45

Met Val Leu Ala Ser Thr Thr Ala Lys Ala Met Glu Gln Met Ala Gly
    50                  55                  60

Ser Ser Glu Gln Ala Ala Glu Ala Met Glu Val Ala Ser Gln Ala Arg
65                  70                  75                  80

Gln Met Val Gln Ala Met Arg Thr Ile Gly Thr His Pro Ser Ser Ser
                85                  90                  95

Ala Gly Leu Lys Asp Asp Leu Ile Glu Asn Leu Gln Ala Tyr Gln Lys
            100                 105                 110

Arg Met Gly Val Gln Met Gln Arg Phe Lys
        115                 120
```

<210> SEQ ID NO 20
<211> LENGTH: 19
<212> TYPE: PRT
<213> ORGANISM: Influenza A virus

<400> SEQUENCE: 20

```
Gly Thr His Pro Ser Ser Ser Thr Gly Leu Lys Asp Asp Leu Leu Glu
1               5                   10                  15

Asn Leu Gln
```

<210> SEQ ID NO 21
<211> LENGTH: 122
<212> TYPE: PRT
<213> ORGANISM: Influenza A virus

<400> SEQUENCE: 21

```
Ile Tyr Asn Arg Met Gly Ala Val Thr Thr Glu Ser Ala Phe Gly Leu
1               5                   10                  15

Ile Cys Ala Thr Cys Glu Gln Ile Ala Asp Ser Gln His Lys Ser His
            20                  25                  30

Arg Gln Met Val Thr Thr Thr Asn Pro Leu Ile Arg His Glu Asn Arg
        35                  40                  45

Met Val Leu Ala Ser Thr Thr Ala Lys Ala Met Glu Gln Met Ala Gly
    50                  55                  60

Ser Ser Glu Gln Ala Ala Glu Ala Met Glu Val Ala Asn Gln Ala Arg
65                  70                  75                  80

Gln Met Val Gln Ala Met Arg Ala Ile Gly Thr His Pro Ser Ser Ser
                85                  90                  95

Thr Gly Leu Lys Asp Asp Leu Leu Glu Asn Leu Gln Ala Tyr Gln Lys
```

```
            100                 105                 110

Arg Met Gly Val Gln Met Gln Arg Phe Lys
        115                 120


<210> SEQ ID NO 22
<211> LENGTH: 19
<212> TYPE: PRT
<213> ORGANISM: Influenza A virus

<400> SEQUENCE: 22

Gly Thr His Pro Ser Ser Ser Thr Gly Leu Arg Asp Asp Leu Leu Glu
1               5                   10                  15

Asn Leu Gln


<210> SEQ ID NO 23
<211> LENGTH: 122
<212> TYPE: PRT
<213> ORGANISM: Influenza A virus
<220> FEATURE:
<221> NAME/KEY: misc_feature
<222> LOCATION: (109)..(109)
<223> OTHER INFORMATION: Xaa can be any naturally occurring amino acid

<400> SEQUENCE: 23

Ile Tyr Asn Arg Met Gly Ala Val Thr Thr Glu Val Ala Phe Gly Leu
1               5                   10                  15

Val Cys Ala Thr Cys Glu Gln Ile Ala Asp Ser Gln His Arg Ser His
            20                  25                  30

Arg Gln Met Val Ala Thr Thr Asn Pro Leu Ile Lys His Glu Asn Arg
        35                  40                  45

Met Val Leu Ala Ser Thr Thr Ala Lys Ala Met Glu Gln Met Ala Gly
    50                  55                  60

Ser Ser Glu Gln Ala Ala Glu Ala Met Glu Ile Ala Ser Gln Ala Arg
65                  70                  75                  80

Gln Met Val Gln Ala Met Arg Ala Ile Gly Thr His Pro Ser Ser Ser
                85                  90                  95

Thr Gly Leu Arg Asp Asp Leu Leu Glu Asn Leu Gln Xaa Tyr Gln Lys
            100                 105                 110

Arg Met Gly Val Gln Met Gln Arg Phe Lys
        115                 120


<210> SEQ ID NO 24
<211> LENGTH: 19
<212> TYPE: PRT
<213> ORGANISM: Influenza A virus

<400> SEQUENCE: 24

Gly Thr Arg Pro Ser Ser Ser Ala Gly Leu Lys Asp Asp Leu Leu Glu
1               5                   10                  15

Asn Leu Gln


<210> SEQ ID NO 25
<211> LENGTH: 122
<212> TYPE: PRT
<213> ORGANISM: Influenza A virus

<400> SEQUENCE: 25

Ile Tyr Asn Arg Met Gly Ala Val Thr Thr Glu Val Ala Phe Gly Leu
1               5                   10                  15

Val Cys Ala Thr Cys Glu Gln Ile Ala Asp Ser Gln His Arg Ser His
```

```
            20                  25                  30

Arg Gln Met Val Thr Thr Thr Asn Pro Leu Ile Arg His Glu Asn Arg
        35                  40                  45

Met Val Leu Ala Ser Thr Thr Ala Lys Ala Met Glu Gln Met Ala Gly
    50                  55                  60

Ser Ser Glu Gln Ala Ala Glu Ala Met Glu Val Ala Ser Gln Ala Arg
65                  70                  75                  80

Gln Met Val Gln Ala Met Arg Ala Ile Gly Thr Arg Pro Ser Ser Ser
                85                  90                  95

Ala Gly Leu Lys Asp Asp Leu Leu Glu Asn Leu Gln Ala Tyr Gln Lys
            100                 105                 110

Arg Met Gly Val Gln Met Gln Arg Phe Lys
        115                 120


<210> SEQ ID NO 26
<211> LENGTH: 19
<212> TYPE: PRT
<213> ORGANISM: Influenza A virus

<400> SEQUENCE: 26

Gly Thr His Pro Arg Ser Ser Ala Gly Leu Lys Asp Asp Leu Leu Glu
1               5                   10                  15

Asn Leu Gln


<210> SEQ ID NO 27
<211> LENGTH: 122
<212> TYPE: PRT
<213> ORGANISM: Influenza A virus

<400> SEQUENCE: 27

Ile Tyr Asn Arg Met Gly Ala Val Thr Thr Glu Val Ala Phe Gly Leu
1               5                   10                  15

Val Cys Ala Thr Cys Glu Gln Ile Ala Asp Ser Gln His Arg Ser His
            20                  25                  30

Arg Gln Met Val Thr Thr Thr Asn Pro Leu Ile Arg His Glu Asn Arg
        35                  40                  45

Met Val Leu Ala Ser Thr Thr Ala Lys Ala Met Glu Gln Met Ala Gly
    50                  55                  60

Ser Ser Glu Gln Ala Ala Glu Ala Met Glu Val Ala Ser Gln Ala Arg
65                  70                  75                  80

Gln Met Val Gln Ala Met Arg Ala Ile Gly Thr His Pro Arg Ser Ser
                85                  90                  95

Ala Gly Leu Lys Asp Asp Leu Leu Glu Asn Leu Gln Ala Tyr Gln Lys
            100                 105                 110

Arg Met Gly Val Gln Met Gln Arg Phe Lys
        115                 120


<210> SEQ ID NO 28
<211> LENGTH: 19
<212> TYPE: PRT
<213> ORGANISM: Influenza A virus

<400> SEQUENCE: 28

Gly Thr His Pro Ser Ser Ser Ala Gly Leu Lys Asn Asp Leu Phe Glu
1               5                   10                  15

Asn Leu Gln
```

<210> SEQ ID NO 29
<211> LENGTH: 122
<212> TYPE: PRT
<213> ORGANISM: Influenza A virus

<400> SEQUENCE: 29

Ile Tyr Asn Arg Met Gly Ala Val Thr Thr Glu Ser Ala Phe Gly Leu
1 5 10 15

Val Cys Ala Thr Cys Glu Gln Ile Ala Asp Ser Gln His Lys Ser His
20 25 30

Arg Gln Met Val Thr Thr Thr Asn Pro Leu Ile Arg His Glu Asn Arg
35 40 45

Met Val Leu Ala Ser Thr Thr Ala Lys Ala Met Glu Gln Met Ala Gly
50 55 60

Ser Ser Glu Gln Ala Ala Glu Ala Met Glu Val Ala Ser Gln Ala Arg
65 70 75 80

Gln Met Val Gln Ala Met Arg Ala Ile Gly Thr His Pro Ser Ser Ser
85 90 95

Ala Gly Leu Lys Asn Asp Leu Phe Glu Asn Leu Gln Ala Tyr Gln Lys
100 105 110

Arg Met Gly Val Gln Met Gln Arg Phe Lys
115 120

<210> SEQ ID NO 30
<211> LENGTH: 19
<212> TYPE: PRT
<213> ORGANISM: Influenza A virus

<400> SEQUENCE: 30

Gly Thr His Pro Ser Ser Ser Ala Gly Leu Lys Asp Asn Leu Leu Glu
1 5 10 15

Asn Leu Gln

<210> SEQ ID NO 31
<211> LENGTH: 122
<212> TYPE: PRT
<213> ORGANISM: Influenza A virus

<400> SEQUENCE: 31

Ile Tyr Asn Arg Met Gly Ala Val Ala Thr Glu Val Ala Phe Gly Leu
1 5 10 15

Ile Cys Ala Thr Cys Glu Gln Ile Ala Asp Ala Gln His Arg Ser His
20 25 30

Arg Gln Met Val Thr Thr Thr Asn Pro Leu Ile Arg His Glu Asn Arg
35 40 45

Met Val Leu Ala Ser Thr Thr Ala Lys Ala Met Glu Gln Met Ala Gly
50 55 60

Ser Ser Glu Gln Ala Ala Glu Ala Met Glu Val Ala Ser Gln Ala Arg
65 70 75 80

Gln Met Val Gln Ala Met Arg Ala Ile Gly Thr His Pro Ser Ser Ser
85 90 95

Ala Gly Leu Lys Asp Asn Leu Leu Glu Asn Leu Gln Ala Tyr Gln Lys
100 105 110

Arg Met Gly Val Gln Met Gln Arg Phe Lys
115 120

<210> SEQ ID NO 32
<211> LENGTH: 19

<212> TYPE: PRT
<213> ORGANISM: Influenza A virus

<400> SEQUENCE: 32

Gly Thr His Pro Ser Ser Ser Thr Gly Leu Lys Ser Asp Leu Leu Glu
1 5 10 15

Asn Leu Gln

<210> SEQ ID NO 33
<211> LENGTH: 122
<212> TYPE: PRT
<213> ORGANISM: Influenza A virus

<400> SEQUENCE: 33

Ile Tyr Asn Arg Met Gly Ala Val Thr Thr Glu Ser Ala Phe Gly Leu
1 5 10 15

Ile Cys Ala Thr Cys Glu Gln Ile Ala Asp Ser Gln His Lys Ser His
20 25 30

Arg Gln Met Val Thr Thr Thr Asn Pro Leu Ile Arg His Glu Asn Arg
35 40 45

Met Val Leu Ala Ser Thr Thr Ala Lys Ala Met Glu Gln Met Ala Gly
50 55 60

Ser Ser Glu Gln Ala Ala Glu Ala Met Glu Val Ala Ser Gln Ala Arg
65 70 75 80

Gln Met Val Gln Ala Met Arg Ala Ile Gly Thr His Pro Ser Ser Ser
85 90 95

Thr Gly Leu Lys Ser Asp Leu Leu Glu Asn Leu Gln Ala Tyr Gln Lys
100 105 110

Arg Met Gly Val Gln Met Gln Arg Phe Lys
115 120

<210> SEQ ID NO 34
<211> LENGTH: 19
<212> TYPE: PRT
<213> ORGANISM: Influenza A virus

<400> SEQUENCE: 34

Gly Thr His Pro Asn Ser Ser Thr Gly Leu Lys Asp Asp Leu Leu Glu
1 5 10 15

Asn Leu Gln

<210> SEQ ID NO 35
<211> LENGTH: 122
<212> TYPE: PRT
<213> ORGANISM: Influenza A virus

<400> SEQUENCE: 35

Ile Tyr Asn Arg Met Gly Thr Val Thr Thr Glu Val Ala Phe Gly Leu
1 5 10 15

Val Cys Ala Thr Cys Glu Gln Ile Ala Asp Ser Gln His Arg Ser His
20 25 30

Arg Gln Met Val Thr Thr Thr Asn Pro Leu Ile Arg His Glu Asn Arg
35 40 45

Met Val Ile Ala Ser Thr Thr Ala Lys Ala Met Glu Gln Met Ala Gly
50 55 60

Ser Ser Glu Gln Ala Ser Glu Ala Met Glu Val Ala Ser Gln Ala Arg
65 70 75 80

Gln Met Val Gln Ala Met Arg Thr Ile Gly Thr His Pro Asn Ser Ser

```
                85                  90                  95

Thr Gly Leu Lys Asp Asp Leu Leu Glu Asn Leu Gln Ala Tyr Gln Lys
            100                 105                 110

Arg Met Gly Val Gln Met Gln Arg Phe Lys
        115                 120


<210> SEQ ID NO 36
<211> LENGTH: 19
<212> TYPE: PRT
<213> ORGANISM: Influenza A virus

<400> SEQUENCE: 36

Gly Thr His Pro Ser Ser Ser Thr Gly Leu Lys Lys Asp Leu Leu Asp
1               5                   10                  15

Asn Leu Gln


<210> SEQ ID NO 37
<211> LENGTH: 122
<212> TYPE: PRT
<213> ORGANISM: Influenza A virus

<400> SEQUENCE: 37

Ile Tyr Asn Arg Met Gly Ala Val Thr Thr Glu Ser Ala Phe Gly Leu
1               5                   10                  15

Ile Cys Ala Thr Cys Glu Gln Ile Ala Asp Ser Gln His Lys Ser His
            20                  25                  30

Arg Gln Met Val Thr Thr Thr Asn Pro Leu Ile Arg His Glu Asn Arg
        35                  40                  45

Met Val Leu Ala Ser Thr Thr Ala Lys Ala Met Glu Gln Met Ala Gly
    50                  55                  60

Ser Ser Glu Gln Ala Ala Glu Ala Met Glu Val Ala Ser Gln Ala Arg
65                  70                  75                  80

Gln Met Val Gln Ala Met Arg Ala Ile Gly Thr His Pro Ser Ser Ser
                85                  90                  95

Thr Gly Leu Lys Lys Asp Leu Leu Asp Asn Leu Gln Ala Tyr Gln Lys
            100                 105                 110

Arg Met Gly Val Gln Met Gln Arg Phe Lys
        115                 120


<210> SEQ ID NO 38
<211> LENGTH: 19
<212> TYPE: PRT
<213> ORGANISM: Influenza A virus

<400> SEQUENCE: 38

Gly Thr His Pro Ser Ser Ser Asn Gly Leu Lys Asn Asp Leu Leu Glu
1               5                   10                  15

Asn Leu Gln


<210> SEQ ID NO 39
<211> LENGTH: 122
<212> TYPE: PRT
<213> ORGANISM: Influenza A virus

<400> SEQUENCE: 39

Ile Tyr Asn Arg Met Gly Ala Val Thr Thr Glu Ser Ala Phe Gly Leu
1               5                   10                  15

Ile Cys Ala Thr Cys Glu Gln Ile Ala Asp Ser Gln His Lys Ser His
            20                  25                  30
```

```
Arg Gln Met Val Thr Thr Thr Asn Pro Leu Ile Arg His Glu Asn Arg
        35                  40                  45

Met Val Leu Ala Ser Thr Thr Ala Lys Ala Met Glu Gln Met Ala Gly
    50                  55                  60

Ser Ser Glu Gln Ala Ala Glu Ala Met Glu Val Ala Ser Gln Ala Arg
65                  70                  75                  80

Gln Met Val Gln Ala Met Arg Ala Ile Gly Thr His Pro Ser Ser Ser
                85                  90                  95

Asn Gly Leu Lys Asn Asp Leu Leu Glu Asn Leu Gln Ala Tyr Gln Lys
            100                 105                 110

Arg Met Gly Val Gln Met Gln Arg Phe Lys
        115                 120


<210> SEQ ID NO 40
<211> LENGTH: 19
<212> TYPE: PRT
<213> ORGANISM: Influenza A virus

<400> SEQUENCE: 40

Gly Thr His Pro Ser Ser Ser Thr Gly Leu Arg Asn Asp Leu Leu Glu
1               5                   10                  15

Asn Leu Gln


<210> SEQ ID NO 41
<211> LENGTH: 122
<212> TYPE: PRT
<213> ORGANISM: Influenza A virus

<400> SEQUENCE: 41

Ile Tyr Asn Arg Met Gly Ala Val Thr Thr Glu Ser Ala Phe Gly Leu
1               5                   10                  15

Ile Cys Ala Thr Cys Glu Gln Ile Ala Asp Ser Gln His Lys Ser His
            20                  25                  30

Arg Gln Met Val Thr Thr Thr Asn Pro Leu Ile Arg His Glu Asn Arg
        35                  40                  45

Met Val Leu Ala Ser Thr Thr Ala Lys Ala Met Glu Gln Met Ala Gly
    50                  55                  60

Ser Ser Glu Gln Ala Ala Glu Ala Met Glu Val Ala Ser Gln Ala Arg
65                  70                  75                  80

Gln Met Val Gln Ala Met Arg Ala Ile Gly Thr His Pro Ser Ser Ser
                85                  90                  95

Thr Gly Leu Arg Asn Asp Leu Leu Glu Asn Leu Gln Ala Tyr Gln Lys
            100                 105                 110

Arg Met Gly Val Gln Met Gln Arg Phe Lys
        115                 120


<210> SEQ ID NO 42
<211> LENGTH: 19
<212> TYPE: PRT
<213> ORGANISM: Influenza A virus

<400> SEQUENCE: 42

Gly Thr His Pro Ser Ser Ser Ala Gly Leu Lys Ser Asp Leu Leu Glu
1               5                   10                  15

Asn Leu Gln


<210> SEQ ID NO 43
```

-continued

<211> LENGTH: 122
<212> TYPE: PRT
<213> ORGANISM: Influenza A virus

<400> SEQUENCE: 43

Ile Tyr Asn Arg Met Gly Ala Val Thr Thr Glu Val Ala Phe Gly Leu
1 5 10 15

Val Cys Ala Thr Cys Glu Gln Ile Ala Asp Ser Gln His Arg Ser His
20 25 30

Arg Gln Met Val Thr Thr Thr Asn Pro Leu Ile Arg His Glu Asn Arg
35 40 45

Met Val Leu Ala Ser Thr Thr Ala Lys Ala Met Glu Gln Met Ala Gly
50 55 60

Ser Ser Glu Gln Ala Ala Glu Ala Met Asp Ile Ala Ser Gln Ala Arg
65 70 75 80

Gln Met Val Gln Ala Met Arg Thr Ile Gly Thr His Pro Ser Ser Ser
85 90 95

Ala Gly Leu Lys Asp Asp Leu Leu Glu Asn Leu Gln Ala Tyr Gln Lys
100 105 110

Arg Met Gly Val Gln Met Gln Arg Phe Lys
115 120

<210> SEQ ID NO 44
<211> LENGTH: 19
<212> TYPE: PRT
<213> ORGANISM: Influenza A virus

<400> SEQUENCE: 44

Gly Thr His Pro Ser Ser Ser Ala Gly Leu Arg Asp Asp Leu Leu Glu
1 5 10 15

Asn Leu Gln

<210> SEQ ID NO 45
<211> LENGTH: 122
<212> TYPE: PRT
<213> ORGANISM: Influenza A virus

<400> SEQUENCE: 45

Ile Tyr Asn Arg Met Gly Thr Val Thr Thr Glu Ala Ala Phe Gly Leu
1 5 10 15

Val Cys Ala Thr Cys Glu Gln Ile Ala Asp Ser Gln His Arg Ser His
20 25 30

Arg Gln Met Ala Thr Thr Thr Asn Pro Leu Ile Arg His Glu Asn Arg
35 40 45

Met Val Leu Ala Ser Thr Thr Ala Lys Ala Met Glu Gln Met Ala Gly
50 55 60

Ser Ser Glu Gln Ala Ala Glu Ala Met Glu Val Ala Asn Gln Thr Arg
65 70 75 80

Gln Met Val His Ala Met Arg Thr Ile Gly Thr His Pro Ser Ser Ser
85 90 95

Ala Gly Leu Arg Asp Asp Leu Leu Glu Asn Leu Gln Ala Tyr Gln Lys
100 105 110

Arg Met Gly Val Gln Met Gln Arg Phe Lys
115 120

<210> SEQ ID NO 46
<211> LENGTH: 19
<212> TYPE: PRT

<213> ORGANISM: Influenza A virus

<400> SEQUENCE: 46

```
Gly Thr His Pro Asn Ser Ser Ala Gly Leu Lys Asp Asp Leu Leu Glu
1               5                   10                  15

Asn Leu Gln


<210> SEQ ID NO 47
<211> LENGTH: 122
<212> TYPE: PRT
<213> ORGANISM: Influenza A virus

<400> SEQUENCE: 47

Ile Tyr Asn Arg Met Gly Thr Val Thr Thr Glu Ala Ala Phe Gly Leu
1               5                   10                  15

Val Cys Ala Thr Cys Glu Gln Ile Ala Asp Ser Gln His Arg Ser His
            20                  25                  30

Arg Gln Met Ala Thr Thr Thr Asn Pro Leu Ile Arg His Glu Asn Arg
        35                  40                  45

Met Val Leu Ala Ser Thr Thr Ala Lys Ala Met Glu Gln Met Ala Gly
    50                  55                  60

Ser Ser Glu Gln Ala Ala Glu Ala Met Glu Val Ala Asn Gln Thr Arg
65                  70                  75                  80

Gln Met Val His Ala Met Arg Thr Ile Gly Thr His Pro Ser Ser Ser
                85                  90                  95

Ala Gly Leu Lys Asp Asp Leu Leu Glu Asn Leu Gln Ala Tyr Gln Lys
            100                 105                 110

Arg Met Gly Val Gln Met Gln Arg Phe Lys
        115                 120


<210> SEQ ID NO 48
<211> LENGTH: 19
<212> TYPE: PRT
<213> ORGANISM: Influenza A virus

<400> SEQUENCE: 48

Gly Thr His Pro Ser Ser Ser Ala Gly Leu Lys Asp Asp Leu Leu Gly
1               5                   10                  15

Asn Leu Gln


<210> SEQ ID NO 49
<211> LENGTH: 122
<212> TYPE: PRT
<213> ORGANISM: Influenza A virus

<400> SEQUENCE: 49

Ile Tyr Asn Arg Met Gly Thr Val Thr Thr Glu Ala Ala Phe Gly Leu
1               5                   10                  15

Val Cys Ala Thr Cys Glu Gln Ile Ala Asp Ser Gln His Arg Ser His
            20                  25                  30

Arg Gln Met Ala Thr Thr Thr Asn Pro Leu Ile Arg His Glu Asn Arg
        35                  40                  45

Met Val Leu Ala Ser Thr Thr Ala Lys Ala Met Glu Gln Met Ala Gly
    50                  55                  60

Ser Ser Glu Gln Ala Ala Glu Ala Met Glu Val Ala Asn Gln Thr Arg
65                  70                  75                  80

Gln Met Val His Ala Met Arg Thr Ile Gly Thr His Pro Ser Ser Ser
                85                  90                  95
```

```
Ala Gly Leu Lys Asp Asp Leu Leu Gly Asn Leu Gln Ala Tyr Gln Lys
            100                 105                 110

Arg Met Gly Val Gln Met Gln Arg Phe Lys
        115                 120


<210> SEQ ID NO 50
<211> LENGTH: 19
<212> TYPE: PRT
<213> ORGANISM: Influenza A virus

<400> SEQUENCE: 50

Gly Thr His Pro Ser Ser Ser Ser Gly Leu Arg Asn Asp Leu Leu Glu
1               5                   10                  15

Asn Leu Gln


<210> SEQ ID NO 51
<211> LENGTH: 122
<212> TYPE: PRT
<213> ORGANISM: Influenza A virus

<400> SEQUENCE: 51

Ile Tyr Asn Arg Met Gly Thr Val Thr Thr Glu Ala Ala Phe Gly Leu
1               5                   10                  15

Val Cys Ala Thr Cys Glu Gln Ile Ala Asp Ser Gln His Arg Ser His
            20                  25                  30

Arg Gln Met Ala Thr Thr Thr Asn Pro Leu Ile Arg His Glu Asn Arg
        35                  40                  45

Met Val Leu Ala Ser Thr Thr Ala Lys Ala Met Glu Gln Met Ala Gly
    50                  55                  60

Ser Ser Glu Gln Ala Ala Glu Ala Met Glu Val Ala Asn Gln Thr Arg
65                  70                  75                  80

Gln Met Val His Ala Met Arg Thr Ile Gly Thr His Pro Ser Ser Ser
                85                  90                  95

Ser Gly Leu Arg Asp Asp Leu Leu Glu Asn Leu Gln Ala Tyr Gln Lys
            100                 105                 110

Arg Met Gly Val Gln Met Gln Arg Phe Lys
        115                 120


<210> SEQ ID NO 52
<211> LENGTH: 19
<212> TYPE: PRT
<213> ORGANISM: Influenza A virus

<400> SEQUENCE: 52

Gly Thr His Pro Ser Ser Ser Ala Gly Leu Arg Asp Asp Leu Leu Asp
1               5                   10                  15

Asn Leu Gln


<210> SEQ ID NO 53
<211> LENGTH: 122
<212> TYPE: PRT
<213> ORGANISM: Influenza A virus

<400> SEQUENCE: 53

Ile Tyr Asn Arg Met Gly Thr Val Thr Thr Glu Ala Ala Phe Gly Leu
1               5                   10                  15

Val Cys Ala Thr Cys Glu Gln Ile Ala Asp Ser Gln His Arg Ser His
            20                  25                  30
```

-continued

Arg Gln Met Ala Thr Thr Thr Asn Pro Leu Ile Arg His Glu Asn Arg
35 40 45

Met Val Leu Ala Ser Thr Thr Ala Lys Ala Met Glu Gln Met Ala Gly
50 55 60

Ser Ser Glu Gln Ala Ala Glu Ala Met Glu Val Ala Asn Gln Thr Arg
65 70 75 80

Gln Met Val His Ala Met Arg Thr Ile Gly Thr His Pro Ser Ser Ser
85 90 95

Ala Gly Leu Arg Asp Asp Leu Leu Asp Asn Leu Gln Ala Tyr Gln Lys
100 105 110

Arg Met Gly Val Gln Met Gln Arg Phe Lys
115 120

<210> SEQ ID NO 54
<211> LENGTH: 19
<212> TYPE: PRT
<213> ORGANISM: Influenza A virus

<400> SEQUENCE: 54

Gly Thr His Pro Ser Ser Ser Ala Gly Leu Lys Asp Asp Leu Leu Asp
1 5 10 15

Asn Leu Gln

<210> SEQ ID NO 55
<211> LENGTH: 122
<212> TYPE: PRT
<213> ORGANISM: Influenza A virus

<400> SEQUENCE: 55

Ile Tyr Asn Arg Met Gly Thr Val Thr Thr Glu Ala Ala Phe Gly Leu
1 5 10 15

Val Cys Ala Thr Cys Glu Gln Ile Ala Asp Ser Gln His Arg Ser His
20 25 30

Arg Gln Met Ala Thr Thr Thr Asn Pro Leu Ile Arg His Glu Asn Arg
35 40 45

Met Val Leu Ala Ser Thr Thr Ala Lys Ala Met Glu Gln Met Ala Gly
50 55 60

Ser Ser Glu Gln Ala Ala Glu Ala Met Glu Val Ala Asn Gln Thr Arg
65 70 75 80

Gln Met Val His Ala Met Arg Thr Ile Gly Thr His Pro Ser Ser Ser
85 90 95

Ala Gly Leu Lys Asp Asp Leu Leu Asp Asn Leu Gln Ala Tyr Gln Lys
100 105 110

Arg Met Gly Val Gln Met Gln Arg Phe Lys
115 120

<210> SEQ ID NO 56
<211> LENGTH: 19
<212> TYPE: PRT
<213> ORGANISM: Influenza A virus

<400> SEQUENCE: 56

Gly Thr His Pro Ser Ser Ser Ala Gly Leu Lys Asp Ala Leu Leu Glu
1 5 10 15

Asn Leu Gln

<210> SEQ ID NO 57
<211> LENGTH: 122

<212> TYPE: PRT
<213> ORGANISM: Influenza A virus

<400> SEQUENCE: 57

Ile Tyr Asn Arg Met Gly Thr Val Thr Thr Glu Ala Ala Phe Gly Leu
1 5 10 15

Val Cys Ala Thr Cys Glu Gln Ile Ala Asp Ser Gln His Arg Ser His
20 25 30

Arg Gln Met Ala Thr Thr Thr Asn Pro Leu Ile Arg His Glu Asn Arg
35 40 45

Met Val Leu Ala Ser Thr Thr Ala Lys Ala Met Glu Gln Met Ala Gly
50 55 60

Ser Ser Glu Gln Ala Ala Glu Ala Met Glu Val Ala Asn Gln Thr Arg
65 70 75 80

Gln Met Val His Ala Met Arg Thr Ile Gly Thr His Pro Ser Ser Ser
85 90 95

Ala Gly Leu Lys Asp Ala Leu Leu Glu Asn Leu Gln Ala Tyr Gln Lys
100 105 110

Arg Met Gly Val Gln Met Gln Arg Phe Lys
115 120

<210> SEQ ID NO 58
<211> LENGTH: 19
<212> TYPE: PRT
<213> ORGANISM: Influenza A virus

<400> SEQUENCE: 58

Gly Thr His Pro Ser Ser Ser Thr Gly Leu Arg Asp Asp Leu Leu Glu
1 5 10 15

Lys Leu Gln

<210> SEQ ID NO 59
<211> LENGTH: 122
<212> TYPE: PRT
<213> ORGANISM: Influenza A virus

<400> SEQUENCE: 59

Ile Tyr Asn Arg Met Gly Ala Val Thr Thr Glu Val Ala Phe Gly Leu
1 5 10 15

Val Cys Ala Thr Cys Glu Gln Ile Ala Asp Ser Gln His Arg Ser His
20 25 30

Arg Gln Met Val Ala Thr Thr Asn Pro Leu Ile Lys His Glu Asn Arg
35 40 45

Met Val Leu Ala Ser Thr Thr Ala Lys Ala Met Glu Gln Met Ala Gly
50 55 60

Ser Ser Glu Gln Ala Ala Glu Ala Met Glu Ile Ala Ser Gln Ala Arg
65 70 75 80

Gln Met Val Gln Ala Met Arg Ala Ile Gly Thr His Pro Ser Ser Ser
85 90 95

Thr Gly Leu Arg Asp Asp Leu Leu Glu Lys Leu Gln Thr Tyr Gln Lys
100 105 110

Arg Met Gly Val Gln Met Gln Arg Phe Lys
115 120

<210> SEQ ID NO 60
<211> LENGTH: 19
<212> TYPE: PRT
<213> ORGANISM: Influenza A virus

<400> SEQUENCE: 60

Gly Thr His Pro Ser Ser Ser Thr Gly Leu Arg Asp Asn Leu Leu Glu
1 5 10 15

Asn Leu Gln

<210> SEQ ID NO 61
<211> LENGTH: 122
<212> TYPE: PRT
<213> ORGANISM: Influenza A virus

<400> SEQUENCE: 61

Ile Tyr Asn Arg Met Gly Ala Val Thr Thr Glu Val Ala Phe Gly Leu
1 5 10 15

Val Cys Ala Thr Cys Glu Gln Ile Ala Asp Ser Gln His Arg Ser His
20 25 30

Arg Gln Met Val Ala Thr Thr Asn Pro Leu Ile Lys His Glu Asn Arg
35 40 45

Met Val Leu Ala Ser Thr Thr Ala Lys Ala Met Glu Gln Met Ala Gly
50 55 60

Ser Ser Glu Gln Ala Ala Glu Ala Met Glu Ile Ala Ser Gln Ala Arg
65 70 75 80

Gln Met Val Gln Ala Met Arg Ala Ile Gly Thr His Pro Ser Ser Ser
85 90 95

Thr Gly Leu Arg Asp Asn Leu Leu Glu Asn Leu Gln Thr Tyr Gln Lys
100 105 110

Arg Met Gly Val Gln Met Gln Arg Phe Lys
115 120

<210> SEQ ID NO 62
<211> LENGTH: 19
<212> TYPE: PRT
<213> ORGANISM: Influenza A virus

<400> SEQUENCE: 62

Gly Thr His Pro Ser Ser Ser Asn Gly Leu Arg Asp Asp Leu Leu Glu
1 5 10 15

Asn Leu Gln

<210> SEQ ID NO 63
<211> LENGTH: 122
<212> TYPE: PRT
<213> ORGANISM: Influenza A virus

<400> SEQUENCE: 63

Ile Tyr Asn Arg Met Gly Ala Val Thr Thr Glu Val Ala Phe Gly Leu
1 5 10 15

Val Cys Ala Thr Cys Glu Gln Ile Ala Asp Ser Gln His Arg Ser His
20 25 30

Arg Gln Met Val Ala Thr Thr Asn Pro Leu Ile Arg His Glu Asn Arg
35 40 45

Met Val Leu Ala Ser Thr Thr Ala Lys Ala Met Glu Gln Met Ala Gly
50 55 60

Ser Ser Glu Gln Ala Ala Glu Ala Met Glu Ile Ala Ser Gln Ala Arg
65 70 75 80

Gln Met Val Gln Ala Met Arg Ala Ile Gly Thr His Pro Ser Ser Ser
85 90 95

```
Asn Gly Leu Arg Asp Asp Leu Leu Glu Asn Leu Gln Thr Tyr Gln Lys
            100                 105                 110

Arg Met Gly Val Gln Met Gln Arg Phe Lys
        115                 120


<210> SEQ ID NO 64
<211> LENGTH: 19
<212> TYPE: PRT
<213> ORGANISM: Influenza A virus

<400> SEQUENCE: 64

Gly Thr His Pro Ser Ser Ser Thr Gly Leu Arg Asp Asp Leu Leu Gly
1               5                   10                  15

Asn Leu Gln


<210> SEQ ID NO 65
<211> LENGTH: 122
<212> TYPE: PRT
<213> ORGANISM: Influenza A virus

<400> SEQUENCE: 65

Ile Tyr Asn Arg Met Gly Ala Val Thr Thr Glu Val Ala Phe Gly Leu
1               5                   10                  15

Val Cys Ala Thr Cys Glu Gln Ile Ala Asp Ser Gln His Arg Ser His
            20                  25                  30

Arg Gln Met Val Ala Thr Thr Asn Pro Leu Ile Lys His Glu Asn Arg
        35                  40                  45

Met Val Leu Ala Ser Thr Thr Ala Lys Ala Met Glu Gln Met Ala Gly
    50                  55                  60

Ser Ser Glu Gln Ala Ala Glu Ala Met Glu Ile Ala Ser Gln Ala Arg
65                  70                  75                  80

Gln Met Val Gln Ala Met Arg Ala Ile Gly Thr His Pro Ser Ser Ser
                85                  90                  95

Thr Gly Leu Arg Asp Asp Leu Leu Gly Asn Leu Gln Thr Tyr Gln Lys
            100                 105                 110

Arg Met Gly Val Gln Met Gln Arg Phe Lys
        115                 120


<210> SEQ ID NO 66
<211> LENGTH: 19
<212> TYPE: PRT
<213> ORGANISM: Influenza A virus

<400> SEQUENCE: 66

Gly Thr His Pro Ser Ser Ser Thr Gly Leu Arg Asp Asp Leu Leu Asp
1               5                   10                  15

Asn Leu Gln


<210> SEQ ID NO 67
<211> LENGTH: 122
<212> TYPE: PRT
<213> ORGANISM: Influenza A virus

<400> SEQUENCE: 67

Ile Tyr Asn Arg Met Gly Ala Val Thr Thr Glu Val Ala Phe Gly Leu
1               5                   10                  15

Val Cys Ala Thr Cys Glu Gln Ile Ala Asp Ser Gln His Arg Ser His
            20                  25                  30

Arg Gln Met Val Ala Thr Thr Asn Pro Leu Ile Arg His Glu Asn Arg
```

```
        35                  40                  45

Met Val Leu Ala Ser Thr Thr Ala Lys Ala Met Glu Gln Met Ala Gly
    50                  55                  60

Ser Ser Glu Gln Ala Ala Glu Ala Met Glu Ile Ala Ser Gln Ala Arg
65                  70                  75                  80

Gln Met Val Gln Ala Met Arg Ala Val Gly Thr His Pro Ser Ser Ser
                85                  90                  95

Thr Gly Leu Arg Asp Asp Leu Leu Asp Asn Leu Gln Thr Tyr Gln Lys
            100                 105                 110

Arg Met Gly Val Gln Met Gln Arg Phe Lys
        115                 120


<210> SEQ ID NO 68
<211> LENGTH: 19
<212> TYPE: PRT
<213> ORGANISM: Influenza A virus

<400> SEQUENCE: 68

Gly Thr His Pro Ser Ser Ser Thr Gly Leu Arg Gly Asp Leu Leu Glu
1               5                   10                  15

Asn Leu Gln


<210> SEQ ID NO 69
<211> LENGTH: 122
<212> TYPE: PRT
<213> ORGANISM: Influenza A virus

<400> SEQUENCE: 69

Ile Tyr Asn Arg Met Gly Ala Val Thr Thr Glu Val Ala Phe Gly Leu
1               5                   10                  15

Val Cys Ala Thr Cys Glu Gln Ile Ala Asp Ser Gln His Arg Ser His
            20                  25                  30

Arg Gln Met Val Ala Thr Thr Asn Pro Leu Ile Lys His Glu Asn Arg
        35                  40                  45

Met Val Leu Ala Ser Thr Thr Ala Lys Ala Met Glu Gln Met Ala Gly
    50                  55                  60

Ser Ser Glu Gln Ala Ala Glu Ala Met Glu Ile Ala Ser Gln Ala Arg
65                  70                  75                  80

Gln Met Val Gln Ala Met Arg Ala Ile Gly Thr His Pro Ser Ser Ser
                85                  90                  95

Thr Gly Leu Arg Gly Asp Leu Leu Glu Asn Leu Gln Thr Tyr Gln Lys
            100                 105                 110

Arg Met Gly Val Gln Met Gln Arg Phe Arg
        115                 120


<210> SEQ ID NO 70
<211> LENGTH: 19
<212> TYPE: PRT
<213> ORGANISM: Influenza A virus

<400> SEQUENCE: 70

Gly Thr His Pro Ser Ser Ser Thr Gly Leu Arg Asp Asp Leu Leu Ile
1               5                   10                  15

Asn Leu Gln


<210> SEQ ID NO 71
<211> LENGTH: 122
<212> TYPE: PRT
```

<213> ORGANISM: Influenza A virus

<400> SEQUENCE: 71

```
Ile Tyr Asn Arg Met Gly Ala Val Thr Thr Glu Val Ala Phe Gly Leu
1               5                   10                  15

Val Cys Ala Thr Cys Glu Gln Ile Ala Asp Ser Gln His Arg Ser His
            20                  25                  30

Arg Gln Met Val Ser Thr Thr Asn Pro Leu Ile Lys His Glu Asn Arg
        35                  40                  45

Met Val Leu Ala Ser Thr Thr Ala Arg Ala Met Glu Gln Met Ala Gly
    50                  55                  60

Ser Ser Glu Gln Ala Ala Glu Ala Met Glu Ile Ala Ser Gln Ala Arg
65                  70                  75                  80

Gln Met Val Gln Ala Met Arg Ala Ile Gly Thr His Pro Ser Ser Ser
                85                  90                  95

Thr Gly Leu Arg Asp Asp Leu Ile Glu Asn Leu Gln Thr Tyr Gln Lys
            100                 105                 110

Arg Met Gly Val Gln Met Gln Arg Phe Lys
        115                 120
```

<210> SEQ ID NO 72
<211> LENGTH: 19
<212> TYPE: PRT
<213> ORGANISM: Influenza A virus

<400> SEQUENCE: 72

```
Gly Thr Pro Pro Ser Ser Ser Ala Gly Leu Lys Asn Asp Leu Leu Glu
1               5                   10                  15

Asn Leu Gln
```

<210> SEQ ID NO 73
<211> LENGTH: 122
<212> TYPE: PRT
<213> ORGANISM: Influenza A virus

<400> SEQUENCE: 73

```
Ile Tyr Asn Arg Met Gly Ala Val Thr Thr Glu Val Ala Phe Gly Leu
1               5                   10                  15

Val Cys Ala Thr Cys Glu Gln Ile Ala Asp Ser Gln His Arg Ser His
            20                  25                  30

Arg Gln Met Val Thr Thr Thr Asn Pro Leu Ile Arg His Glu Asn Arg
        35                  40                  45

Met Val Leu Ala Ser Thr Thr Ala Lys Ala Met Glu Gln Met Ala Gly
    50                  55                  60

Ser Ser Glu Gln Ala Ala Glu Ala Met Glu Val Ala Ser Gln Ala Arg
65                  70                  75                  80

Gln Met Val Gln Ala Met Arg Ala Ile Gly Thr Pro Pro Ser Ser Ser
                85                  90                  95

Ala Gly Leu Lys Asp Asp Leu Leu Glu Asn Leu Gln Ala Tyr Gln Lys
            100                 105                 110

Arg Met Gly Val Gln Met Gln Arg Phe Lys
        115                 120
```

<210> SEQ ID NO 74
<211> LENGTH: 19
<212> TYPE: PRT
<213> ORGANISM: Influenza A virus

<400> SEQUENCE: 74

Gly Thr Pro Pro Ser Ser Ser Ala Gly Leu Lys Asp Asp Leu Leu Glu
1 5 10 15

Asn Leu Gln

<210> SEQ ID NO 75
<211> LENGTH: 122
<212> TYPE: PRT
<213> ORGANISM: Influenza A virus

<400> SEQUENCE: 75

Ile Tyr Asn Arg Met Gly Ala Val Thr Thr Glu Val Ala Phe Gly Leu
1 5 10 15

Val Cys Ala Thr Cys Glu Gln Ile Ala Asp Ser Gln His Arg Ser His
20 25 30

Arg Gln Met Val Thr Thr Thr Asn Pro Leu Ile Arg His Glu Asn Arg
35 40 45

Met Val Leu Ala Ser Thr Thr Ala Lys Ala Met Glu Gln Met Ala Gly
50 55 60

Ser Ser Glu Gln Ala Ala Glu Ala Met Glu Val Ala Ser Gln Ala Arg
65 70 75 80

Gln Met Val Gln Ala Met Arg Ala Ile Gly Thr Pro Pro Ser Ser Ser
85 90 95

Ala Gly Leu Lys Asp Asp Leu Leu Glu Asn Leu Gln Ala Tyr Gln Lys
100 105 110

Arg Met Gly Val Gln Met Gln Arg Phe Lys
115 120

<210> SEQ ID NO 76
<211> LENGTH: 19
<212> TYPE: PRT
<213> ORGANISM: Artificial Sequence
<220> FEATURE:
<223> OTHER INFORMATION: Influenza A M1 artificial polypeptide
<220> FEATURE:
<221> NAME/KEY: Xaa
<222> LOCATION: (3)..(3)
<223> OTHER INFORMATION: Xaa is His, Arg or Asn
<220> FEATURE:
<221> NAME/KEY: Xaa
<222> LOCATION: (5)..(5)
<223> OTHER INFORMATION: Xaa is Ser, Arg, or Asn
<220> FEATURE:
<221> NAME/KEY: Xaa
<222> LOCATION: (8)..(8)
<223> OTHER INFORMATION: Xaa is Ala, Thr, or Asn
<220> FEATURE:
<221> NAME/KEY: Xaa
<222> LOCATION: (11)..(11)
<223> OTHER INFORMATION: Xaa is Lys or Arg
<220> FEATURE:
<221> NAME/KEY: Xaa
<222> LOCATION: (12)..(12)
<223> OTHER INFORMATION: Xaa is Asn, Asp, Ser, or Lys
<220> FEATURE:
<221> NAME/KEY: Xaa
<222> LOCATION: (13)..(13)
<223> OTHER INFORMATION: Xaa is Asp, Asn, or Gly
<220> FEATURE:
<221> NAME/KEY: Xaa
<222> LOCATION: (15)..(15)
<223> OTHER INFORMATION: Xaa is Leu, Phe, or Ile
<220> FEATURE:
<221> NAME/KEY: Xaa
<222> LOCATION: (16)..(16)
<223> OTHER INFORMATION: Xaa is Glu, Asp, His, or Lys
<220> FEATURE:

<221> NAME/KEY: Xaa
<222> LOCATION: (17)..(17)
<223> OTHER INFORMATION: Xaa is Asn, His, or Lys

<400> SEQUENCE: 76

Gly Thr Xaa Pro Xaa Ser Ser Xaa Gly Leu Xaa Xaa Xaa Leu Xaa Xaa
1 5 10 15

Xaa Leu Gln

<210> SEQ ID NO 77
<211> LENGTH: 19
<212> TYPE: PRT
<213> ORGANISM: Artificial Sequence
<220> FEATURE:
<223> OTHER INFORMATION: Influenza M1 artificial polypeptide
<220> FEATURE:
<221> NAME/KEY: Xaa
<222> LOCATION: (1)..(19)
<223> OTHER INFORMATION: Xaa is any amino acid

<400> SEQUENCE: 77

Gly Thr Xaa Pro Xaa Ser Ser Xaa Gly Leu Xaa Xaa Xaa Leu Xaa Xaa
1 5 10 15

Xaa Leu Gln

<210> SEQ ID NO 78
<211> LENGTH: 122
<212> TYPE: PRT
<213> ORGANISM: Artificial Sequence
<220> FEATURE:
<223> OTHER INFORMATION: Influenza M1 artificial polypeptide
<220> FEATURE:
<221> NAME/KEY: Xaa
<222> LOCATION: (7)..(7)
<223> OTHER INFORMATION: Xaa is Ala or Thre
<220> FEATURE:
<221> NAME/KEY: Xaa
<222> LOCATION: (9)..(9)
<223> OTHER INFORMATION: Xaa is Thr or Ala
<220> FEATURE:
<221> NAME/KEY: Xaa
<222> LOCATION: (12)..(12)
<223> OTHER INFORMATION: Xaa is Val, Ser, or Ala
<220> FEATURE:
<221> NAME/KEY: Xaa
<222> LOCATION: (17)..(17)
<223> OTHER INFORMATION: Xaa is Val or Ile
<220> FEATURE:
<221> NAME/KEY: Xaa
<222> LOCATION: (30)..(30)
<223> OTHER INFORMATION: Xaa is Arg or Lys
<220> FEATURE:
<221> NAME/KEY: Xaa
<222> LOCATION: (36)..(36)
<223> OTHER INFORMATION: Xaa is Val or Ala
<220> FEATURE:
<221> NAME/KEY: Xaa
<222> LOCATION: (37)..(37)
<223> OTHER INFORMATION: Xaa is Thr, Ala, or Ser
<220> FEATURE:
<221> NAME/KEY: Xaa
<222> LOCATION: (44)..(44)
<223> OTHER INFORMATION: Xaa is Arg or Lys
<220> FEATURE:
<221> NAME/KEY: Xaa
<222> LOCATION: (51)..(51)
<223> OTHER INFORMATION: Xaa is Leu or Ile
<220> FEATURE:
<221> NAME/KEY: Xaa
<222> LOCATION: (57)..(57)
<223> OTHER INFORMATION: Xaa is Lys or Arg
<220> FEATURE:
<221> NAME/KEY: Xaa
<222> LOCATION: (70)..(70)
<223> OTHER INFORMATION: Xaa is Ala or Ser
<220> FEATURE:
<221> NAME/KEY: Xaa
<222> LOCATION: (75)..(75)
<223> OTHER INFORMATION: Xaa is Val, Asp, or Ile
<220> FEATURE:
<221> NAME/KEY: Xaa
<222> LOCATION: (76)..(76)
<223> OTHER INFORMATION: Xaa is Ala or Ile
<220> FEATURE:
<221> NAME/KEY: Xaa
<222> LOCATION: (77)..(77)
<223> OTHER INFORMATION: Xaa is Ser or Asn
<220> FEATURE:
<221> NAME/KEY: Xaa
<222> LOCATION: (79)..(79)
<223> OTHER INFORMATION: Xaa is Ala or Thr
<220> FEATURE:
<221> NAME/KEY: Xaa
<222> LOCATION: (84)..(84)
<223> OTHER INFORMATION: Xaa is Gln or His
<220> FEATURE:
<221> NAME/KEY: Xaa
<222> LOCATION: (88)..(88)
<223> OTHER INFORMATION: Xaa is Thr or Ala
<220> FEATURE:
<221> NAME/KEY: Xaa
<222> LOCATION: (89)..(89)
<223> OTHER INFORMATION: Xaa is Ile or Val
<220> FEATURE:
<221> NAME/KEY: Xaa
<222> LOCATION: (92)..(92)
<223> OTHER INFORMATION: Xaa is His, Arg, Pro, or Asn
<220> FEATURE:
<221> NAME/KEY: Xaa
<222> LOCATION: (94)..(94)
<223> OTHER INFORMATION: Xaa is Ser, Asn, or Arg
<220> FEATURE:
<221> NAME/KEY: Xaa
<222> LOCATION: (97)..(97)
<223> OTHER INFORMATION: Xaa is Ala, Thr, Asn, or Ser
<220> FEATURE:
<221> NAME/KEY: Xaa
<222> LOCATION: (100)..(100)
<223> OTHER INFORMATION: Xaa is Lys, Arg, or Gly
<220> FEATURE:
<221> NAME/KEY: Xaa
<222> LOCATION: (101)..(101)
<223> OTHER INFORMATION: Xaa is Asn, Asp, Ser, or Lys
<220> FEATURE:
<221> NAME/KEY: Xaa
<222> LOCATION: (102)..(102)
<223> OTHER INFORMATION: Xaa is Asp, Asn, Ala, or Gly
<220> FEATURE:
<221> NAME/KEY: Xaa
<222> LOCATION: (104)..(104)
<223> OTHER INFORMATION: Xaa is Leu, Ile, or Phe
<220> FEATURE:
<221> NAME/KEY: Xaa
<222> LOCATION: (105)..(105)
<223> OTHER INFORMATION: Xaa is Glu, Asp, Gly, His, or Lys
<220> FEATURE:
<221> NAME/KEY: Xaa
<222> LOCATION: (106)..(106)
<223> OTHER INFORMATION: Xaa is Asn, Lys, or His
<220> FEATURE:
<221> NAME/KEY: Xaa
<222> LOCATION: (109)..(109)
<223> OTHER INFORMATION: Xaa is Ala or Thr

<400> SEQUENCE: 78

```
Ile Tyr Asn Arg Met Gly Xaa Val Xaa Thr Glu Xaa Ala Phe Gly Leu
1               5                   10                  15

Xaa Cys Ala Thr Cys Glu Gln Ile Ala Asp Ser Gln His Xaa Ser His
            20                  25                  30
```

```
Arg Gln Met Xaa Xaa Thr Thr Asn Pro Leu Ile Xaa His Glu Asn Arg
        35                  40                  45

Met Val Xaa Ala Ser Thr Thr Ala Xaa Ala Met Glu Gln Met Ala Gly
    50                  55                  60

Ser Ser Glu Gln Ala Xaa Glu Ala Met Glu Xaa Xaa Xaa Gln Xaa Arg
65                  70                  75                  80

Gln Met Val Xaa Ala Met Arg Xaa Ile Gly Thr Xaa Pro Xaa Ser Ser
                85                  90                  95

Xaa Gly Leu Xaa Xaa Xaa Leu Xaa Xaa Xaa Leu Gln Xaa Tyr Gln Lys
            100                 105                 110

Arg Met Gly Val Gln Met Gln Arg Phe Lys
        115                 120


<210> SEQ ID NO 79
<211> LENGTH: 122
<212> TYPE: PRT
<213> ORGANISM: Artificial Sequence
<220> FEATURE:
<223> OTHER INFORMATION: Influenza M1 artificial polypeptide
<220> FEATURE:
<221> NAME/KEY: Xaa
<222> LOCATION: (1)..(122)
<223> OTHER INFORMATION: Xaa is any amino acid

<400> SEQUENCE: 79

Ile Tyr Asn Arg Met Gly Xaa Val Xaa Thr Glu Xaa Ala Phe Gly Leu
1               5                   10                  15

Xaa Cys Ala Thr Cys Glu Gln Ile Ala Asp Ser Gln His Xaa Ser His
            20                  25                  30

Arg Gln Met Xaa Xaa Thr Thr Asn Pro Leu Ile Xaa His Glu Asn Arg
        35                  40                  45

Met Val Xaa Ala Ser Thr Thr Ala Xaa Ala Met Glu Gln Met Ala Gly
    50                  55                  60

Ser Ser Glu Gln Ala Xaa Glu Ala Met Glu Xaa Xaa Xaa Gln Xaa Arg
65                  70                  75                  80

Gln Met Val Xaa Ala Met Arg Xaa Ile Gly Thr Xaa Pro Xaa Ser Ser
                85                  90                  95

Xaa Gly Leu Xaa Xaa Xaa Leu Xaa Xaa Xaa Leu Gln Xaa Tyr Gln Lys
            100                 105                 110

Arg Met Gly Val Gln Met Gln Arg Phe Lys
        115                 120


<210> SEQ ID NO 80
<211> LENGTH: 20
<212> TYPE: PRT
<213> ORGANISM: Influenza A virus

<400> SEQUENCE: 80

Leu Leu Glu Asn Leu Gln Ala Tyr Gln Lys Arg Met Gly Val Gln Met
1               5                   10                  15

Gln Arg Phe Lys
            20


<210> SEQ ID NO 81
<211> LENGTH: 17
<212> TYPE: PRT
<213> ORGANISM: Influenza A virus

<400> SEQUENCE: 81

Gly His Thr Pro Ser Ser Ser Ala Gly Leu Lys Asn Asp Leu Leu Glu
```

-continued

```
1               5                   10                  15

Asn


<210> SEQ ID NO 82
<211> LENGTH: 19
<212> TYPE: PRT
<213> ORGANISM: Influenza A virus

<400> SEQUENCE: 82

Gly His Thr Pro Ser Ser Ser Ala Gly Leu Lys Asn Asp Leu Leu Glu
1               5                   10                  15

Asn Leu Gln
```